United States Patent
Bremer et al.

(10) Patent No.: US 6,793,984 B2
(45) Date of Patent: Sep. 21, 2004

(54) FLUORINATED (DIHYDRO) PHENANTHRENE DERIVATIVES, AND THEIR USE IN LIQUID-CRYSTALLINE MEDIA

(75) Inventors: Matthias Bremer, Darmstadt (DE); Detlef Pauluth, Ober-Ramstadt (DE); Michael Heckmeier, Bensheim (DE); Hans-Rolf Dübal, Eltville (DE); Barbara Hornung, Hasselroth (DE); Wolfgang Schmidt, Cologne (DE); Rainer Wingen, Hattersheim (DE)

(73) Assignee: Merck Patent Beschraenkter Haftung, Darmstadt (DE)

( * ) Notice: Subject to any disclaimer, the term of this patent is extended or adjusted under 35 U.S.C. 154(b) by 0 days.

(21) Appl. No.: 10/163,868

(22) Filed: Jun. 7, 2002

(65) Prior Publication Data
US 2003/0227000 A1 Dec. 11, 2003

(30) Foreign Application Priority Data
Jun. 7, 2001 (DE) .......................... 101 27 482
Jul. 28, 2001 (DE) .......................... 101 36 965

(51) Int. Cl.⁷ .................. C09K 19/32; C09K 19/30; C09K 19/12
(52) U.S. Cl. .............. 428/1.1; 252/299.62; 252/299.63; 252/299.66
(58) Field of Search ................ 252/299.62, 299.63, 252/299.66; 428/1.1

(56) References Cited

U.S. PATENT DOCUMENTS 6,168,838 B1 * 1/2001 Schmidt et al. ............. 428/1.1
6,482,478 B1 * 11/2002 Wingen ...................... 428/1.1
6,495,220 B2 * 12/2002 Dubal et al. ................ 428/1.1

FOREIGN PATENT DOCUMENTS

WO    WO-01/10803    * 2/2001

OTHER PUBLICATIONS

Derwent English abstract of WO 01/10803 (2001–226501), 2001.*

* cited by examiner

*Primary Examiner*—Shean C. Wu
(74) *Attorney, Agent, or Firm*—Millen White Zelano & Branigan, P.C.

(57) ABSTRACT

The invention relates to liquid-crystalline (dihydro) phenanthrene derivatives of the formula I

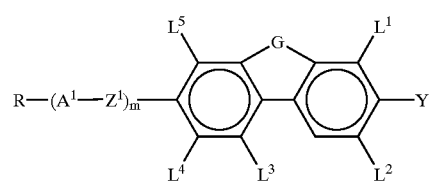

in which R, G, $A^1$, $Z^1$, m, $L^1$, $L^2$, $L^3$, $L^4$, $L^5$ and Y are as defined in claim 1, and to liquid-crystalline media comprising at least one (dihydro)phenanthrene derivative of the formula I, and to electro-optical displays containing a liquid-crystalline medium of this type.

19 Claims, No Drawings

FLUORINATED (DIHYDRO) PHENANTHRENE DERIVATIVES, AND THEIR USE IN LIQUID-CRYSTALLINE MEDIA

The present invention relates to liquid-crystalline fluorinated (dihydro)phenanthrene derivatives and to a liquid-crystalline medium, to the use thereof for electro-optical purposes, and to displays containing this medium.

Liquid crystals are used principally as dielectrics in display devices, since the optical properties of such substances can be modified by an applied voltage. Electro-optical devices based on liquid crystals are extremely well known to the person skilled in the art and can be based on various effects. Examples of such devices are cells having dynamic scattering, DAP (deformation of aligned phases) cells, guest/host cells, TN cells having a twisted nematic structure, STN (supertwisted nematic) cells, SBE (super-birefringence effect) cells and OMI (optical mode interference) cells. The commonest display devices are based on the Schadt-Helfrich effect and have a twisted nematic structure.

The liquid-crystal materials must have good chemical and thermal stability and good stability to electric fields and electromagnetic radiation. Furthermore, the liquid-crystal materials should have low viscosity and produce short addressing times, low threshold voltages and high contrast in the cells.

They should furthermore have a suitable mesophase, for example a nematic or cholesteric mesophase for the above-mentioned cells, at the usual operating temperatures, i.e. in the broadest possible range above and below room temperature. Since liquid crystals are generally used as mixtures of a plurality of components, it is important that the components are readily miscible with one another. Further properties, such as the electrical conductivity, the dielectric anisotropy and the optical anisotropy, have to satisfy various requirements depending on the cell type and area of application. For example, materials for cells having a twisted nematic structure should have positive dielectric anisotropy and low electrical conductivity.

For example, for matrix liquid-crystal displays with integrated non-linear elements for switching individual pixels (MLC displays), media having large positive dielectric anisotropy, broad nematic phases, relatively low birefringence, very high specific resistance, good UV and temperature stability and low vapour pressure are desired.

Matrix liquid-crystal displays of this type are known. Non-linear elements which can be used for individual switching of the individual pixels are, for example, active elements (i.e. transistors). The term "active matrix" is then used, where a distinction can be made between two types:
1. MOS (metal oxide semiconductor) or other diodes on a silicon wafer as substrate.
2. Thin-film transistors (TFTs) on a glass plate as substrate.

The use of single-crystal silicon as substrate material restricts the display size, since even modular assembly of various part-displays results in problems at the joins.

In the case of the more promising type 2, which is preferred, the electro-optical effect used is usually the TN effect. A distinction is made between two technologies: TFTs comprising compound semiconductors, such as, for example, CdSe, or TFTs based on polycrystalline or amorphous silicon. Intensive work is being carried out worldwide on the latter technology.

The TFT matrix is applied to the inside of one glass plate of the display, while the other glass plate carries the transparent counterelectrode on its inside. Compared with the size of the pixel electrode, the TFT is very small and has virtually no adverse effect on the image. This technology can also be extended to fully colour-capable displays, in which a mosaic of red, green and blue filters is arranged in such a way that a filter element is opposite each switchable pixel.

The TFT displays usually operate as TN cells with crossed polarisers in transmission and are illuminated from the back.

The term MLC displays here covers any matrix display with integrated non-linear elements, i.e., besides the active matrix, also displays with passive elements, such as varistors or diodes (MIM=metal-insulator-metal).

MLC displays of this type are particularly suitable for TV applications (for example pocket TVs) or for high-information displays for computer applications (laptops) and in automobile or aircraft construction. Besides problems regarding the angle dependence of the contrast and the response times, difficulties also arise in MLC displays due to insufficiently high specific resistance of the liquid-crystal mixtures [TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210–288 Matrix LCD Controlled by Double Stage Diode Rings, p. 141 ff, Paris; STROMER, M., Proc. Eurodisplay 84, Sept. 1984: Design of Thin Film Transistors for Matrix Addressing of Television Liquid Crystal Displays, p. 145 ff, Paris]. With decreasing resistance, the contrast of an MLC display deteriorates, and the problem of after-image elimination may occur. Since the specific resistance of the liquid-crystal mixture generally drops over the life of an MLC display owing to interaction with the interior surfaces of the display, a high (initial) resistance is very important in order to obtain acceptable service lives. In particular in the case of low-volt mixtures, it was hitherto impossible to achieve very high specific resistance values. It is furthermore important that the specific resistance exhibits the smallest possible increase with increasing temperature and after heating and/or UV exposure. The low-temperature properties of the mixtures from the prior art are also particularly disadvantageous. It is demanded that no crystallisation and/or smectic phases occur, even at low temperatures, and the temperature dependence of the viscosity is as low as possible. The MLC displays from the prior art thus do not meet today's requirements.

There thus continues to be a great demand for MLC displays having very high specific resistance at the same time as a large working-temperature range, short response times even at low temperatures and low threshold voltage which do not have these disadvantages, or only do so to a reduced extent.

In TN (Schadt-Helfrich) cells, media are desired which facilitate the following advantages in the cells:
  smaller layer thicknesses (higher An) for faster response times
  extended nematic phase range (in particular down to low temperatures)
  the ability to switch at extremely low temperatures (outdoor use, automobile, avionics)
  increased resistance to UV radiation (longer service life).

The media available from the prior art do not allow these advantages to be achieved while simultaneously retaining the other parameters.

In the case of supertwisted (STN) cells, media are desired which enable greater multiplexability and/or lower threshold voltages and/or broader nematic phase ranges (in particular at low temperatures). To this end, a further widening of the available parameter latitude (clearing point, smectic-nematic transition or melting point, viscosity, dielectric parameters, elastic parameters) is urgently desired.

The invention has the object of providing media, in particular for MLC, TN or STN displays of this type as well as for IPS displays, which do not have the above-mentioned disadvantages or only do so to a reduced extent, and preferably simultaneously have very high specific resistances and low threshold voltages.

It has now been found that this object can be achieved if the liquid-crystalline (dihydro)phenanthrene derivatives according to the invention are used in liquid-crystalline media.

The invention thus relates to liquid-crystalline (dihydro)phenanthrene derivatives of the formula I

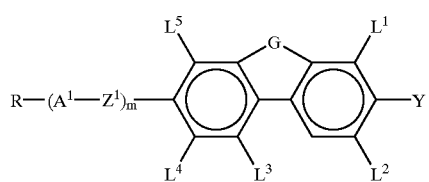

I in which
R is an alkyl or alkenyl radical having up to 15 carbon atoms which is unsubstituted, monosubstituted by CN or $CF_3$ or at least monosubstituted by halogen, where, in addition, one or more $CH_2$ groups in these radicals may be replaced by —O—, —S—, —C≡C—, —OC—C— or —O—CO— in such a way that O atoms are not linked directly to one another,
$A^1$ a) is a 1,4-cyclohexenylene or 1,4-cyclohexylene radical, in which one or two non-adjacent $CH_2$ groups may be replaced by —O— or —S—, or
b) a 1,4-phenylene radical, in which one or two CH groups may be replaced by N,
where the radicals a) and b) may be monosubstituted or polysubstituted by fluorine,
$Z^1$ is —CO—O—, —O—CO—, —$CF_2$O—, —O$CF_2$—, —$CH_2$O—, —O$CH_2$—, —$CH_2CH_2$—, —$C_2F_4$—, —CH=CH—, —C≡C— or a single bond,
Y is H, F, Cl, CN, $SF_5$, NCS, SCN or an alkyl, alkenyl, alkenyloxy or alkoxy radical having up to 5 carbon atoms which is monohalogenated or polyhalogenated,
G is —$CH_2CH_2$—, —CH=CF— or —CH=CH—,
$L^1$, $L^2$, $L^3$,
$L^4$ and $L^5$ are each, independently of one another, H or F, and
m is 0, 1 or 2.

The invention furthermore relates to liquid-crystalline media which comprise the (dihydro)phenanthrene derivatives according to the invention.

The compounds of the formula I have a broad range of applications. Depending on the choice of substituents, these compounds can serve as base materials of which liquid-crystalline media are predominantly composed; however, it is also possible to add compounds of the formula I to liquid-crystalline base materials from other classes of compound in order, for example, to modify the dielectric and/or optical anisotropy of a dielectric of this type and/or in order to optimise its threshold voltage and/or its viscosity.

In the pure state, the compounds of the formula I are colourless and form liquid-crystalline mesophases in a temperature range which is favourably located for electro-optical use. In particular, the compounds according to the invention are distinguished by their high clearing point. They are stable chemically, thermally and to light.

The invention relates in particular to the compounds of the formula I in which R is an alkyl radical having from 1 to 10 carbon atoms or an alkenyl radical having from 2 to 10 carbon atoms.

Particular preference is given to compounds of the formula I in which $L^1$ and/or $L^2$ are fluorine. m is preferably 0. $Z^1$ is preferably a single bond, furthermore —$CF_2$O—, —O$CF_2$—, —$C_2F_4$—, —$CH_2$O—, —O$CH_2$— or —COO—.

If R is an alkyl radical and/or an alkoxy radical, this may be straight-chain or branched. It is preferably straight-chain, has 1, 2, 3, 4, 5, 6 or 7 carbon atoms and accordingly is preferably methyl, ethyl, propyl, butyl, pentyl, hexyl, heptyl, ethoxy, propoxy, butoxy, pentoxy, hexyloxy or heptyloxy, furthermore octyl, nonyl, decyl, undecyl, dodecyl, tridecyl, tetradecyl, pentadecyl, methoxy, octyloxy, nonyloxy, decyloxy, undecyloxy, dodecyloxy, tridecyloxy or tetradecyloxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If R is an alkenyl radical, this may be straight-chain or branched. It is preferably straight-chain and has from 2 to 10 carbon atoms. Accordingly, it is in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If R is an alkyl radical in which one $CH_2$ group has been replaced by —C— and one has been replaced by —CO—, these are preferably adjacent. These thus contain an acyloxy group —CO—O— or an oxycarbonyl group —O—CO—. These are preferably straight-chain and have from 2 to 6 carbon atoms.

Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If R is an alkyl or alkenyl radical which is monosubstituted by CN or $CF_3$, this radical is preferably straight-chain. The substitution by CN or $CF_3$ is in any desired position.

If R is an alkyl or alkenyl radical which is at least monosubstituted by halogen, this radical is preferably straight-chain, and halogen is preferably F or Cl. In the case of polysubstitution, halogen is preferably F. The resultant radicals also include perfluorinated radicals. In the case of monosubstitution, the fluorine or chlorine substituent may be in any desired position, but is preferably in the ω-position.

Compounds of the formula I containing branched wing groups R may occasionally be of importance owing to better solubility in the conventional liquid-crystalline base materials, but in particular as chiral dopants if they are optically active. Smectic compounds of this type are suitable as components of ferroelectric materials.

Compounds of the formula I having $S_A$ phases are suitable, for example, for thermally addressed displays.

Branched groups of this type generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexyloxy, 1-methylhexyloxy and 1-methylheptyloxy.

Y is preferably H, F, Cl, CN, $CF_3$, $CF_2H$, $OCF_3$, $OCF_2H$, $OCFHCF_3$, $OCFHCFH_2$, $OCFHCF_2H$, $OCF_2CH_3$, $OCF_2CFH_2$, $OCF_2CF_2H$, $OCF_2CF_2CF_2H$, $OCF_2CF_2CFH_2$, $OCFHCF_2CF_3$, $OCFHCF_2CF_2H$, $OCFHCFHCF_3$, $OCH_2CF_2CF_3$, $OCF_2CF_2CF_3$, $OCF_2CFHCFH_2$, $OCF_2CH_2CF_2H$, $OCFHCF_2CFH_2$, $OCFHCFHCF_2H$, $OCFHCH_2CF_3$, $OCH_2CFHCF_3$, $OCH_2CF_2CF_2H$, $OCF_2CFHCH_3$, $OCF_2CH_2CFH_2$, $OCFHCF_2CH3$, $OCFHCFHCFH_2$, $OCFHCH_2CF_3$, $OCH_2CF_2CFH_2$, $OCH_2CFHCF_2H$, $OCF_2CH_2CH_3$, $OCFHCFHCH_3$, $OCFHCH_2CFH_2$, $OCH_2CF_2CH_3$, $OCH_2CFHCFH_2$, $OCH_2CH_2CF_2H$, $OCHCH_2CH_3$, $OCH_2CFHCH_3$, $OCH_2CH_2CF_2H$, $OCClFCCIF_3$, $OCClFCClF_2$, $OCClFCFH_2$, $OCFHCCl_2F$, $OCClFCF_2H$, $OCClFCClF_2$, $OCF_2CClH_2$, $OCF_2CCl_2H$, $OCF_2CCl_2F$, $OCF_2CClFH$, $OCF_2CClF_2$, $OCF_2CF_2CClF_2$, $OCF_2CF_2CCl_2F$, $OCClFCF_2CF_3$, $OCClFCF_2CF_2H$, $OCClFCF_2CClF_2$, $OCClFCFHCF_3$, $OCClFCClFCF_3$, $OCCl_2CF_2CF_3$, $OCClHCF_2CF_3$, $OCClFCF_2CF_3$, $OCClFCClFCF_3$, $OCF_2CClFCFH_2$, $OCF_2CF_2CCl_2F$, $OCF_2CCl_2CF_2H$, $OCF_2CH_2CClF_2$, $OCClFCF_2CFH_2$, $OCFHCF_2CCl_2F$, $OCClFCFHCF_2H$, $OCClFCClFCF_2H$, $OCFHCFHCClF_2$, $OCClFCH_2CF_3$, $OCFHCCl_2CF_3$, $OCCl_2CFHCF_3$, $OCH_2CClFCF_3$, $OCCl_2CF_2CF_2H$, $OCH_2CF_2CClF_2$, $OCF_2CClFCH_3$, $OCF_2CFHCCl_2H$, $OCF_2CCl_2CFH_2$, $OCF_2CH_2CCl_2F$, $OCClFCF_2CH_3$, $OCFHCF_2CCl_2H$, $OCClFCClFCFH_2$, $OCFHCFHCCl_2F$, $OCClFCH_2CF_3$, $OCFHCCl_2CF_3$, $OCCl_2CF_2CFH_2$, $OCH_2CF_2CCl_2F$, $OCCl_2CFHCF_2H$, $OCClHCClFCF_2H$, $OCF_2CClHCClH_2$, $OCF_2CH_2CCl_2H$, $OCClFCFHCH_3$, $OCF_2CClFCCl_2H$, $OCClFCH_2CFH_2$, $OCFHCCl_2CFH_2$, $OCCl_2CF_2CH_3$, $OCH_2CF_2CClH_2$, $OCCl_2CFHCFH_2$, $OCH_2CClFCFCl_2$, $OCH_2CH_2CF_2H$, $OCClHCClHCF_2H$, $OCH_2CCl_2CF_2H$, $OCClFCH_2CH_3$, $OCFHCH_2CCl_2H$, $OCClHCFHCClH_2$, $OCH_2CFHCCl_2H$, $OCCl_2CH_2CF_2H$, $OCH_2CCl_2CF_2H$, $CH=CF_2$, $CF=CF_2$, $OCH=CF_2$, $OCF=CF_2$, $CH=CHF$, $OCH=CHF$, $CF=CHF$ or $OCF=CHF$, in particular H, F, Cl, CN, $CF_3$, $CF_2H$, $OCF_3$, $OCF_2H$, $OCFHCF_3$, $OCFHCFH_2$, $OCFHCF_2H$, $OCF_2CH_3$, $OCF_2CFH_2$, $OCF_2CF_2H$, $OCF_2CF_2CF_2H$, $OCF_2CF_2CFH_2$, $OCFHCF_2CF_3$, $OCFHCF_2CF_2H$, $OCF_2CF_2CF_3$, $OCF_2CHFCF_3$ or $OCClFCF_2CF_3$, very particularly preferably F or $OCF_3$.

Preference is also given to all compounds of the formula I and of all sub-formulae in which $A^1$ is a monosubstituted or disubstituted 1,4-phenylene. These are, in particular, 2-fluoro-1,4-phenylene, 3-fluoro-1,4-phenylene, 2,3-difluoro-1,4-phenylene and 2,6-difluoro-1,4-phenylene.

Preferred smaller groups of compounds of the formula I are those of the sub-formulae I1 to I27:

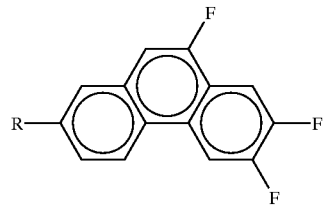 I1

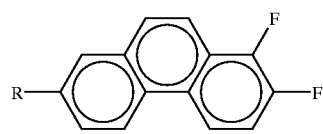 I2

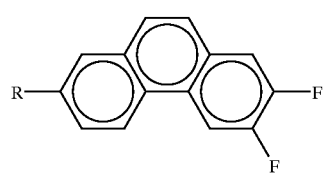 I3

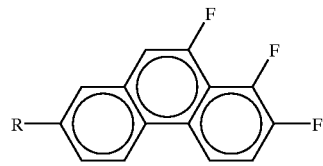 I4

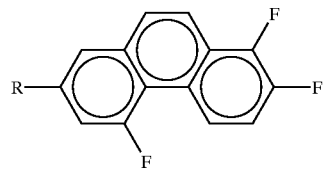 I5

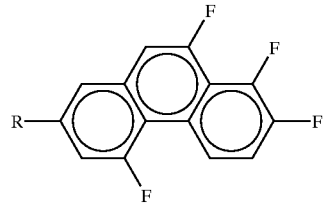 I6

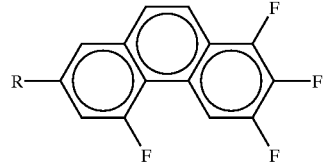 I7

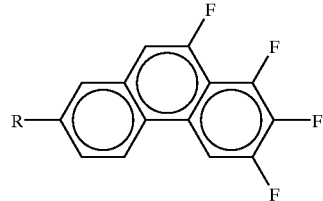 I8

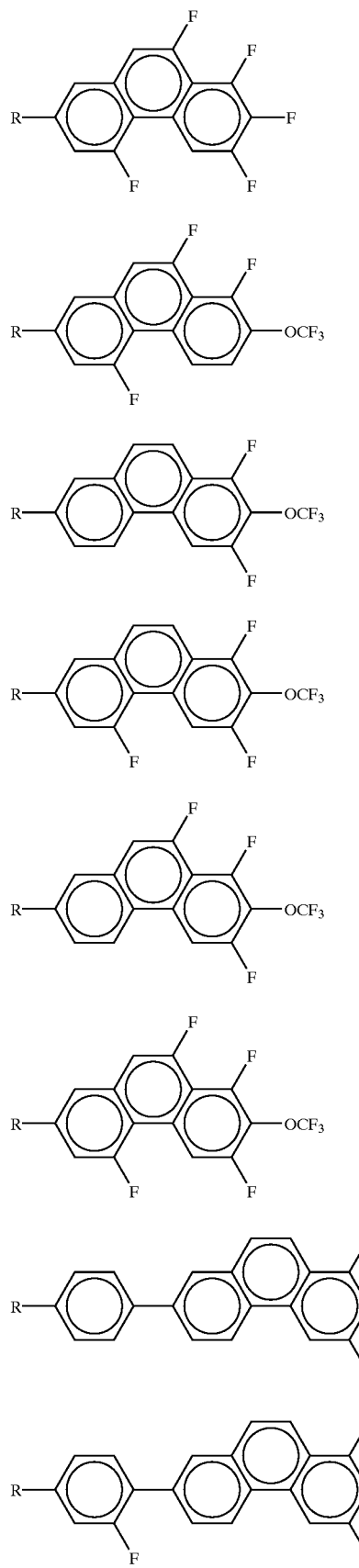
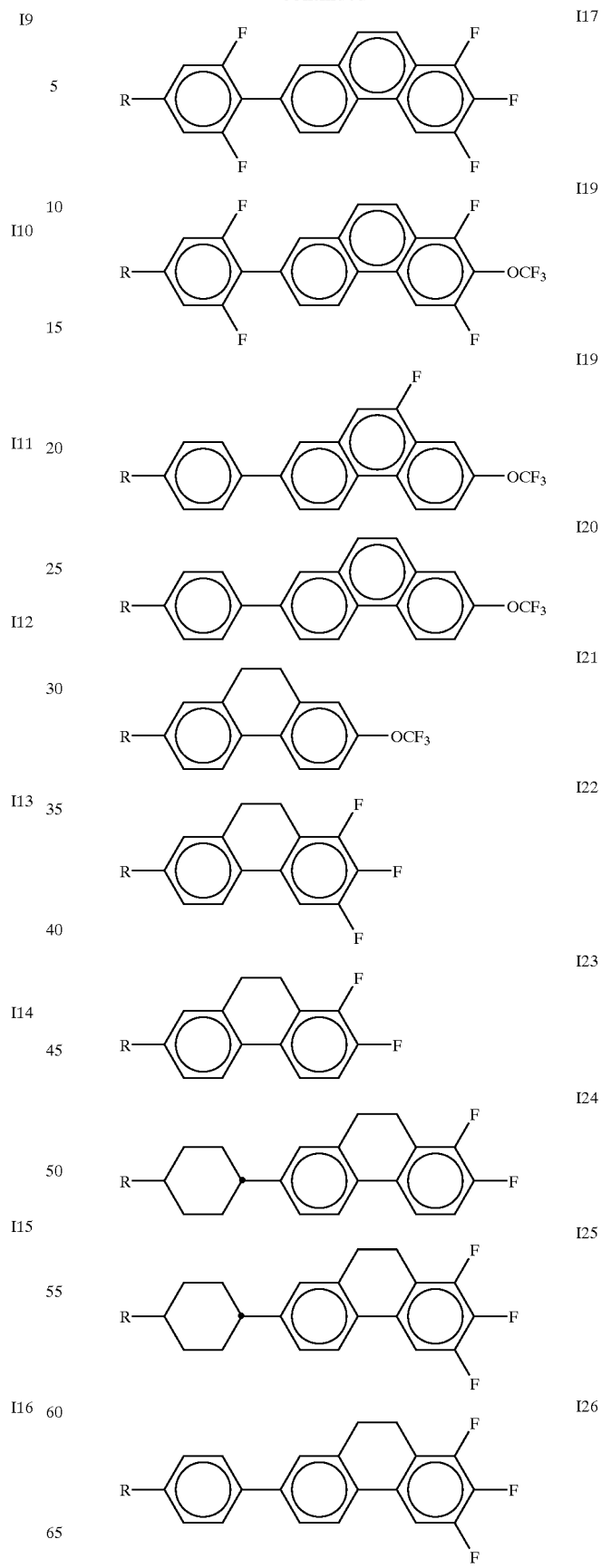

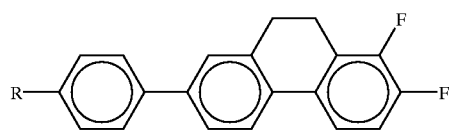

The compounds of the formula I are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

Scheme 1

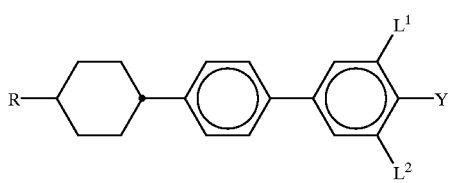

1. n-BuLi/THF/n-hexane
2. DMF
3. H⁺/H₂O

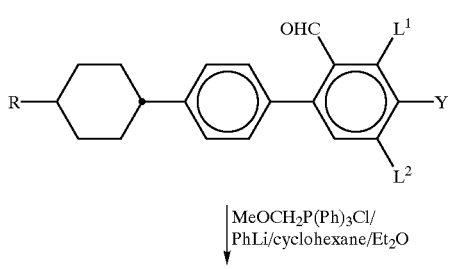

MeOCH₂P(Ph)₃Cl/
PhLi/cyclohexane/Et₂O

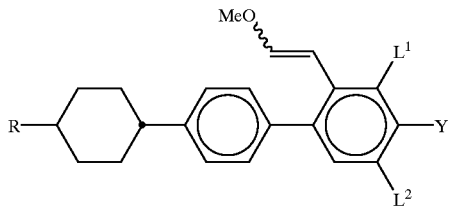

CH₃SO₃H/CH₂Cl₂

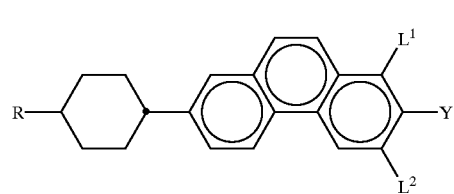

Scheme 2

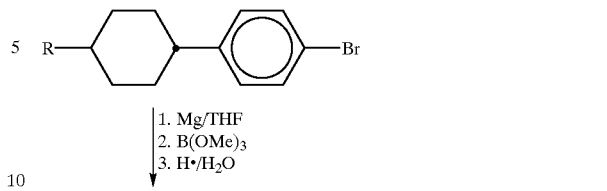

1. Mg/THF
2. B(OMe)₃
3. H•/H₂O

Pd/(PPh₃)₄/CsF/
DME

MeOCH₂P(Ph)₃Cl/
PhLi/cyclohexane/Et₂O

CH₃SO₃H/CH₂Cl₂

Scheme 3

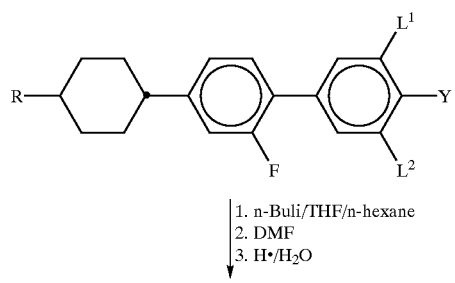

1. n-BuLi/THF/n-hexane
2. DMF
3. H•/H₂O

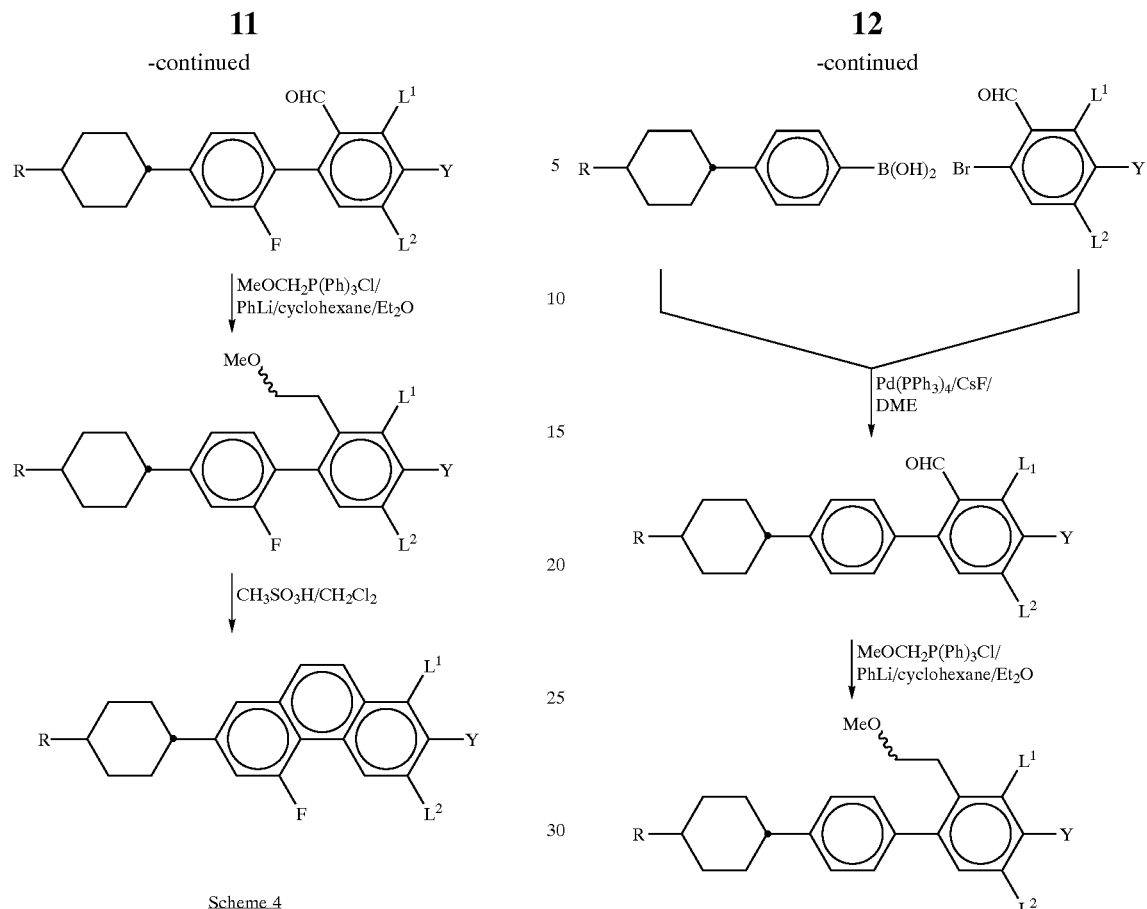
Scheme 4
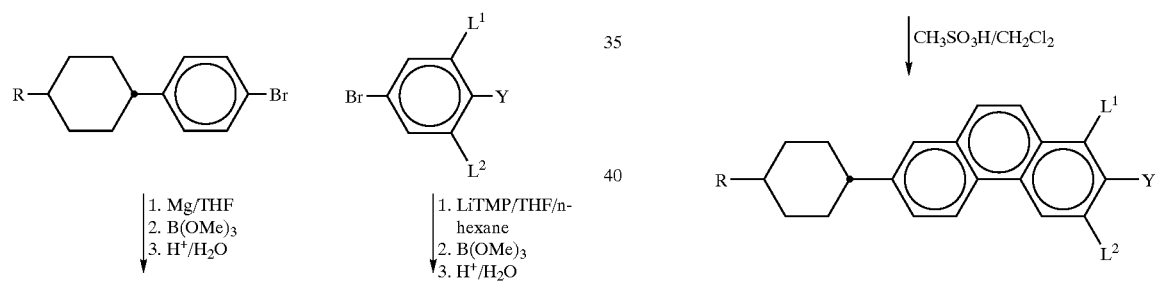
L = H or F
Scheme 5
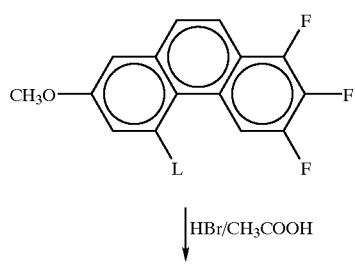
HBr/CH₃COOH

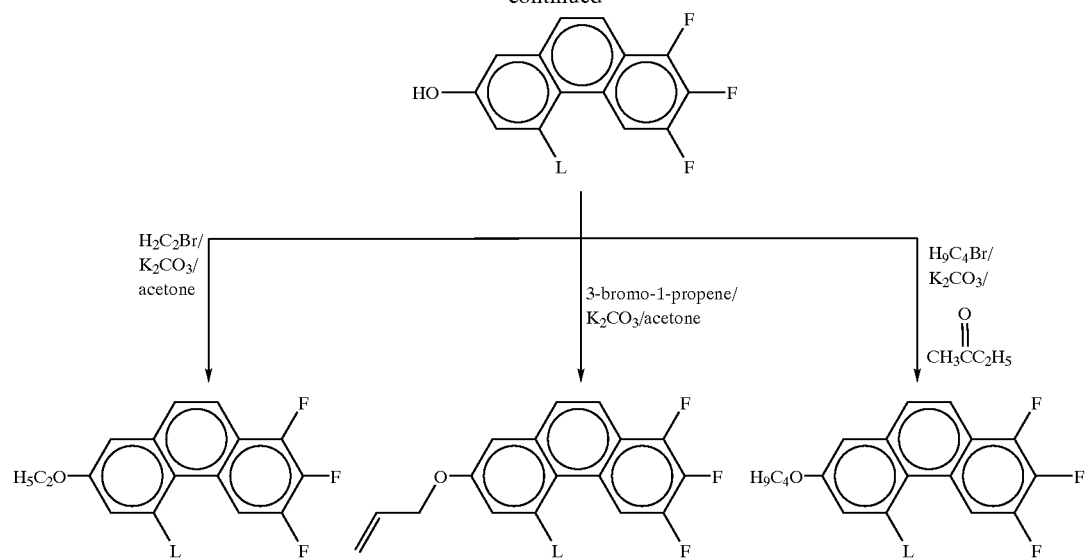
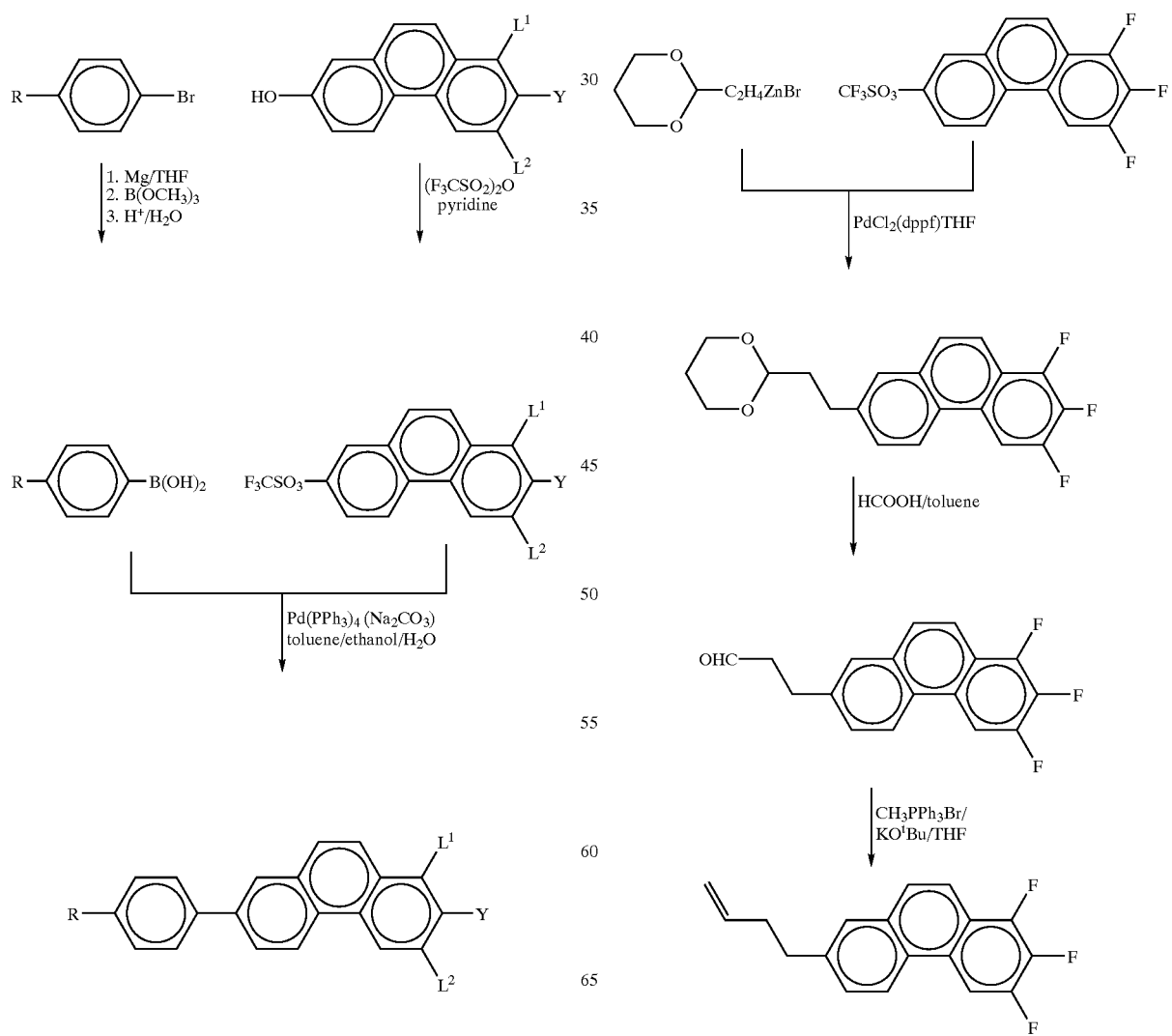

Scheme 8

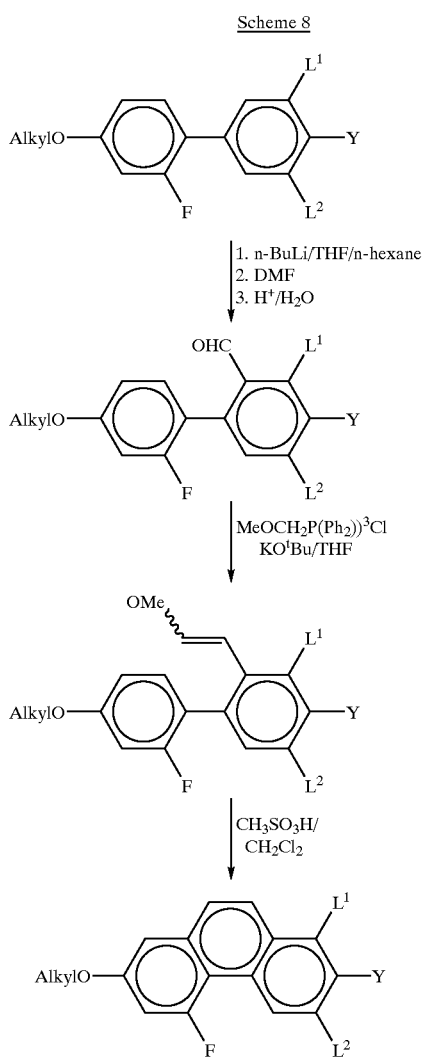

The invention also relates to electro-optical displays (in particular STN or MLC displays having two plane-parallel outer plates, which, together with a frame, form a cell, integrated non-linear elements for switching individual pixels on the outer plates, and a nematic liquid-crystal mixture of positive dielectric anisotropy and high specific resistance which is located in the cell) which contain media of this type, and to the use of these media for electro-optical purposes.

The liquid-crystal mixtures according to the invention enable a significant widening of the available parameter latitude.

The achievable combinations of clearing point, viscosity at low temperature, thermal and UV stability and dielectric anisotropy are far superior to previous materials from the prior art.

The requirement for a high clearing point, a nematic phase at low temperature and a high Δε has hitherto only been achieved to an inadequate extent. Although commercial liquid-crystal mixtures such as, for example, MLC-6847 (3.3 V driver) and MLC-13900-100 (5 V driver) (Merck KGaA, Darmstadt, Germany) have comparable clearing points and low-temperature stabilities, they have, however, much higher rotational viscosities $\gamma_1$.

The liquid-crystal mixtures according to the invention, while retaining the nematic phase down to −20° C. and preferably down to −30° C., particularly preferably down to −40° C., enable clearing points above 80° C., preferably above 90° C., particularly preferably above 100° C., simultaneously dielectric anisotropy values Δε of ≧4, preferably ≧6, and a low value for the rotational viscosity to be achieved, enabling excellent STN and MLC displays to be obtained. In particular, the mixtures are characterised by low operating voltages. The TN thresholds are below 1.5 V, preferably below 1.3 V, particularly preferably <1.0 V.

In particular owing to their relatively high optical anisotropy (Δn>0.16), the mixtures according to the invention are suitable for TFT applications with a low layer thickness. Use in p-Si applications (for example low layer thickness for projection displays) is furthermore possible.

It goes without saying that, through a suitable choice of the components of the mixtures according to the invention, it is also possible for higher clearing points (for example above 110°) to be achieved at higher threshold voltage or lower clearing points to be achieved at lower threshold voltages with retention of the other advantageous properties. At viscosities correspondingly increased only slightly, it is likewise possible to obtain mixtures having greater Δε and thus lower thresholds. The MLC displays according to the invention preferably operate at the first Gooch and Tarry transmission minimum [C. H. Gooch and H. A. Tarry, Electron. Lett. 10, 2–4,1974; C. H. Gooch and H. A. Tarry, Appi. Phys., Vol. 8, 1575–1584,1975] where, besides particularly favourable electro-optical properties, such as, for example, high steepness of the characteristic line and low angle dependence of the contrast (German Patent 30 22 818), a lower dielectric anisotropy is sufficient at the same threshold voltage as in an analogous display at the second minimum. This enables significantly higher specific resistances to be achieved using the mixtures according to the invention at the first minimum than in the case of mixtures comprising cyano compounds. Through a suitable choice of the individual components and their proportions by weight, the person skilled in the art is able to set the birefringence necessary for a pre-specified layer thickness of the MLC display using simple routine methods. In particular, use of the mixtures according to the invention in the Δn region >0.09 is preferred.

The flow viscosity $v_{20}$ of the mixtures according to the invention at 20° C. is preferably <60 mm$^2$·s$^{-1}$, particularly preferably <50 mm$^2$·s$^{-1}$. The nematic phase range is preferably at least 90', in particular at least 100°. This range preferably extends at least from −30° to +80°.

The values for the rotational viscosities of the mixtures according to the invention are preferably in the range from 100 to 200 mPa·s and are particularly preferably <130 mPa·s.

Measurements of the capacity holding ratio (HR) [S. Matsumoto et al., Liquid Crystals 5, 1320 (1989); K. Niwa et al., Proc. SID Conference, San Francisco, June 1984, p.304 (1984); G. Weber et al., Liquid Crystals 5, 1381 (1989)] have shown that mixtures according to the invention comprising compounds of the formula I exhibit a significantly smaller decrease in the HR with increasing temperature than analogous mixtures comprising cyanophenylcyclohexanes of the formula

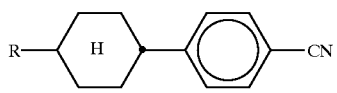

or esters of the formula

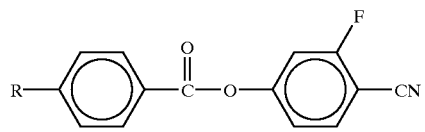

instead of the compounds of the formula I.

The UV stability of the mixtures according to the invention is also considerably better, i.e. they exhibit a significantly smaller decrease in the HR on exposure to UV.

The media according to the invention are preferably based on a plurality of (preferably two, three or more) compounds of the formula 1, i.e. the proportion of these compounds is 5–95%, preferably 10–60% and particularly preferably in the range 20–50%.

The individual compounds of the formulae I to IX and their sub-formulae which can be used in the media according to the invention are either known or they can be prepared analogously to the known compounds.

Preferred embodiments are indicated below:

Medium comprises compounds of the formula I in which R is preferably methyl, ethyl and/or propyl, furthermore butyl or pentyl. Compounds of the formula I having short side chains R have a positive effect on the elastic constants, in particular $K_1$, and result in mixtures having particularly low threshold voltages.

Medium additionally comprises one or more compounds selected from the group consisting of the general formulae II to IX:

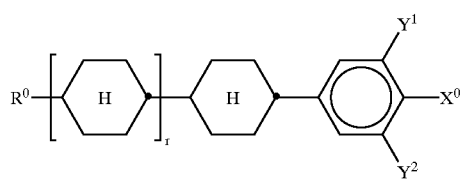

II

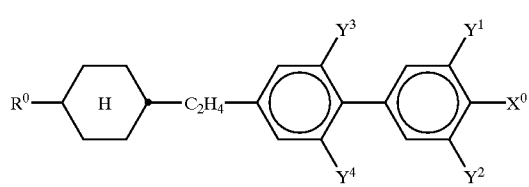

III

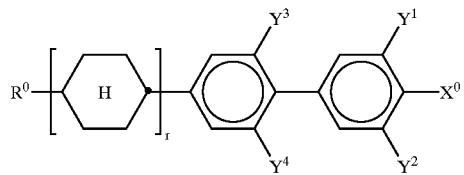

IV

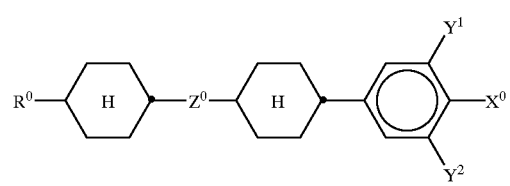

V

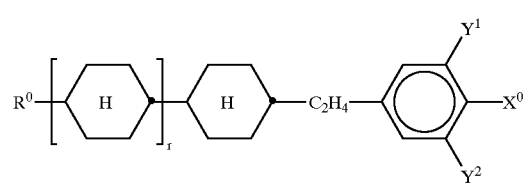

VI

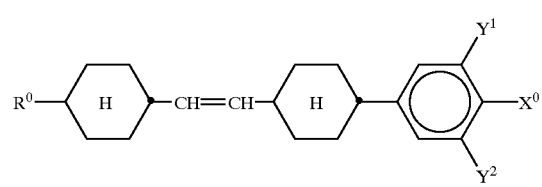

VII

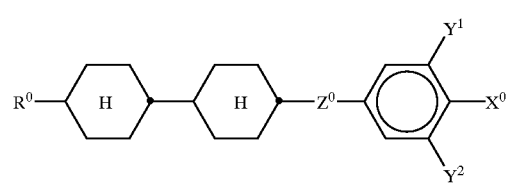

VIII

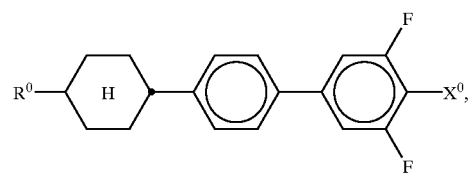

IX in which the individual radicals have the following meanings:

$R^0$ is n-alkyl, oxaalkyl, fluoroalkyl, alkenyloxy or alkenyl, each having up to 9 carbon atoms, $X^0$ is F, Cl, halogenated alkyl, alkenyl, alkenyloxy or alkoxy having up to 6 carbon atoms, $Z^0$ is —$C_2H_4$—, —$C_2F_4$—, —$CH_2O$—, —$OCH_2$—, —$CF_2O$—, —$OCF_2$— or —COO—, $Y^1$, $Y^2$, $Y^3$ and $Y^4$ are each, independently of one another, H or F, and r is 0, 1 or 2.

The compound of the formula IV is preferably

-continued

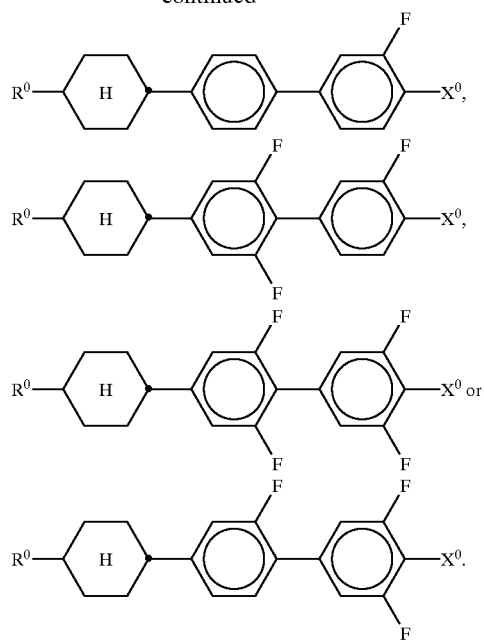

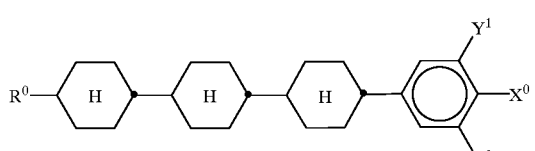

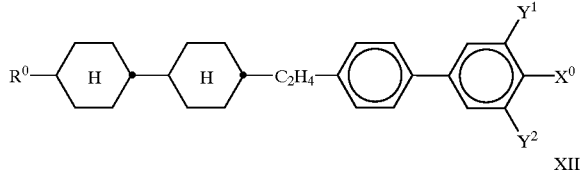

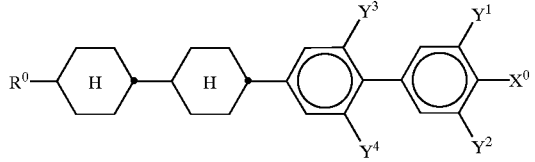

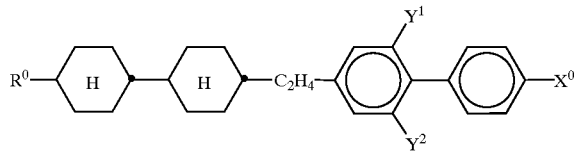

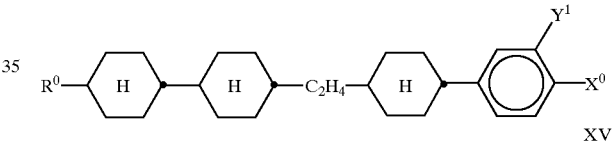

Medium additionally comprises one or more compounds of the formulae

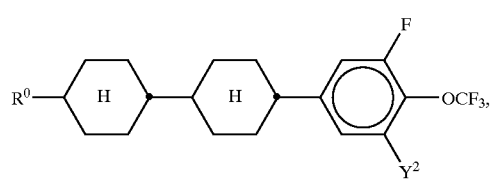

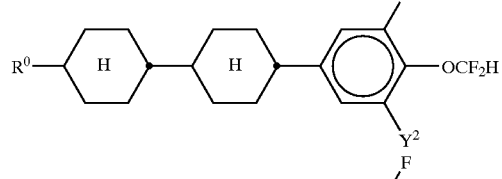

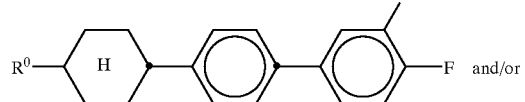 and/or

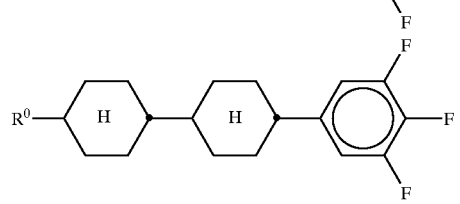

in which $R^0$ and $Y^2$ are as defined above.

Medium additionally comprises one or more compounds selected from the group consisting of the general formulae X to XVI:

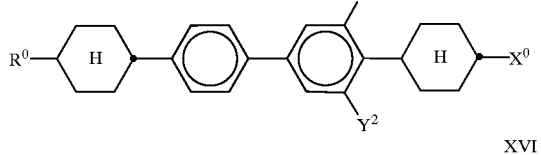

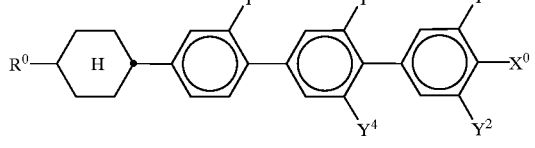

in which $R^0$, $X^0$, $Y^1$, $Y^2$, $Y^3$, $Y^4$ and $Y^5$ are each, independently of one another, as defined in claim 7. $X^0$ is preferably F, Cl, $CF_3$, $OCF_3$ or $OCHF_2$. $R^0$ is preferably alkyl, oxaalkyl, fluoroalkyl, alkenyl or alkenyloxy, each having up to 6 carbon atoms.

The proportion of compounds of the formulae I to IX together in the mixture as a whole is at least 50% by weight.

The proportion of compounds of the formula I in the mixture as a whole is from 5 to 50% by weight.

The proportion of compounds of the formulae II to IX in the mixture as a whole is from 30 to 70% by weight.

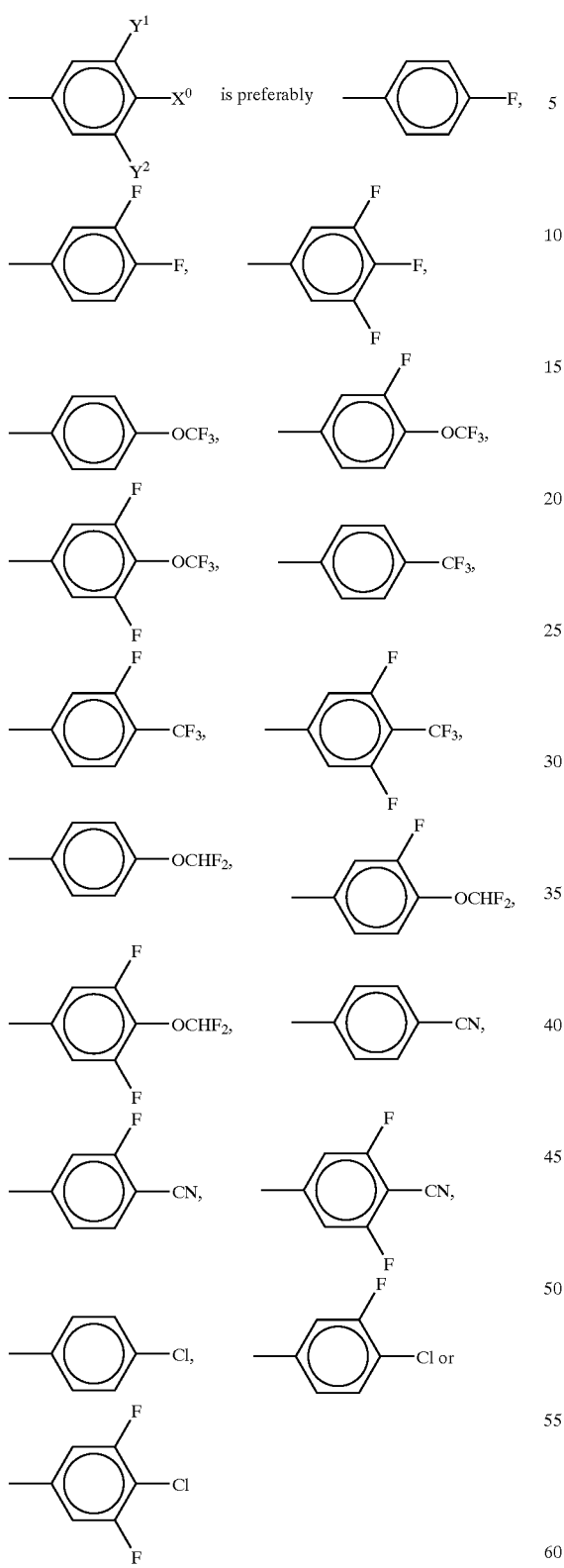

The medium comprises compounds of the formulae II, III, IV, V, VI, VII, VIII and/or IX.

$R^0$ is straight-chain alkyl or alkenyl having from 2 to 6 carbon atoms.

The medium essentially consists of compounds of the formulae I to XVI.

The medium preferably comprises four or more compounds from Table B.

The medium preferably comprises 3–10% by weight, in particular 5–8% by weight, of each homologue of the compounds of the formula I.

The medium comprises further compounds, preferably selected from the following group consisting of the general formulae XVII to XXII:

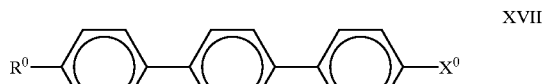

XVII

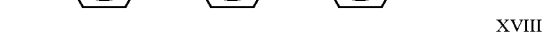

XVIII

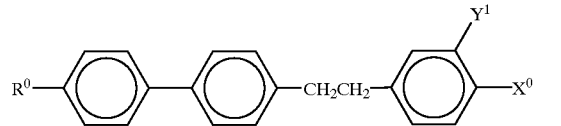

XIX

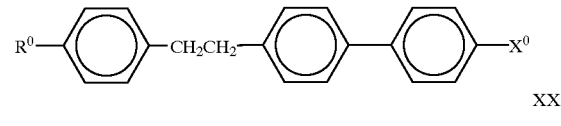

XX

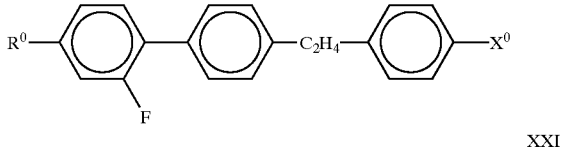

XXI

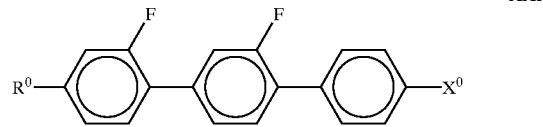

XXII in which $R^0$ and $X^0$ are as defined above, and the 1,4-phenylene rings may be substituted by CN, chlorine or fluorine. The 1,4-phenylene rings are preferably monosubstituted or polysubstituted by fluorine atoms.

The compounds of the formulae XVII to XXII are preferred co-components for mixtures according to the invention having a $\Delta n > 0.10$, in particular $> 0.15$.

The medium preferably comprises one, two, three or more ester compounds of the formulae E1 to E9:

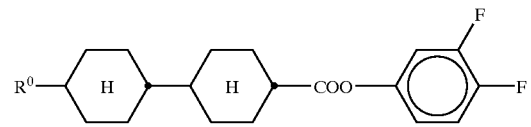

E1

-continued

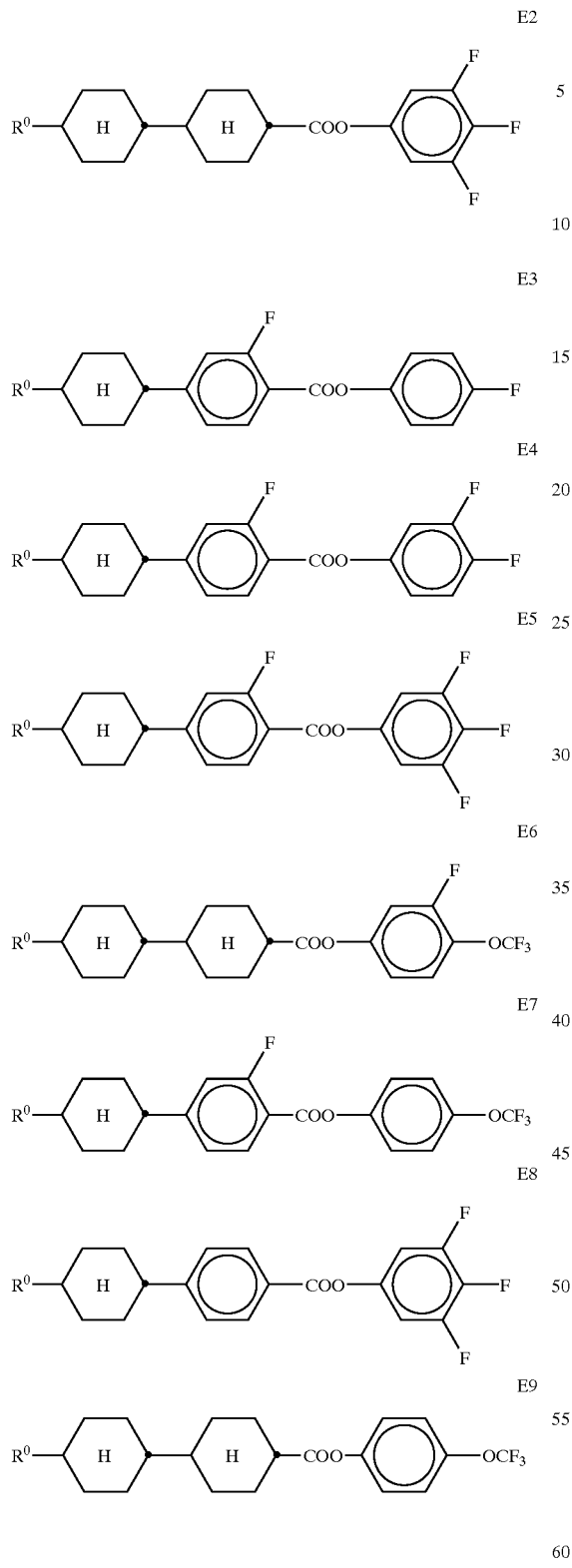

in which

R⁰ is as defined above.

The medium preferably comprises one or more dioxane compounds of the formulae D1 and/or D2

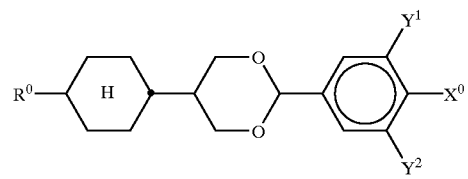

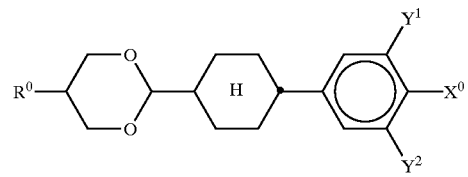

in which
R⁰, X⁰, Y¹ and Y² are as defined above. Y¹, Y² and X⁰ are preferably fluorine. Preference is furthermore given to dioxane compounds in which X⁰ is OCF₃, Y¹ is fluorine and Y² is fluorine or hydrogen.

The medium optionally comprises further compounds, preferably selected from the following group consisting of the formulae RI to RVIII:

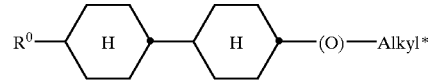

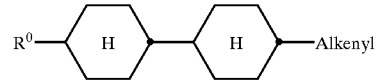

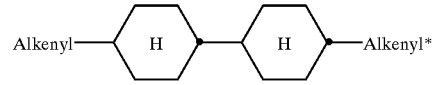

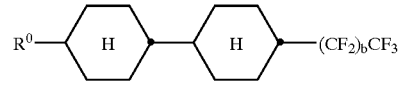

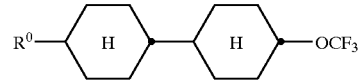

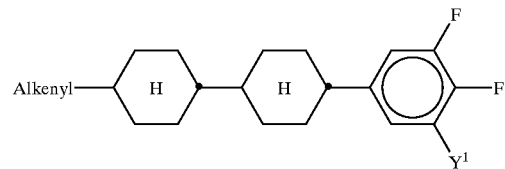

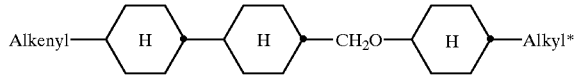

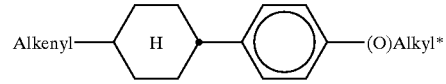

in which
R⁰ is n-alkyl, oxaalkyl, fluoroalkyl, alkenyloxy or alkenyl, each having up to 9 carbon atoms, b is 0, 1 or 2,
$Y^1$ is H or F,
Alkyl and Alkyl*
   are each, independently of one another, a straight-chain alkyl radical having up to 9 carbon atoms, and
Alkenyl and Alkenyl*
   are each, independently of one another, an alkenyl radical having up to 9 carbon atoms.

The medium preferably comprises one or more compounds of the formula

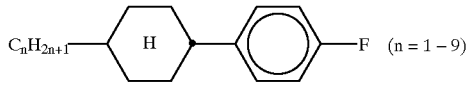  (n = 1 – 9)

The medium preferably comprises one or more compounds of the formulae

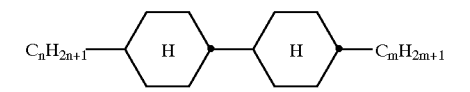 RIa

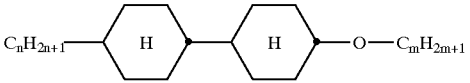 RIb

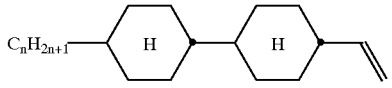 RIIa

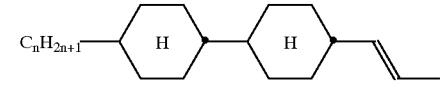 RIIb

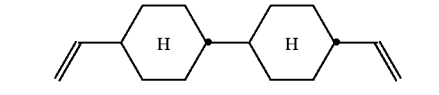 RIIIa

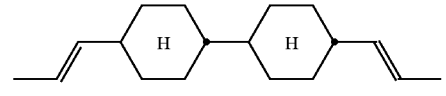 RIIIb

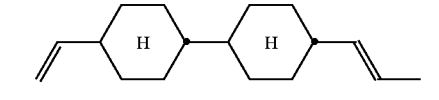 RIIIc

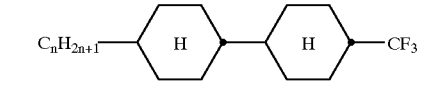 RIVa in which n and m are each an integer from 1 to 9.

The I: (II+III+IV+V+VI+VII+VIII+IX) weight ratio is preferably from 1:10 to 10:1.

The medium essentially consists of compounds selected from the group consisting of the general formulae I to XV.

It has been found that even a relatively small proportion of compounds of the formula I mixed with conventional liquid-crystal materials, but in particular with one or more compounds of the formulae II, III, IV, V, VI, VII, VIII and/or IX, results in a significant lowering of the threshold voltage and in low values of the rotational viscosity $\gamma_1$, with broad nematic phases with low smectic-nematic transition temperatures being observed at the same time, improving the shelf life. The compounds of the formulae I to IX are colourless, stable and readily miscible with one another and with other liquid-crystal materials.

The term "Alkyl" or "Alkyl*" in the co-components covers straight-chain and branched alkyl groups having 1–9 carbon atoms, in particular the straight-chain groups methyl, ethyl, propyl, butyl, pentyl, hexyl and heptyl. Groups having 2–5 carbon atoms are generally preferred.

The term "Alkenyl" or "Alkenyl*" in the co-components covers straight-chain and branched alkenyl groups having up to 9 carbon atoms, in particular the straight-chain groups. Particularly preferred alkenyl groups are $C_2$–$C_7$-1E-alkenyl, $C_4$–$C_7$-3E-alkenyl, $C_5$–$C_7$-4-alkenyl, $C_6$–$C_7$-5-alkenyl and $C_7$-6-alkenyl, in particular $C_2$–$C_7$-1E-alkenyl, $C_4$–$C_7$-3E-alkenyl and $C_5$–$C_7$-4-alkenyl. Examples of preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexeryl, 4Z-heptenyl, 5-hexenyl, 6-heptenyl and the like. Groups having up to 5 carbon atoms are generally preferred.

The term "fluoroalkyl" preferably covers straight-chain groups having a terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" preferably covers straight-chain radicals of the formula $C_nH_{2n+1}$—O—$(CH_2)_m$, in which n and m are each, independently of one another, from 1 to 6. n is preferably=1 and m is preferably from 1 to 6.

Through a suitable choice of the meanings of $R^0$ and $X^0$, the addressing times, the threshold voltage, the steepness of the transmission characteristic lines, etc., can be modified in the desired manner. For example, 1E-alkenyl radicals, 3E-aikenyl radicals, 2E-alkenyloxy radicals and the like generally result in shorter addressing times, improved nematic tendencies and a higher ratio of the elastic constants $k_{33}$ (bend) and $k_{11}$ (splay) compared with alkyl or alkoxy radicals. 4-Alkenyl radicals, 3-alkenyl radicals and the like generally give lower threshold voltages and smaller values of $k_{33}/k_{11}$ compared with alkyl and alkoxy radicals.

A —$CH_2CH_2$— group in $Z^1$ generally results in higher values of $k_{33}/k_{11}$ compared with a single covalent bond. Higher values of $k_{33}/k_{11}$ facilitate, for example, flatter transmission characteristic lines in TN cells with a 90° twist (in order to achieve grey shades) and steeper transmission characteristic lines in STN, SBE and OMI cells (greater multiplexability), and vice versa.

The optimum mixing ratio of the compounds of the formulae I and II+III+IV+V+VI+VII+VII+IX depends substantially on the desired properties, on the choice of the components of the formulae I, II, III, IV, V, VI, VII, VIII and/or IX, and on the choice of any other components that may be present. Suitable mixing ratios within the range given above can easily be determined from case to case.

The total amount of compounds of the formulae I to XV in the mixtures according to the invention is not crucial. The mixtures can therefore comprise one or more further components for the purposes of optimising various properties. However, the observed effect on the addressing times and the threshold voltage is generally greater, the higher the total concentration of compounds of the formulae I to XV.

In a particularly preferred embodiment, the media according to the invention comprise compounds of the formulae II to IX (preferably II and/or III) in which $X^0$ is $OCF_3$, $OCHF_2$, F, $OCH=CF_2$, $OCF=CF_2$, $OCF_2CHFCF_3$ or $OCF_2$—$CF_2H$. A favourable synergistic effect with the compounds of the formula I results in particularly advantageous properties.

The construction of the MLC display according to the invention from polarisers, electrode base plates and surface-treated electrodes corresponds to the conventional construction for displays of this type. The term "conventional construction" is broadly defined here and also covers all derivatives and modifications of the MLC display, in particular including matrix display elements based on poly-Si TFT or MIM.

A significant difference between the displays according to the invention and the conventional displays based on the twisted nematic cell consists, however, in the choice of the liquid-crystal parameters of the liquid-crystal layer.

The liquid-crystal mixtures which can be used in accordance with the invention are prepared in a manner which is conventional per se. In general, the desired amount of the components used in the lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing.

The dielectrics may also comprise further additives known to the person skilled in the art and described in the literature, such as, for example, UV stabilisers, antioxidants, as mentioned, for example, in Table D. Furthermore, 0–15% of pleochroic dyes or chiral dopants may be added to the mixture.

C denotes a crystalline phase, S a smectic phase, $S_c$ a smectic C phase, N a nematic phase and I the isotropic phase.

$V_{10}$ denotes the voltage for 10% transmission (viewing angle perpendicular to the plate surface). $t_{on}$ denotes the switch-on time and $t_{off}$ the switch-off time at an operating voltage corresponding to 2.0 times the value of $V_{10}$. $\Delta n$ denotes the optical anisotropy and no the refractive index. $\Delta\epsilon$ denotes the dielectric anisotropy ($\Delta\epsilon=\epsilon_\parallel-\epsilon_\perp$, where $\epsilon_\parallel$ denotes the dielectric constant parallel to the longitudinal molecular axes and $\epsilon_\perp$ denotes the dielectric constant perpendicular thereto). The electro-optical data were measured in a TN cell at the 1st minimum (i.e. at a d·Δn value of 0.5 μm) at 20° C., unless expressly stated otherwise. The optical data were measured at 20° C., unless expressly stated otherwise.

In the present application and in the examples below, the structures of the liquid-crystal compounds are indicated by means of acronyms, the transformation into chemical formulae taking place in accordance with Tables A and B below. All radicals $C_nH_{2n+1}$ and $C_mH_{2m+1}$ are straight-chain alkyl radicals having n and m carbon atoms respectively. The coding in Table B is self-evident. In Table A, only the acronym for the parent structure is indicated. In individual cases, the acronym for the parent structure is followed, separated by a dash, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nF.F.F | $C_nH_{2n+1}$ | F | F | F |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_2H_{2s}$— | CN | H | H |
| nAm | $C_nH_{2n+1}$ | $COOC_mH_{2m+1}$ | H | H |
| nOCCF$_2$.F.F | $C_nH_{2n+1}$ | $OCH_2CF_2H$ | F | F |

Preferred mixture components are shown in Tables A and B.

TABLE A

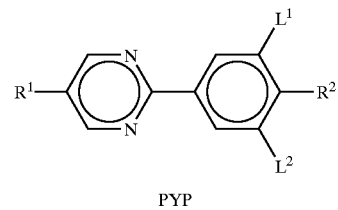

PYP

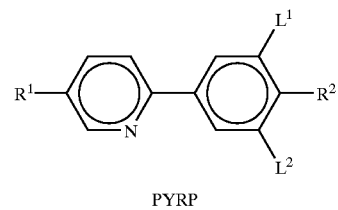

PYRP

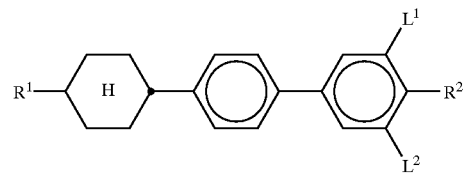

BCH

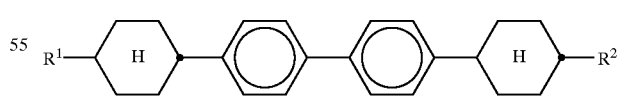

CBC

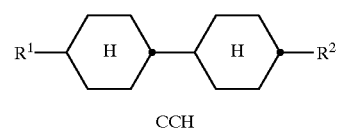

CCH

TABLE A-continued
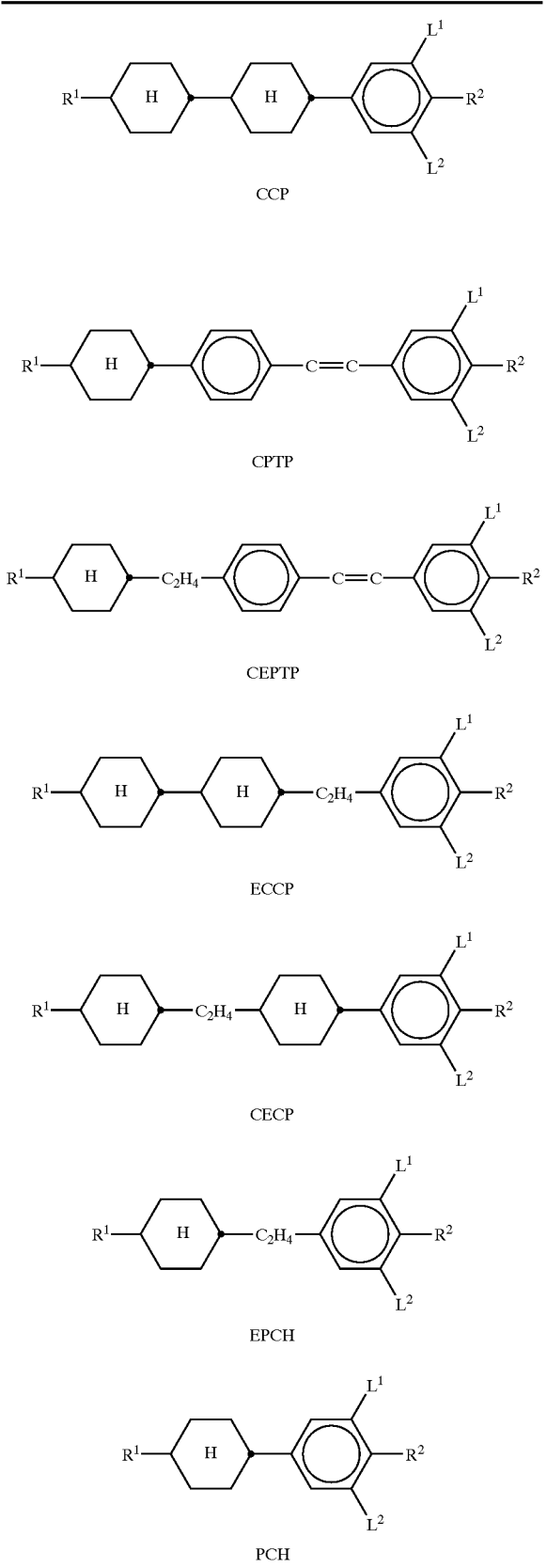
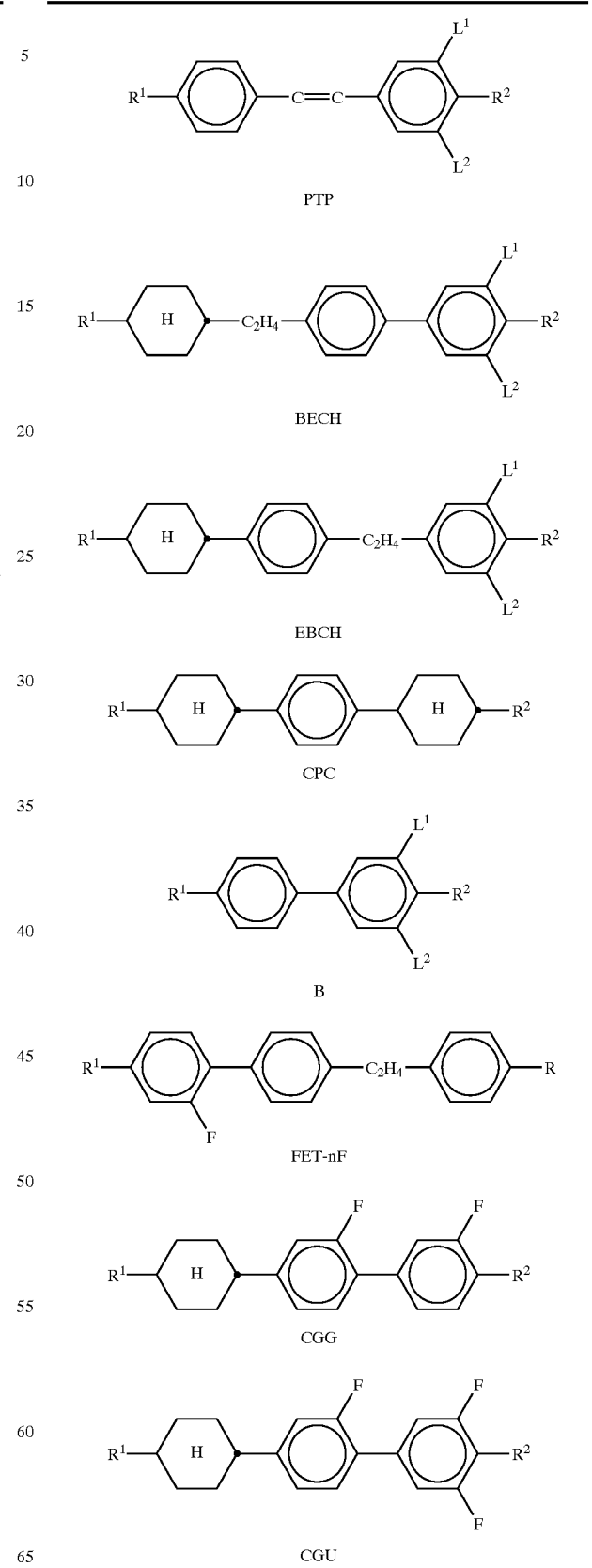

TABLE A-continued
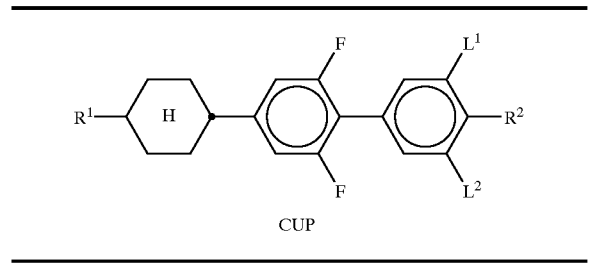
CUP
TABLE B
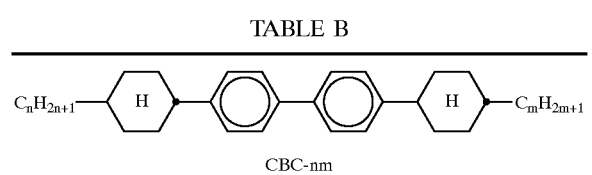
CBC-nm
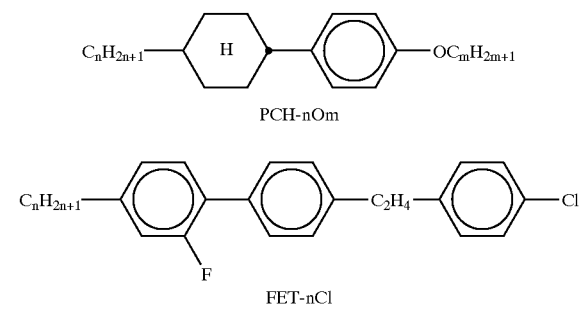
PCH-nOm
FET-nCl
CP-nOCF₃
CCH-nOm
BCH-n·Fm
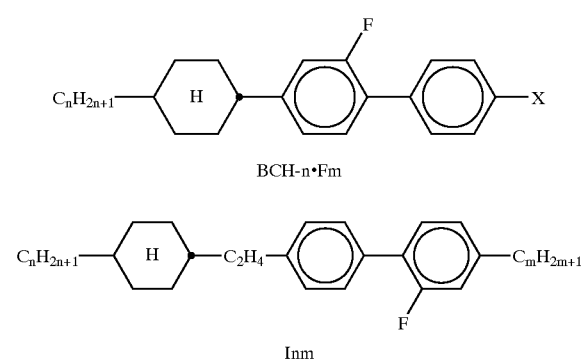
Inm
CBC-nmF
TABLE B-continued
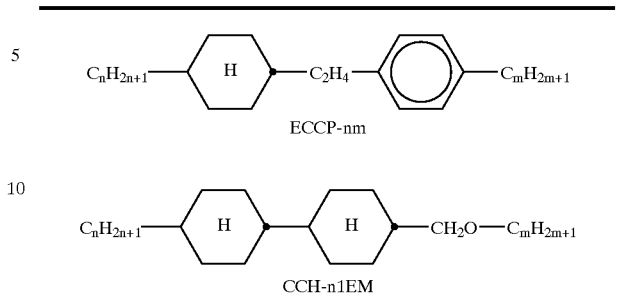
ECCP-nm
CCH-n1EM
T-nFm
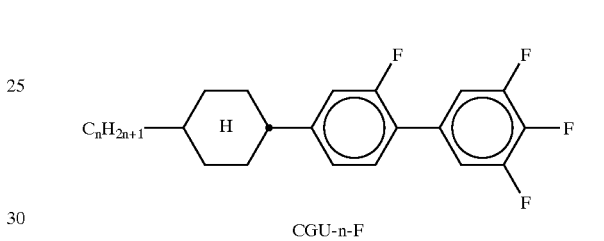
CGU-n-F
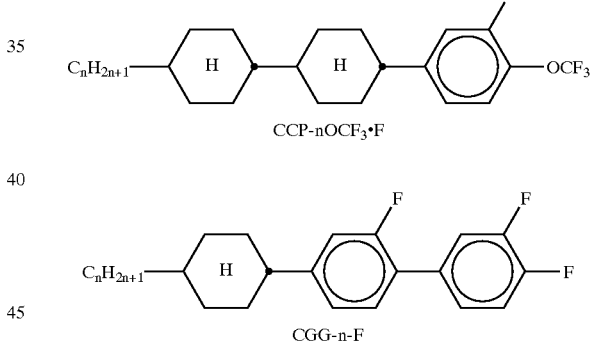
CCP-nOCF₃·F
CGG-n-F
CCP-nOCF₂·F·(F)
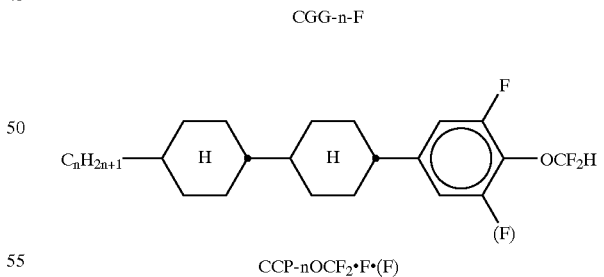
CCP-nF·F·F TABLE B-continued CGU-n-O1DT CCZU-n-F CC-n-V1

CC-n-V

CCP-nOCF3

BCH-nF·F·F

CGZU-n-F

CCP-nF·F

CUZP-n-F

TABLE B-continued

CGU-1V-F

CCG-V-F

CGZP-n-F

CUZP-n-OT

GGP-n-Cl

PGIGI-n-F

CCQU-n-F

Dec-U-n-F

TABLE B-continued
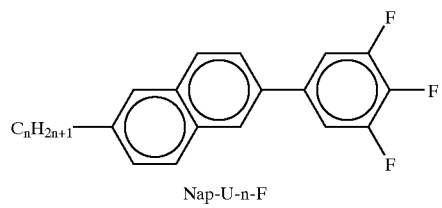
Nap-U-n-F
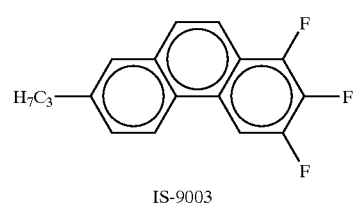
IS-9003
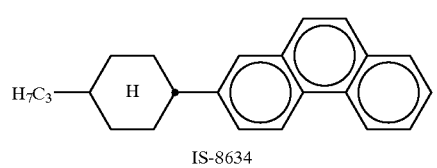
IS-8634
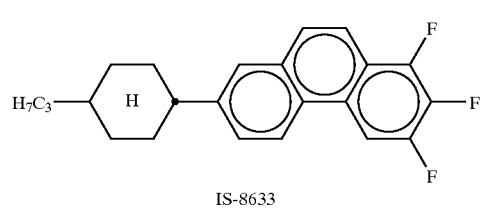
IS-8633
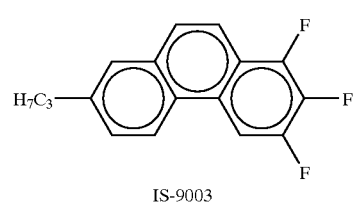
IS-9003
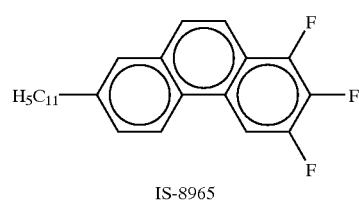
IS-8965
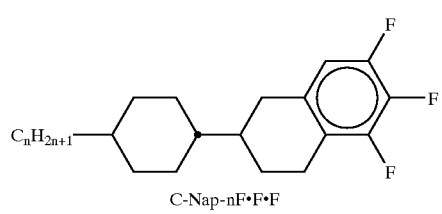
C-Nap-nF•F•F
TABLE B-continued
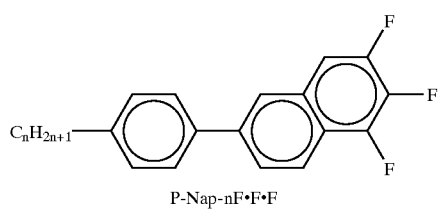
P-Nap-nF•F•F
TABLE C
Table C indicates possible dopants which are generally added to the mixtures according to the invention.
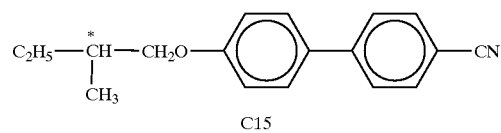
C15
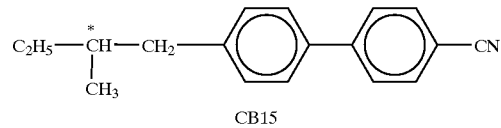
CB15
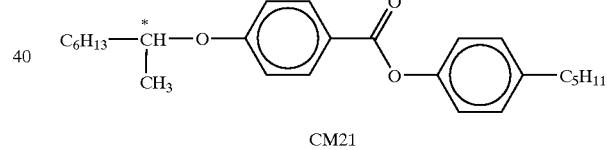
CM21
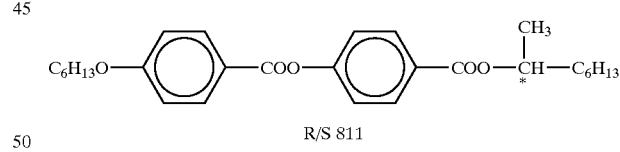
R/S 811
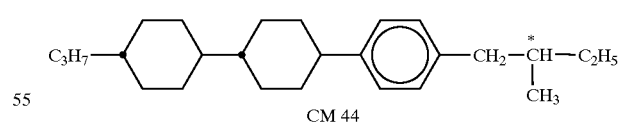
CM 44
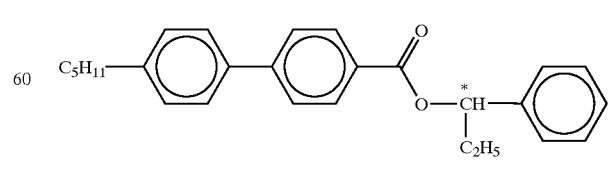
CM 45

TABLE C-continued
Table C indicates possible dopants which are generally added to the mixtures according to the invention.
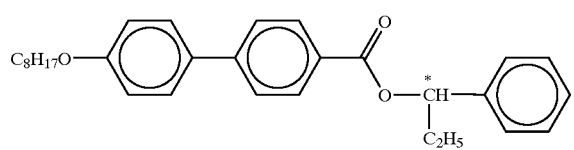
CM 47
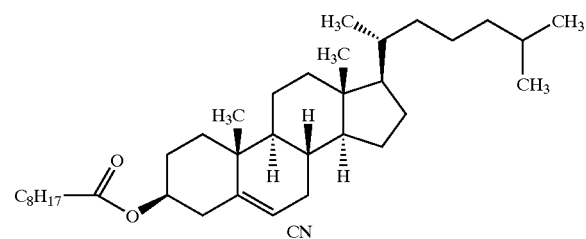
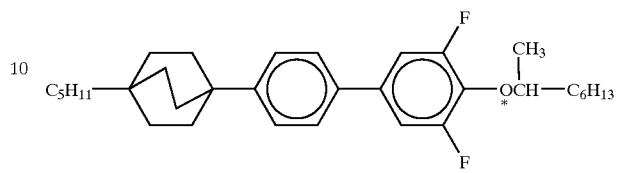
R/S 4011
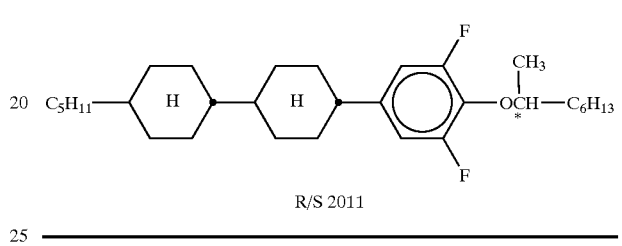
R/S 2011
TABLE D
Stabilisers which, for example, can be added to the mixtures according to the invention are indicated below.
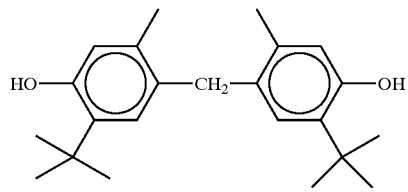
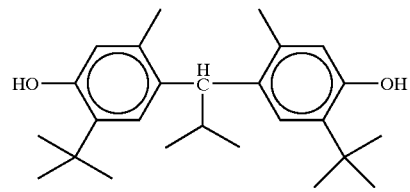
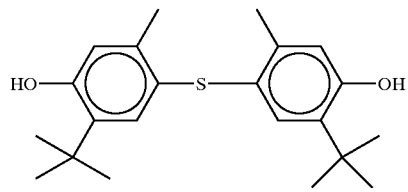
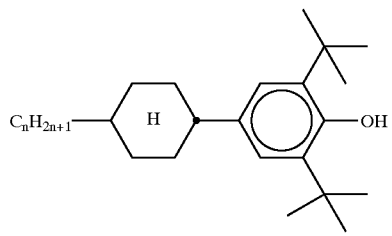
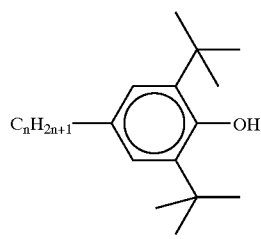
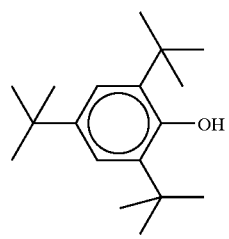

TABLE D-continued
Stabilisers which, for example, can be added to the mixtures according to the invention are indicated below.
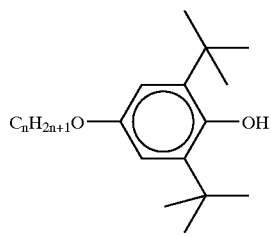
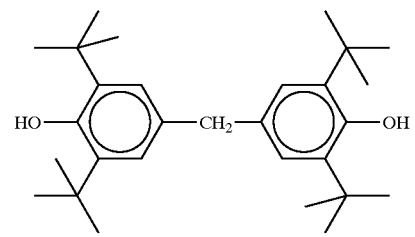
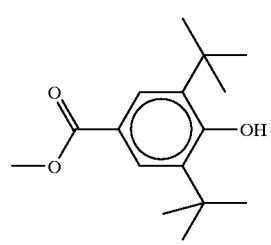
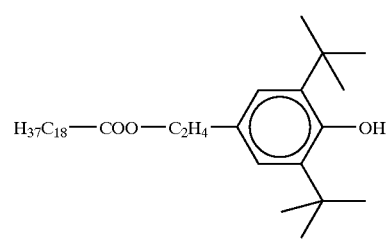
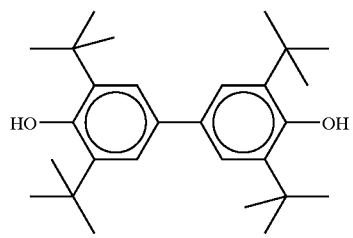
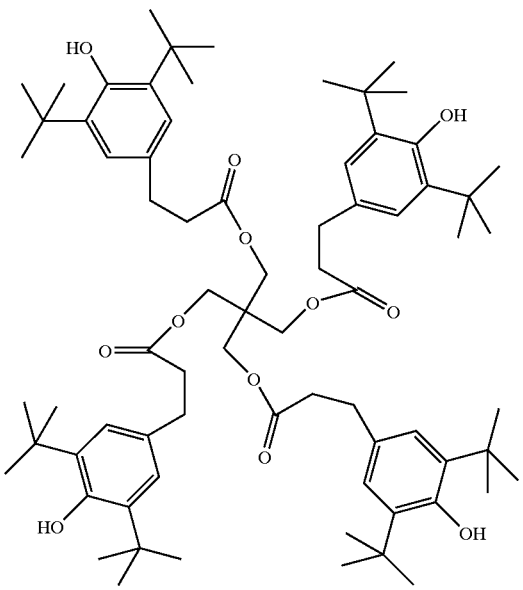
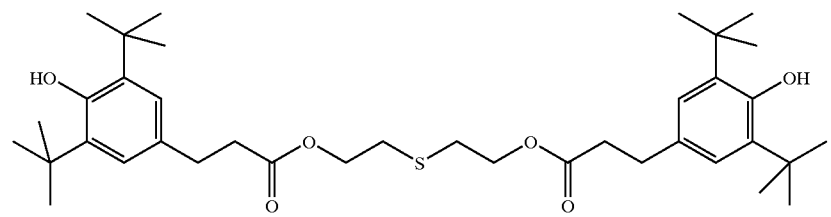

TABLE D-continued
Stabilisers which, for example, can be added to the mixtures according to the invention are indicated below.
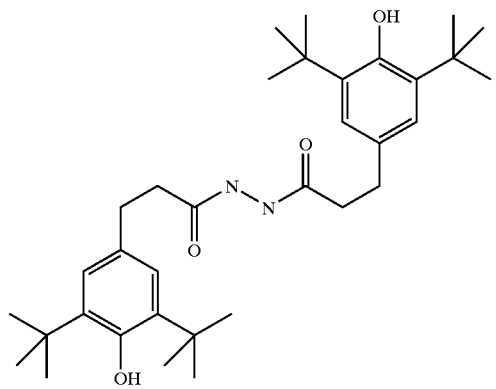
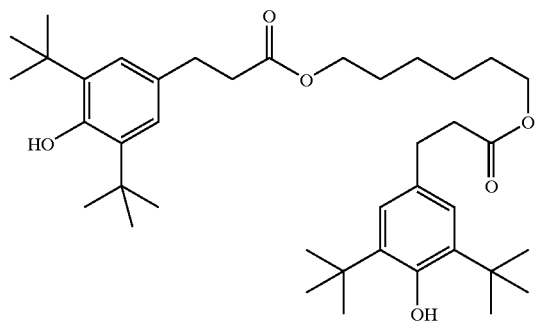
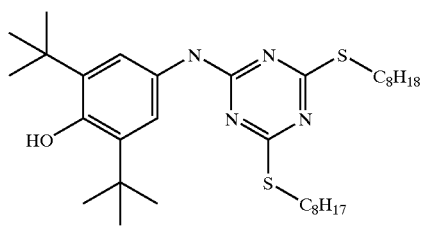
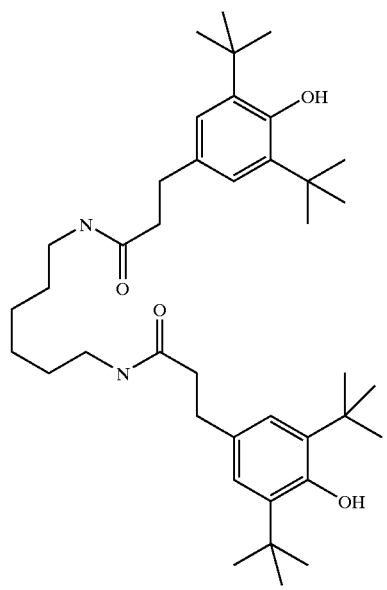
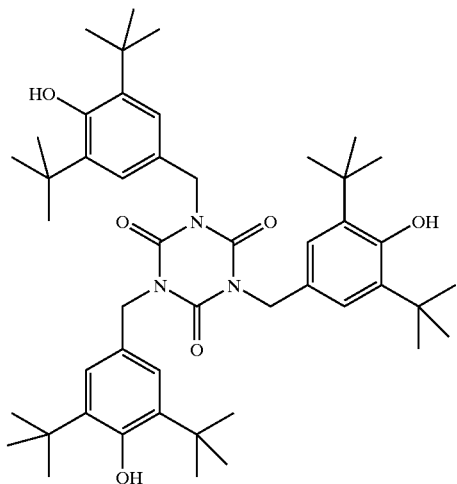
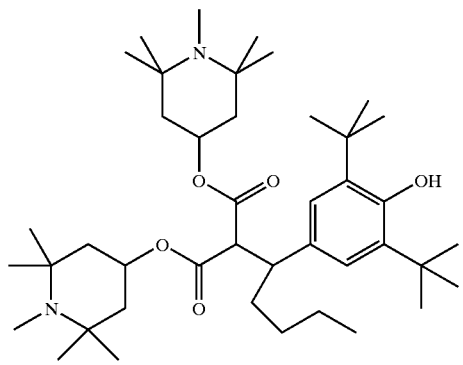

TABLE D-continued
Stabilisers which, for example, can be added to the mixtures according to the invention are indicated below.
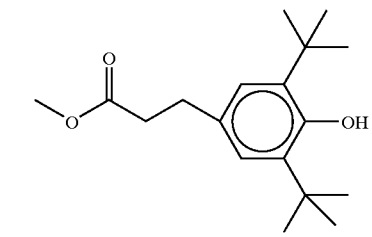
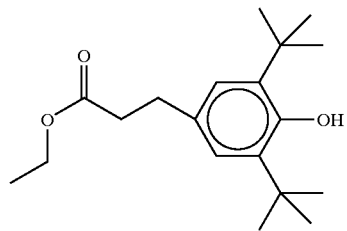
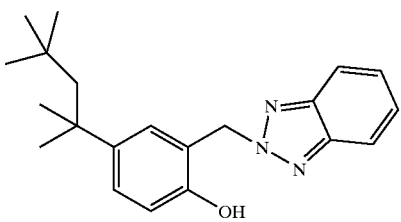
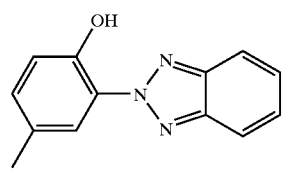
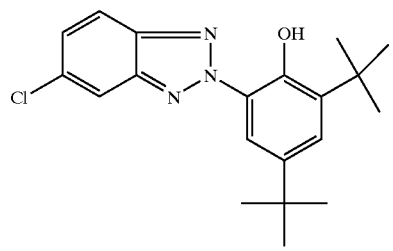
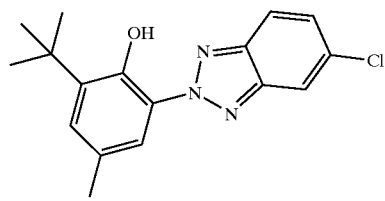
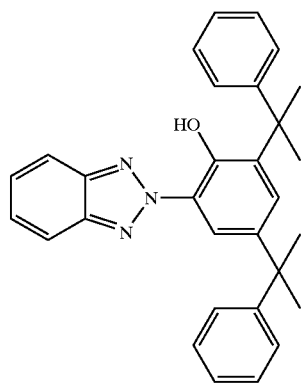
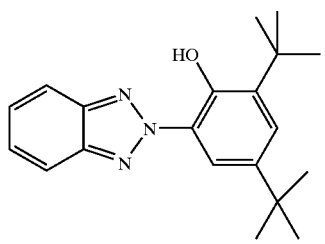
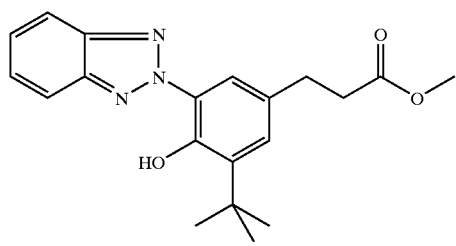
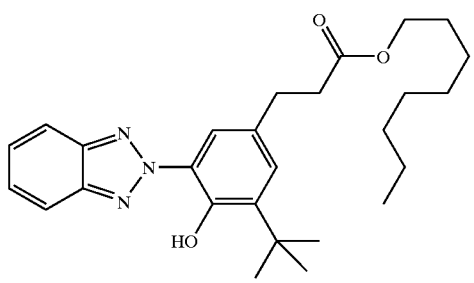

TABLE D-continued

Stabilisers which, for example, can be added to the mixtures according to the invention are indicated below.

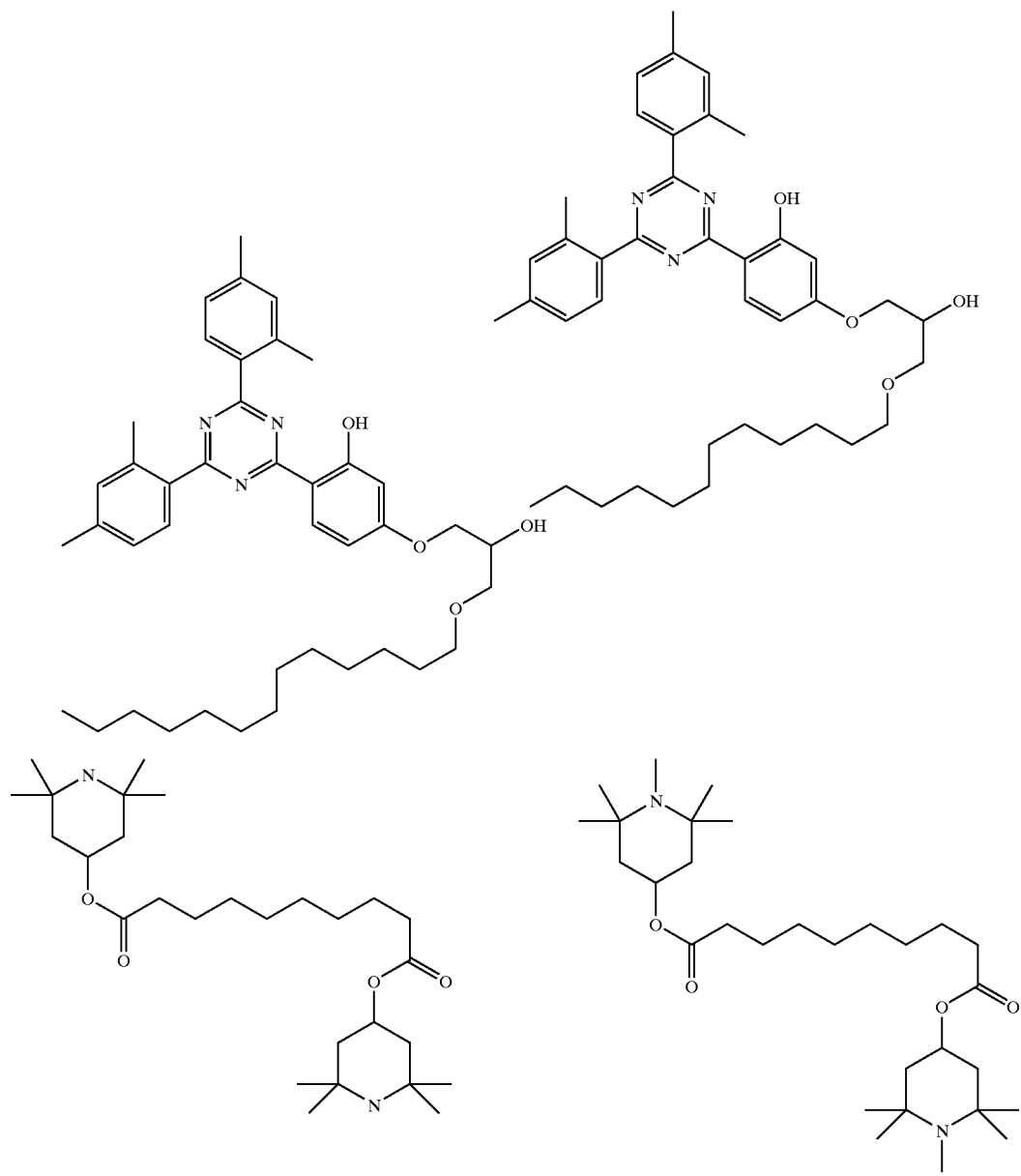

The following examples are intended to explain the invention without restricting it. Above and below, percentages are percent by weight. All temperatures are given in degrees Celsius. m.p. denotes melting point, cl.p. denotes clearing point. Furthermore, C=crystalline state, N=nematic phase, S=smectic phase and I=isotropic phase. The data between these symbols represent the transition temperatures. $\Delta n$ denotes optical anisotropy (589 nm, 20° C.), the flow viscosity V20 (mm²/sec) was determined at 20° C. The rotational viscosity $\gamma_1$ (mPa·s) was likewise determined at 20° C.

"Conventional work-up" means that water is added if necessary, the mixture is extracted with dichloromethane, diethyl ether, methyl tert-butyl ether or toluene, the phases are separated, the organic phase is dried and evaporated, and the product is purified by distillation under reduced pressure or crystallisation and/or chromatography. The following abbreviations are used:

| | |
|---|---|
| n-BuLi | 1.6 molar solution of n-butyllithium in n-hexane |
| DMAP | 4-(dimethylamino)pyridine |
| THF | tetrahydrofuran |
| DCC | N,N'-dicyclohexylcarbodiimide |

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLE 1

Step 1.1

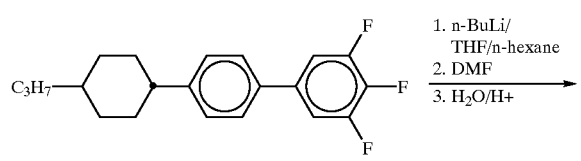

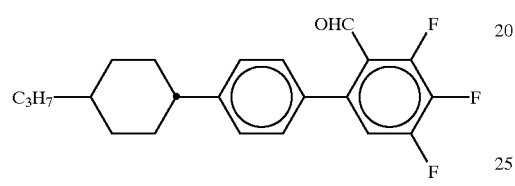

A solution of 46 mmol of 3,4,5-trifluoro-4'-(4-propylcyclohexyl)biphenyl in 100 ml of dry tetrahydrofuran is cooled to −75° C., and 50 mmol of n-butyllithium (1.6 M solution in n-hexane) are added dropwise under a protective-gas atmosphere at such a rate that the internal temperature does not exceed −75° C. The mixture is subsequently stirred at this temperature for a further 2 hours. 60 mmol of N,N-dimethylformamide are then likewise added dropwise at such a rate that the internal temperature always remains below −75° C. When the addition is complete, the reaction solution is allowed to thaw slowly and is hydrolysed at −10° C. by transfer of the reaction solution into ice-water. The mixture is acidified using hydrochloric acid (pH=3) and extracted with tert-butyl methyl ether. The combined organic extracts are washed with water and saturated sodium chloride solution and dried using sodium sulfate. After the solvent has been removed under reduced pressure, the crude product is chromatographed on silica gel with dichloromethane/n-heptane 1:1 as eluent, giving 3,4,5-trifluoro-4'-(4-propylcyclohexyl)biphenyl-2-carbaldehyde in the form of slightly yellowish crystals; m.p. 62° C.

Step 1.2

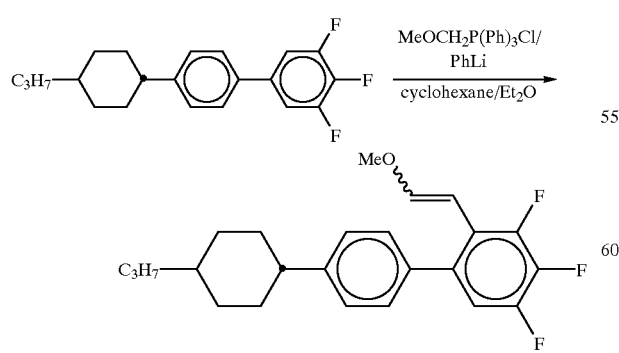

27 ml (48 mmol) of a 1.8 M solution of phenyllithium in cyclohexane/diethyl ether (7:3) are added dropwise at −65° C. to a solution/suspension of 45 mmol of methoxymethyl-triphenylphosphonium chloride in 280 ml of dry diethyl ether. The mixture is stirred at the same temperature for 30 minutes, then kept at −10° C. for 30 minutes and subsequently re-cooled to −50° C. 16 mmol of 3,4,5-trifluoro-4'-(4-propylcyclohexyl)biphenyl -2-carbaldehyde are added at this temperature. The reaction mixture is allowed to thaw slowly, and stirring is continued at room temperature. Ice-water is added to the reaction mixture, and the organic phase is separated off and washed with cold water. After drying using sodium sulfate, the mixture is evaporated under reduced pressure, and the residue is stirred with n-heptane and filtered. The filtrate is chromatographed on silica gel (n-heptane/ethyl acetate 98:2), giving 3,4,5-trifluoro-2-(2-methoxyvinyl)-4'-(4-propylcyclohexyl)biphenyl (mixture of Z and E isomers).

Step 1.3

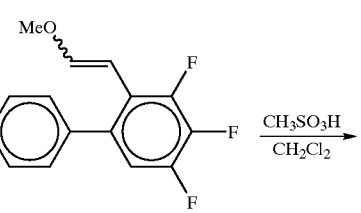

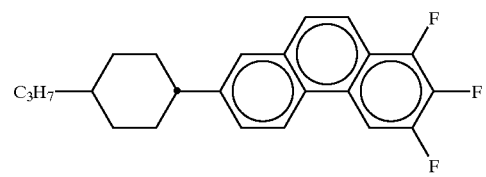

6.1 g of 3,4,5-trifluoro-2-(2-methoxyvinyl)-4'-(4-propylcyclohexyl)biphenyl are dissolved in 180 ml of dichloromethane, and 8.5 ml of methanesulfonic acid are added at 0° C. After the reaction mixture has been stirred at 0° C. for 2.5 hours, it is added to ice-water and subjected to conventional work-up. Chromatographic purification (silica gel, n-heptane) and recrystallisation from n-heptane gives 1,2,3-trifluoro-7-(4-propylcyclohexyl)phenanthrene in the form of colourless crystals. C: 124, N: 124.4, I; $\Delta\epsilon$=12.7; $\Delta n$=0.1843;

The following compounds of the formula

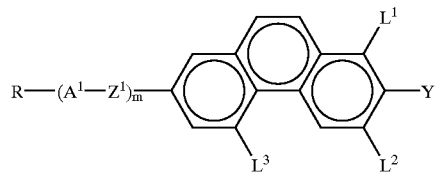

are prepared analogously:

| R | —(A¹—Z¹)ₘ— | Y | L¹ | L² | L³ | |
|---|---|---|---|---|---|---|
| CH₃ | 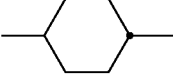 | H | H | H | H | |
| C₂H₅ | 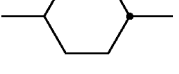 | H | H | H | H | |
| n-C₃H₇ | 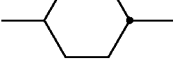 | H | H | H | H | C 118 N 134.5 I; Δε = 2.0; Δn = 0.2139 |
| n-C₄H₉ | 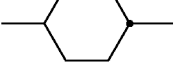 | H | H | H | H | |
| n-C₅H₁₁ |  | H | H | H | H | |
| n-C₆H₁₃ |  | H | H | H | H | |
| CH₃ | 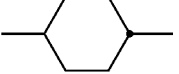 | F | H | H | H | |
| CH₃ | 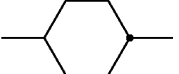 | F | F | H | H | |
| CH₃ |  | F | F | F | H | |
| C₂H₅ |  | F | H | H | H | |
| C₂H₅ |  | F | F | H | H | |
| C₂H₅ |  | F | F | F | H | |
| n-C₃H₇ | 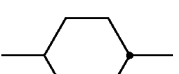 | F | H | H | H | |
| n-C₃H₇ | 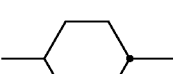 | F | F | H | H | C 124 N 178.3 I; Δε = 9.3; Δn = 0.2027 |
| n-C₅H₁₁ | 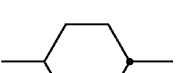 | F | H | H | H | |

-continued
| R | —(A$^1$—Z$^1$)$_m$— | Y | L$^1$ | L$^2$ | L$^3$ |
|---|---|---|---|---|---|
| n-C$_5$H$_{11}$ | 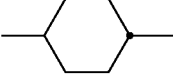 | F | F | H | H |
| n-C$_5$H$_{11}$ |  | F | F | F | H |
| CH$_2$=CH |  | F | H | H | H |
| CH$_2$=CH |  | F | F | H | H |
| CH$_2$=CH |  | F | F | F | H |
| CH$_3$CH=CH |  | F | H | H | H |
| CH$_3$CH=CH |  | F | F | H | H |
| CH$_3$CH=CH |  | F | F | F | H |
| CH$_2$=CHC$_2$H$_4$ |  | F | H | H | H |
| CH$_2$=CHC$_2$H$_4$ | 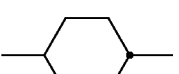 | F | F | H | H |
| CH$_2$=CHC$_2$H$_4$ | 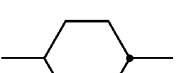 | F | F | F | H |
| CH$_3$CH=CHC$_2$H$_4$ | 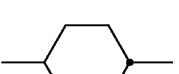 | F | H | H | H |
| CH$_3$CH=CHC$_2$H$_4$ | 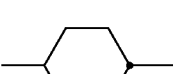 | F | F | H | H |
| CH$_3$CH=CHC$_2$H$_4$ | 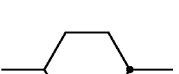 | F | F | F | H |
| CH$_3$ | 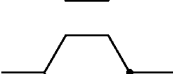 | OCF$_3$ | H | H | H |

-continued

| R | —(A¹—Z¹)ₘ— | Y | L¹ | L² | L³ |
|---|---|---|---|---|---|
| CH₃ | cyclohexyl | OCF₃ | F | H | H |
| CH₃ | cyclohexyl | OCF₃ | F | F | H |
| C₂H₅ | cyclohexyl | OCF₃ | H | H | H |
| C₂H₅ | cyclohexyl | OCF₃ | F | H | H |
| C₂H₅ | cyclohexyl | OCF₃ | F | F | H |
| n-C₃H₇ | cyclohexyl | OCF₃ | H | H | H |
| n-C₃H₇ | cyclohexyl | OCF₃ | F | H | H |
| n-C₃H₇ | cyclohexyl | OCF₃ | F | F | H |
| n-C₅H₁₁ | cyclohexyl | OCF₃ | H | H | H |
| n-C₅H₁₁ | cyclohexyl | OCF₃ | F | H | H |
| n-C₅H₁₁ | cyclohexyl | OCF₃ | F | F | H |
| CH₂=CH | cyclohexyl | OCF₃ | H | H | H |
| CH₂=CH | cyclohexyl | OCF₃ | F | H | H |
| CH₂=CH | cyclohexyl | OCF₃ | F | F | H |
| CH₃CH=CH | cyclohexyl | OCF₃ | H | H | H |

-continued
| R | —(A¹—Z¹)ₘ— | Y | L¹ | L² | L³ |
|---|---|---|---|---|---|
| CH₃CH=CH | 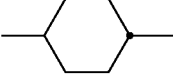 | OCF₃ | F | H | H |
| CH₃CH=CH |  | OCF₃ | F | F | H |
| CH₂=CHC₂H₄ |  | OCF₃ | H | H | H |
| CH₂=CHC₂H₄ |  | OCF₃ | F | H | H |
| CH₂=CHC₂H₄ |  | OCF₃ | F | F | H |
| CH₃CH=CHC₂H₄ |  | OCF₃ | H | H | H |
| CH₃CH=CHC₂H₄ |  | OCF₃ | F | H | H |
| CH₃CH=CHC₂H₄ |  | OCF₃ | F | F | H |
| CH₃ |  | CF₃ | H | H | H |
| CH₃ | 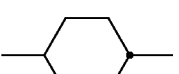 | CF₃ | F | H | H |
| CH₃ | 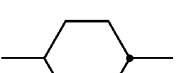 | CF₃ | F | F | H |
| C₂H₅ | 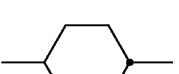 | CF₃ | H | H | H |
| C₂H₅ | 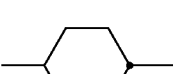 | CF₃ | F | H | H |
| C₂H₅ | 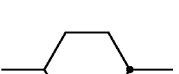 | CF₃ | F | F | H |
| n-C₃H₇ | 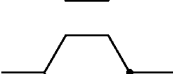 | CF₃ | H | H | H |

-continued
| R | —(A¹—Z¹)ₘ— | Y | L¹ | L² | L³ |
|---|---|---|---|---|---|
| n-C₃H₇ |  | CF₃ | F | H | H |
| n-C₃H₇ | 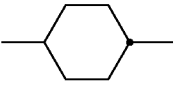 | CF₃ | F | F | H |
| n-C₅H₁₁ |  | CF₃ | H | H | H |
| n-C₅H₁₁ |  | CF₃ | F | H | H |
| n-C₅H₁₁ |  | CF₃ | F | F | H |
| CH₂=CH |  | CF₃ | H | H | H |
| CH₂=CH |  | CF₃ | F | H | H |
| CH₂=CH |  | CF₃ | F | F | H |
| CH₃CH=CH |  | CF₃ | H | H | H |
| CH₃CH=CH |  | CF₃ | F | H | H |
| CH₃CH=CH | 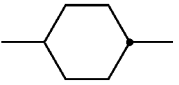 | CF₃ | F | F | H |
| CH₂=CHC₂H₄ | 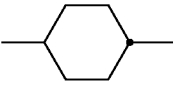 | CF₃ | H | H | H |
| CH₂=CHC₂H₄ | 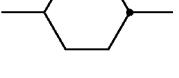 | CF₃ | F | H | H |
| CH₂=CHC₂H₄ | 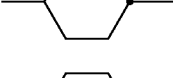 | CF₃ | F | F | H |
| CH₃CH=CHC₂H₄ |  | CF₃ | H | H | H |

-continued

| R | —(A¹—Z¹)ₘ— | Y | L¹ | L² | L³ |
|---|---|---|---|---|---|
| CH₃CH=CHC₂H₄ | cyclohexyl | CF₃ | F | H | H |
| CH₃CH=CHC₂H₄ | cyclohexyl | CF₃ | F | F | H |
| CH₃ | cyclohexyl | SF₅ | H | H | H |
| CH₃ | cyclohexyl | SF₅ | F | H | H |
| CH₃ | cyclohexyl | SF₅ | F | F | H |
| C₂H₅ | cyclohexyl | SF₅ | H | H | H |
| C₂H₅ | cyclohexyl | SF₅ | F | H | H |
| C₂H₅ | cyclohexyl | SF₅ | F | F | H |
| n-C₃H₇ | cyclohexyl | SF₅ | H | H | H |
| n-C₃H₇ | cyclohexyl | SF₅ | F | H | H |
| n-C₃H₇ | cyclohexyl | SF₅ | F | F | H |
| n-C₅H₁₁ | cyclohexyl | SF₅ | H | H | H |
| n-C₅H₁₁ | cyclohexyl | SF₅ | F | H | H |
| n-C₅H₁₁ | cyclohexyl | SF₅ | F | F | H |
| CH₂=CH | cyclohexyl | SF₅ | H | H | H |

-continued
| R | —(A¹—Z¹)ₘ— | Y | L¹ | L² | L³ |
|---|---|---|---|---|---|
| CH₂=CH | 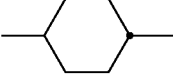 | SF₅ | F | H | H |
| CH₂=CH | 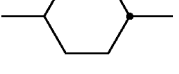 | SF₅ | F | F | H |
| CH₃CH=CH | 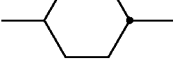 | SF₅ | H | H | H |
| CH₃CH=CH | 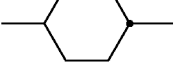 | SF₅ | F | H | H |
| CH₃CH=CH |  | SF₅ | F | F | H |
| CH₂=CHC₂H₄ |  | SF₅ | H | H | H |
| CH₂=CHC₂H₄ | 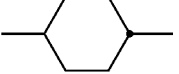 | SF₅ | F | H | H |
| CH₂=CHC₂H₄ | 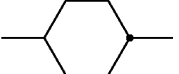 | SF₅ | F | F | H |
| CH₃CH=CHC₂H₄ |  | SF₅ | H | H | H |
| CH₃CH=CHC₂H₄ |  | SF₅ | F | H | H |
| CH₃CH=CHC₂H₄ |  | SF₅ | F | F | H |
| CH₃ |  | CH=CF₂ | H | H | H |
| CH₃ | 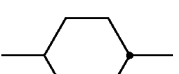 | CH=CF₂ | F | H | H |
| CH₃ | 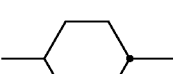 | CH=CF₂ | F | F | H |
| C₂H₅ | 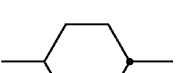 | CH=CF₂ | H | H | H |

-continued
| R | —(A¹—Z¹)ₘ— | Y | L¹ | L² | L³ |
|---|---|---|---|---|---|
| C₂H₅ | 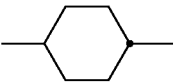 | CH=CF₂ | F | H | H |
| C₂H₅ | 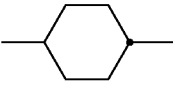 | CH=CF₂ | F | F | H |
| n-C₃H₇ | 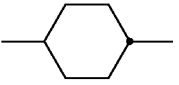 | CH=CF₂ | H | H | H |
| n-C₃H₇ | 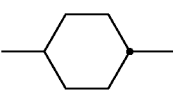 | CH=CF₂ | F | H | H |
| n-C₃H₇ | 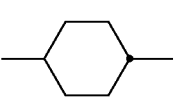 | CH=CF₂ | F | F | H |
| n-C₅H₁₁ | 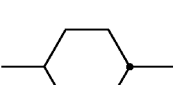 | CH=CF₂ | H | H | H |
| n-C₅H₁₁ | 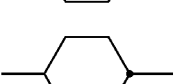 | CH=CF₂ | F | H | H |
| n-C₅H₁₁ | 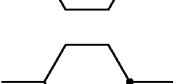 | CH=CF₂ | F | F | H |
| CH₂=CH | 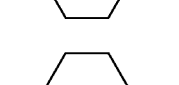 | CH=CF₂ | H | H | H |
| CH₂=CH | 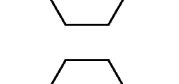 | CH=CF₂ | F | H | H |
| CH₂=CH | 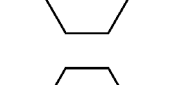 | CH=CF₂ | F | F | H |
| CH₃CH=CH | 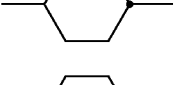 | CH=CF₂ | H | H | H |
| CH₃CH=CH | 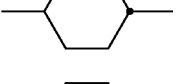 | CH=CF₂ | F | H | H |
| CH₃CH=CH | 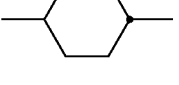 | CH=CF₂ | F | F | H |
| CH₂=CHC₂H₄ | 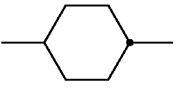 | CH=CF₂ | H | H | H |

-continued

| R | —(A¹—Z¹)ₘ— | Y | L¹ | L² | L³ |
|---|---|---|---|---|---|
| CH₂=CHC₂H₄ | cyclohexylene | CH=CF₂ | F | H | H |
| CH₂=CHC₂H₄ | cyclohexylene | CH=CF₂ | F | F | H |
| CH₃CH=CHC₂H₄ | cyclohexylene | CH=CF₂ | H | H | H |
| CH₃CH=CHC₂H₄ | cyclohexylene | CH=CF₂ | F | H | H |
| CH₃CH=CHC₂H₄ | cyclohexylene | CH=CF₂ | F | F | H |
| CH₃ | cyclohexylene | OCHFCF₃ | H | H | H |
| CH₃ | cyclohexylene | OCHFCF₃ | F | H | H |
| CH₃ | cyclohexylene | OCHFCF₃ | F | F | H |
| C₂H₅ | cyclohexylene | OCHFCF₃ | H | H | H |
| C₂H₅ | cyclohexylene | OCHFCF₃ | F | H | H |
| C₂H₅ | cyclohexylene | OCHFCF₃ | F | F | H |
| n-C₃H₇ | cyclohexylene | OCHFCF₃ | H | H | H |
| n-C₃H₇ | cyclohexylene | OCHFCF₃ | F | H | H |
| n-C₃H₇ | cyclohexylene | OCHFCF₃ | F | F | H |
| n-C₅H₁₁ | cyclohexylene | OCHFCF₃ | H | H | H |

-continued

| R | —(A¹—Z¹)ₘ— | Y | L¹ | L² | L³ |
|---|---|---|---|---|---|
| n-C₅H₁₁ | (cyclohexane) | OCHFCF₃ | F | H | H |
| n-C₅H₁₁ | (cyclohexane) | OCHFCF₃ | F | F | H |
| CH₂=CH | (cyclohexane) | OCHFCF₃ | H | H | H |
| CH₂=CH | (cyclohexane) | OCHFCF₃ | F | H | H |
| CH₂=CH | (cyclohexane) | OCHFCF₃ | F | F | H |
| CH₃CH=CH | (cyclohexane) | OCHFCF₃ | H | H | H |
| CH₃CH=CH | (cyclohexane) | OCHFCF₃ | F | H | H |
| CH₃CH=CH | (cyclohexane) | OCHFCF₃ | F | F | H |
| CH₂=CHC₂H₄ | (cyclohexane) | OCHFCF₃ | H | H | H |
| CH₂=CHC₂H₄ | (cyclohexane) | OCHFCF₃ | F | H | H |
| CH₃CH=CHC₂H₄ | (cyclohexane) | OCHFCF₃ | F | F | H |
| CH₃CH=CHC₂H₄ | (cyclohexane) | OCHFCF₃ | H | H | H |
| CH₃CH=CHC₂H₄ | (cyclohexane) | OCHFCF₃ | F | H | H |
| CH₃CH=CHC₂H₄ | (cyclohexane) | OCHFCF₃ | F | F | H |
| CH₃ | (cyclohexane) | OCF₂CHFCF₃ | H | H | H |

-continued

| R | —(A¹—Z¹)ₘ— | Y | L¹ | L² | L³ |
|---|---|---|---|---|---|
| CH₃ | cyclohexyl | OCF₂CHFCF₃ | F | H | H |
| CH₃ | cyclohexyl | OCF₂CHFCF₃ | F | F | H |
| C₂H₅ | cyclohexyl | OCF₂CHFCF₃ | H | H | H |
| C₂H₅ | cyclohexyl | OCF₂CHFCF₃ | F | H | H |
| C₂H₅ | cyclohexyl | OCF₂CHFCF₃ | F | F | H |
| n-C₃H₇ | cyclohexyl | OCF₂CHFCF₃ | H | H | H |
| n-C₃H₇ | cyclohexyl | OCF₂CHFCF₃ | F | H | H |
| n-C₃H₇ | cyclohexyl | OCF₂CHFCF₃ | F | F | H |
| n-C₅H₁₁ | cyclohexyl | OCF₂CHFCF₃ | H | H | H |
| n-C₅H₁₁ | cyclohexyl | OCF₂CHFCF₃ | F | H | H |
| n-C₅H₁₁ | cyclohexyl | OCF₂CHFCF₃ | F | F | H |
| CH₂=CH | cyclohexyl | OCF₂CHFCF₃ | H | H | H |
| CH₂=CH | cyclohexyl | OCF₂CHFCF₃ | F | H | H |
| CH₂=CH | cyclohexyl | OCF₂CHFCF₃ | F | F | H |
| CH₃CH=CH | cyclohexyl | OCF₂CHFCF₃ | H | H | H |

-continued
| R | —(A¹—Z¹)ₘ— | Y | L¹ | L² | L³ |
|---|---|---|---|---|---|
| CH₃CH=CH | 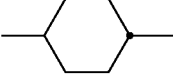 | OCF₂CHFCF₃ | F | H | H |
| CH₃CH=CH | 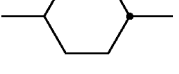 | OCF₂CHFCF₃ | F | F | H |
| CH₂=CHC₂H₄ | 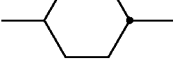 | OCF₂CHFCF₃ | H | H | H |
| CH₂=CHC₂H₄ | 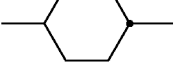 | OCF₂CHFCF₃ | F | H | H |
| CH₂=CHC₂H₄ |  | OCF₂CHFCF₃ | F | F | H |
| CH₃CH=CHC₂H₄ |  | OCF₂CHFCF₃ | H | H | H |
| CH₃CH=CHC₂H₄ | 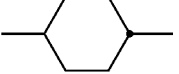 | OCF₂CHFCF₃ | F | H | H |
| CH₃CH=CHC₂H₄ | 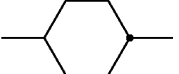 | OCF₂CHFCF₃ | F | F | H |
| CH₃ |  | H | H | H | F |
| C₂H₅ |  | H | H | H | F |
| n-C₃H₇ |  | H | H | H | F |
| n-C₄H₉ |  | H | H | H | F |
| n-C₅H₁₁ | 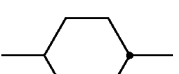 | H | H | H | F |
| n-C₆H₁₃ | 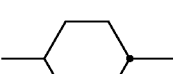 | H | H | H | F |
| CH₃ | 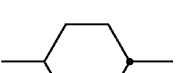 | F | H | H | F |

-continued

| R | —(A¹—Z¹)ₘ— | Y | L¹ | L² | L³ | |
|---|---|---|---|---|---|---|
| CH₃ | cyclohexyl | F | F | H | F | |
| CH₃ | cyclohexyl | F | F | F | F | |
| C₂H₅ | cyclohexyl | F | H | H | F | |
| C₂H₅ | cyclohexyl | F | F | H | F | |
| C₂H₅ | cyclohexyl | F | F | F | F | |
| n-C₃H₇ | cyclohexyl | F | H | H | F | |
| n-C₃H₇ | cyclohexyl | F | F | H | F | |
| n-C₃H₇ | cyclohexyl | F | F | F | F | C 139 N (116.9) I; $\Delta n = 0.1845$; $\Delta\epsilon = 15.1$ |
| n-C₅H₁₁ | cyclohexyl | F | H | H | F | |
| n-C₅H₁₁ | cyclohexyl | F | F | H | F | |
| n-C₅H₁₁ | cyclohexyl | F | F | F | F | |
| CH₂=CH | cyclohexyl | F | H | H | F | |
| CH₂=CH | cyclohexyl | F | F | H | F | |
| CH₂=CH | cyclohexyl | F | F | F | F | |
| CH₃CH=CH | cyclohexyl | F | H | H | F | |

-continued
| R | —(A¹—Z¹)ₘ— | Y | L¹ | L² | L³ |
|---|---|---|---|---|---|
| CH₃CH=CH | 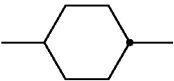 | F | F | H | F |
| CH₃CH=CH |  | F | F | F | F |
| CH₂=CHC₂H₄ |  | F | H | H | F |
| CH₂=CHC₂H₄ |  | F | F | H | F |
| CH₂=CHC₂H₄ | 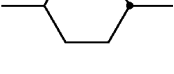 | F | F | F | F |
| CH₃CH=CHC₂H₄ | 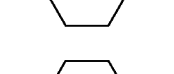 | F | H | H | F |
| CH₃CH=CHC₂H₄ | 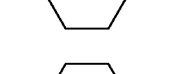 | F | F | H | F |
| CH₃CH=CHC₂H₄ |  | F | F | F | F |
| CH₃ | 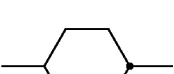 | OCF₃ | H | H | F |
| CH₃ |  | OCF₃ | F | H | F |
| CH₃ | 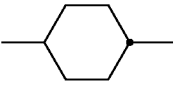 | OCF₃ | F | F | F |
| C₂H₅ | 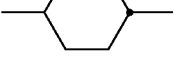 | OCF₃ | H | H | F |
| C₂H₅ | 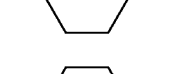 | OCF₃ | F | H | F |
| C₂H₅ | 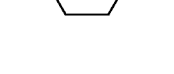 | OCF₃ | F | F | F |
| n-C₃H₇ |  | OCF₃ | H | H | F |

-continued

| R | —(A¹—Z¹)ₘ— | Y | L¹ | L² | L³ |
|---|---|---|---|---|---|
| n-C₃H₇ | cyclohexyl | OCF₃ | F | H | F |
| n-C₃H₇ | cyclohexyl | OCF₃ | F | F | F |
| n-C₅H₁₁ | cyclohexyl | OCF₃ | H | H | F |
| n-C₅H₁₁ | cyclohexyl | OCF₃ | F | H | F |
| n-C₅H₁₁ | cyclohexyl | OCF₃ | F | F | F |
| CH₂=CH | cyclohexyl | OCF₃ | H | H | F |
| CH₂=CH | cyclohexyl | OCF₃ | F | H | F |
| CH₂=CH | cyclohexyl | OCF₃ | F | F | F |
| CH₃CH=CH | cyclohexyl | OCF₃ | H | H | F |
| CH₃CH=CH | cyclohexyl | OCF₃ | F | H | F |
| CH₃CH=CH | cyclohexyl | OCF₃ | F | F | F |
| CH₂=CHC₂H₄ | cyclohexyl | OCF₃ | H | H | F |
| CH₂=CHC₂H₄ | cyclohexyl | OCF₃ | F | H | F |
| CH₂=CHC₂H₄ | cyclohexyl | OCF₃ | F | F | F |
| CH₃CH=CHC₂H₄ | cyclohexyl | OCF₃ | H | H | F |

-continued

| R | —(A¹—Z¹)ₘ— | Y | L¹ | L² | L³ |
|---|---|---|---|---|---|
| CH₃CH=CHC₂H₄ | cyclohexyl | OCF₃ | F | H | F |
| CH₃CH=CHC₂H₄ | cyclohexyl | OCF₃ | F | F | F |
| CH₃ | cyclohexyl | CF₃ | H | H | F |
| CH₃ | cyclohexyl | CF₃ | F | H | F |
| CH₃ | cyclohexyl | CF₃ | F | F | F |
| C₂H₅ | cyclohexyl | CF₃ | H | H | F |
| C₂H₅ | cyclohexyl | CF₃ | F | H | F |
| C₂H₅ | cyclohexyl | CF₃ | F | F | F |
| n-C₃H₇ | cyclohexyl | CF₃ | H | H | F |
| n-C₃H₇ | cyclohexyl | CF₃ | F | H | F |
| n-C₃H₇ | cyclohexyl | CF₃ | F | F | F |
| n-C₅H₁₁ | cyclohexyl | CF₃ | H | H | F |
| n-C₅H₁₁ | cyclohexyl | CF₃ | F | H | F |
| n-C₅H₁₁ | cyclohexyl | CF₃ | F | F | F |
| CH₂=CH | cyclohexyl | CF₃ | H | H | F |

-continued
| R | —(A¹—Z¹)ₘ— | Y | L¹ | L² | L³ |
|---|---|---|---|---|---|
| CH₂=CH | 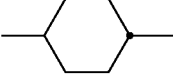 | CF₃ | F | H | F |
| CH₂=CH | 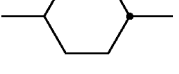 | CF₃ | F | F | F |
| CH₃CH=CH | 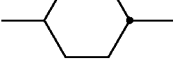 | CF₃ | H | H | F |
| CH₃CH=CH | 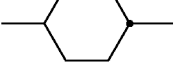 | CF₃ | F | H | F |
| CH₃CH=CH |  | CF₃ | F | F | F |
| CH₂=CHC₂H₄ |  | CF₃ | H | H | F |
| CH₂=CHC₂H₄ | 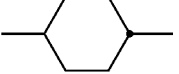 | CF₃ | F | H | F |
| CH₂=CHC₂H₄ | 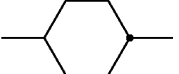 | CF₃ | F | F | F |
| CH₃CH=CHC₂H₄ |  | CF₃ | H | H | F |
| CH₃CH=CHC₂H₄ |  | CF₃ | F | H | F |
| CH₃CH=CHC₂H₄ |  | CF₃ | F | F | F |
| CH₃ |  | SF₅ | H | H | F |
| CH₃ | 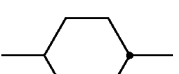 | SF₅ | F | H | F |
| CH₃ | 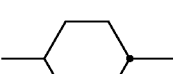 | SF₅ | F | F | F |
| C₂H₅ | 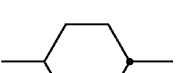 | SF₅ | H | H | F |

-continued
| R | —(A¹—Z¹)ₘ— | Y | L¹ | L² | L³ |
|---|---|---|---|---|---|
| C₂H₅ | 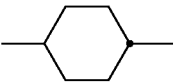 | SF₅ | F | H | F |
| C₂H₅ | 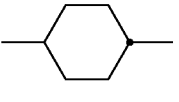 | SF₅ | F | F | F |
| n-C₃H₇ | 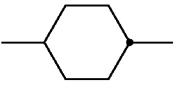 | SF₅ | H | H | F |
| n-C₃H₇ | 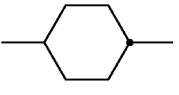 | SF₅ | F | H | F |
| n-C₃H₇ |  | SF₅ | F | F | F |
| n-C₅H₁₁ | 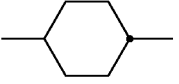 | SF₅ | H | H | F |
| n-C₅H₁₁ |  | SF₅ | F | H | F |
| n-C₅H₁₁ | 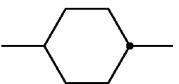 | SF₅ | F | F | F |
| CH₂=CH |  | SF₅ | H | H | F |
| CH₂=CH | 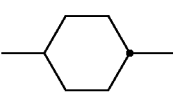 | SF₅ | F | H | F |
| CH₂=CH | 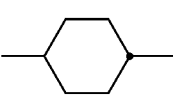 | SF₅ | F | F | F |
| CH₃CH=CH | 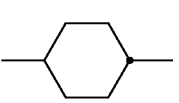 | SF₅ | H | H | F |
| CH₃CH=CH | 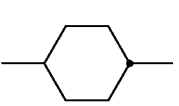 | SF₅ | F | H | F |
| CH₃CH=CH | 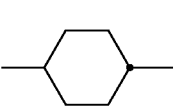 | SF₅ | F | F | F |
| CH₂=CHC₂H₄ | 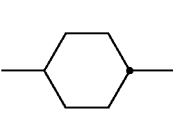 | SF₅ | H | H | F |

-continued

| R | —(A¹—Z¹)ₘ— | Y | L¹ | L² | L³ |
|---|---|---|---|---|---|
| CH₂=CHC₂H₄ | cyclohexyl | SF₅ | F | H | F |
| CH₂=CHC₂H₄ | cyclohexyl | SF₅ | F | F | F |
| CH₃CH=CHC₂H₄ | cyclohexyl | SF₅ | H | H | F |
| CH₃CH=CHC₂H₄ | cyclohexyl | SF₅ | F | H | F |
| CH₃CH=CHC₂H₄ | cyclohexyl | SF₅ | F | F | F |
| CH₃ | cyclohexyl | CH=CF₂ | H | H | F |
| CH₃ | cyclohexyl | CH=CF₂ | F | H | F |
| CH₃ | cyclohexyl | CH=CF₂ | F | F | F |
| C₂H₅ | cyclohexyl | CH=CF₂ | H | H | F |
| C₂H₅ | cyclohexyl | CH=CF₂ | F | H | F |
| C₂H₅ | cyclohexyl | CH=CF₂ | F | F | F |
| n-C₃H₇ | cyclohexyl | CH=CF₂ | H | H | F |
| n-C₃H₇ | cyclohexyl | CH=CF₂ | F | H | F |
| n-C₃H₇ | cyclohexyl | CH=CF₂ | F | F | F |
| n-C₅H₁₁ | cyclohexyl | CH=CF₂ | H | H | F |

-continued

| R | —(A¹—Z¹)ₘ— | Y | L¹ | L² | L³ |
|---|---|---|---|---|---|
| n-C₅H₁₁ | cyclohexyl | CH=CF₂ | F | H | F |
| n-C₅H₁₁ | cyclohexyl | CH=CF₂ | F | F | F |
| CH₂=CH | cyclohexyl | CH=CF₂ | H | H | F |
| CH₂=CH | cyclohexyl | CH=CF₂ | F | H | F |
| CH₂=CH | cyclohexyl | CH=CF₂ | F | F | F |
| CH₃CH=CH | cyclohexyl | CH=CF₂ | H | H | F |
| CH₃CH=CH | cyclohexyl | CH=CF₂ | F | H | F |
| CH₃CH=CH | cyclohexyl | CH=CF₂ | F | F | F |
| CH₂=CHC₂H₄ | cyclohexyl | CH=CF₂ | H | H | F |
| CH₂=CHC₂H₄ | cyclohexyl | CH=CF₂ | F | H | F |
| CH₂=CHC₂H₄ | cyclohexyl | CH=CF₂ | F | F | F |
| CH₃CH=CHC₂H₄ | cyclohexyl | CH=CF₂ | H | H | F |
| CH₃CH=CHC₂H₄ | cyclohexyl | CH=CF₂ | F | H | F |
| CH₃CH=CHC₂H₄ | cyclohexyl | CH=CF₂ | F | F | F |
| CH₃ | cyclohexyl | OCHFCF₃ | H | H | F |

-continued

| R | —(A¹—Z¹)ₘ— | Y | L¹ | L² | L³ |
|---|---|---|---|---|---|
| CH₃ | cyclohexyl | OCHFCF₃ | F | H | F |
| CH₃ | cyclohexyl | OCHFCF₃ | F | F | F |
| C₂H₅ | cyclohexyl | OCHFCF₃ | H | H | F |
| C₂H₅ | cyclohexyl | OCHFCF₃ | F | H | F |
| C₂H₅ | cyclohexyl | OCHFCF₃ | F | F | F |
| n-C₃H₇ | cyclohexyl | OCHFCF₃ | H | H | F |
| n-C₃H₇ | cyclohexyl | OCHFCF₃ | F | H | F |
| n-C₃H₇ | cyclohexyl | OCHFCF₃ | F | F | F |
| n-C₅H₁₁ | cyclohexyl | OCHFCF₃ | H | H | F |
| n-C₅H₁₁ | cyclohexyl | OCHFCF₃ | F | H | F |
| n-C₅H₁₁ | cyclohexyl | OCHFCF₃ | F | F | F |
| CH₂=CH | cyclohexyl | OCHFCF₃ | H | H | F |
| CH₂=CH | cyclohexyl | OCHFCF₃ | F | H | F |
| CH₂=CH | cyclohexyl | OCHFCF₃ | F | F | F |
| CH₃CH=CH | cyclohexyl | OCHFCF₃ | H | H | F |

-continued

| R | —(A¹—Z¹)ₘ— | Y | L¹ | L² | L³ |
|---|---|---|---|---|---|
| CH₃CH=CH | 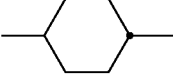 | OCHFCF₃ | F | H | F |
| CH₃CH=CH | 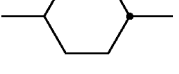 | OCHFCF₃ | F | F | F |
| CH₂=CHC₂H₄ |  | OCHFCF₃ | H | H | F |
| CH₂=CHC₂H₄ | 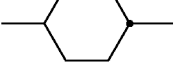 | OCHFCF₃ | F | H | F |
| CH₂=CHC₂H₄ | 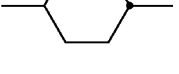 | OCHFCF₃ | F | F | F |
| CH₃CH=CHC₂H₄ | 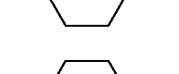 | OCHFCF₃ | H | H | F |
| CH₃CH=CHC₂H₄ | 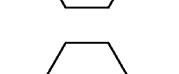 | OCHFCF₃ | F | H | F |
| CH₃CH=CHC₂H₄ | 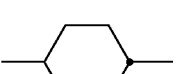 | OCHFCF₃ | F | F | F |
| CH₃ |  | OCF₂CHFCF₃ | H | H | F |
| CH₃ |  | OCF₂CHFCF₃ | F | H | F |
| CH₃ | 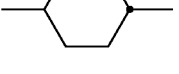 | OCF₂CHFCF₃ | F | F | F |
| C₂H₅ | 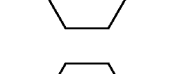 | OCF₂CHFCF₃ | H | H | F |
| C₂H₅ | 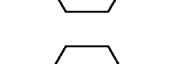 | OCF₂CHFCF₃ | F | H | F |
| C₂H₅ | 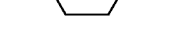 | OCF₂CHFCF₃ | F | F | F |
| n-C₃H₇ | 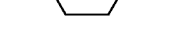 | OCF₂CHFCF₃ | H | H | F |

-continued

| R | —(A¹—Z¹)ₘ— | Y | L¹ | L² | L³ |
|---|---|---|---|---|---|
| n-C₃H₇ | cyclohexyl | OCF₂CHFCF₃ | F | H | F |
| n-C₃H₇ | cyclohexyl | OCF₂CHFCF₃ | F | F | F |
| n-C₅H₁₁ | cyclohexyl | OCF₂CHFCF₃ | H | H | F |
| n-C₅H₁₁ | cyclohexyl | OCF₂CHFCF₃ | F | H | F |
| n-C₅H₁₁ | cyclohexyl | OCF₂CHFCF₃ | F | F | F |
| CH₂=CH | cyclohexyl | OCF₂CHFCF₃ | H | H | F |
| CH₂=CH | cyclohexyl | OCF₂CHFCF₃ | F | H | F |
| CH₂=CH | cyclohexyl | OCF₂CHFCF₃ | F | F | F |
| CH₃CH=CH | cyclohexyl | OCF₂CHFCF₃ | H | H | F |
| CH₃CH=CH | cyclohexyl | OCF₂CHFCF₃ | F | H | F |
| CH₃CH=CH | cyclohexyl | OCF₂CHFCF₃ | F | F | F |
| CH₂=CHC₂H₄ | cyclohexyl | OCF₂CHFCF₃ | H | H | F |
| CH₂=CHC₂H₄ | cyclohexyl | OCF₂CHFCF₃ | F | H | F |
| CH₂=CHC₂H₄ | cyclohexyl | OCF₂CHFCF₃ | F | F | F |
| CH₃CH=CHC₂H₄ | cyclohexyl | OCF₂CHFCF₃ | H | H | F |

-continued

| R | —(A¹—Z¹)ₘ— | Y | L¹ | L² | L³ |
|---|---|---|---|---|---|
| CH₃CH=CHC₂H₄ | cyclohexyl | OCF₂CHFCF₃ | F | H | F |
| CH₃CH=CHC₂H₄ | cyclohexyl | OCF₂CHFCF₃ | F | F | F |
| CH₃ | phenyl | H | H | H | H |
| C₂H₅ | phenyl | H | H | H | H |
| n-C₃H₇ | phenyl | H | H | H | H |
| n-C₄H₉ | phenyl | H | H | H | H |
| n-C₅H₁₁ | phenyl | H | H | H | H |
| n-C₆H₁₃ | phenyl | H | H | H | H |
| CH₃ | phenyl | F | H | H | H |
| CH₃ | phenyl | F | F | H | H |
| CH₃ | phenyl | F | F | F | H |
| C₂H₅ | phenyl | F | H | H | H |
| C₂H₅ | phenyl | F | F | H | H |
| C₂H₅ | phenyl | F | F | F | H |
| n-C₃H₇ | phenyl | F | H | H | H |

-continued

| R | —(A¹—Z¹)ₘ— | Y | L¹ | L² | L³ | |
|---|---|---|---|---|---|---|
| n-C₃H₇ | ⬡ | F | F | H | H | |
| n-C₃H₇ | ⬡ | F | F | H | H | C 131 S_A 143 I; Δn = 0.2816; Δε = 16.1 |
| n-C₅H₁₁ | ⬡ | F | H | H | H | |
| n-C₅H₁₁ | ⬡ | F | F | H | H | |
| n-C₅H₁₁ | ⬡ | F | F | F | H | |
| CH₂=CH | ⬡ | F | H | H | H | |
| CH₂=CH | ⬡ | F | F | H | H | |
| CH₂=CH | ⬡ | F | F | F | H | |
| CH₃CH=CH | ⬡ | F | H | H | H | |
| CH₃CH=CH | ⬡ | F | F | H | H | |
| CH₃CH=CH | ⬡ | F | F | F | H | |
| CH₂=CHC₂H₄ | ⬡ | F | H | H | H | |
| CH₂=CHC₂H₄ | ⬡ | F | F | H | H | |
| CH₂=CHC₂H₄ | ⬡ | F | F | F | H | |
| CH₃CH=CHC₂H₄ | ⬡ | F | H | H | H | |

-continued
| R | —(A¹—Z¹)ₘ— | Y | L¹ | L² | L³ |
|---|---|---|---|---|---|
| CH₃CH=CHC₂H₄ |  | F | F | H | H |
| CH₃CH=CHC₂H₄ |  | F | F | F | H |
| CH₃ |  | OCF₃ | H | H | H |
| CH₃ |  | OCF₃ | F | H | H |
| CH₃ |  | OCF₃ | F | F | H |
| C₂H₅ |  | OCF₃ | H | H | H |
| C₂H₅ |  | OCF₃ | F | H | H |
| C₂H₅ |  | OCF₃ | F | F | H |
| n-C₃H₇ |  | OCF₃ | H | H | H |
| n-C₃H₇ |  | OCF₃ | F | H | H |
| n-C₃H₇ |  | OCF₃ | F | F | H |
| n-C₅H₁₁ |  | OCF₃ | H | H | H |
| n-C₅H₁₁ |  | OCF₃ | F | H | H |
| n-C₅H₁₁ |  | OCF₃ | F | F | H |
| CH₂=CH |  | OCF₃ | H | H | H |

-continued
| R | —(A¹—Z¹)ₘ— | Y | L¹ | L² | L³ |
|---|---|---|---|---|---|
| CH₂=CH |  | OCF₃ | F | H | H |
| CH₂=CH |  | OCF₃ | F | F | H |
| CH₃CH=CH |  | OCF₃ | H | H | H |
| CH₃CH=CH |  | OCF₃ | F | H | H |
| CH₃CH=CH |  | OCF₃ | F | F | H |
| CH₂=CHC₂H₄ |  | OCF₃ | H | H | H |
| CH₂=CHC₂H₄ |  | OCF₃ | F | H | H |
| CH₂=CHC₂H₄ |  | OCF₃ | F | F | H |
| CH₃CH=CHC₂H₄ |  | OCF₃ | H | H | H |
| CH₃CH=CHC₂H₄ |  | OCF₃ | F | H | H |
| CH₃CH=CHC₂H₄ |  | OCF₃ | F | F | H |
| CH₃ |  | CF₃ | H | H | H |
| CH₃ |  | CF₃ | F | H | H |
| CH₃ |  | CF₃ | F | F | H |
| C₂H₅ |  | CF₃ | H | H | H |

-continued

| R | —(A¹—Z¹)ₘ— | Y | L¹ | L² | L³ |
|---|---|---|---|---|---|
| C₂H₅ | phenyl | CF₃ | F | H | H |
| C₂H₅ | phenyl | CF₃ | F | F | H |
| n-C₃H₇ | phenyl | CF₃ | H | H | H |
| n-C₃H₇ | phenyl | CF₃ | F | H | H |
| n-C₃H₇ | phenyl | CF₃ | F | F | H |
| n-C₅H₁₁ | phenyl | CF₃ | H | H | H |
| n-C₅H₁₁ | phenyl | CF₃ | F | H | H |
| n-C₅H₁₁ | phenyl | CF₃ | F | F | H |
| CH₂=CH | phenyl | CF₃ | H | H | H |
| CH₂=CH | phenyl | CF₃ | F | H | H |
| CH₂=CH | phenyl | CF₃ | F | F | H |
| CH₃CH=CH | phenyl | CF₃ | H | H | H |
| CH₃CH=CH | phenyl | CF₃ | F | H | H |
| CH₃CH=CH | phenyl | CF₃ | F | F | H |
| CH₂=CHC₂H₄ | phenyl | CF₃ | H | H | H |

-continued

| R | —(A¹—Z¹)ₘ— | Y | L¹ | L² | L³ |
|---|---|---|---|---|---|
| CH₂=CHC₂H₄ | —⟨phenyl⟩— | CF₃ | F | H | H |
| CH₂=CHC₂H₄ | —⟨phenyl⟩— | CF₃ | F | F | H |
| CH₃CH=CHC₂H₄ | —⟨phenyl⟩— | CF₃ | H | H | H |
| CH₃CH=CHC₂H₄ | —⟨phenyl⟩— | CF₃ | F | H | H |
| CH₃CH=CHC₂H₄ | —⟨phenyl⟩— | CF₃ | F | F | H |
| CH₃ | —⟨phenyl⟩— | SF₅ | H | H | H |
| CH₃ | —⟨phenyl⟩— | SF₅ | F | H | H |
| CH₃ | —⟨phenyl⟩— | SF₅ | F | F | H |
| C₂H₅ | —⟨phenyl⟩— | SF₅ | H | H | H |
| C₂H₅ | —⟨phenyl⟩— | SF₅ | F | H | H |
| C₂H₅ | —⟨phenyl⟩— | SF₅ | F | F | H |
| n-C₃H₇ | —⟨phenyl⟩— | SF₅ | H | H | H |
| n-C₃H₇ | —⟨phenyl⟩— | SF₅ | F | H | H |
| n-C₃H₇ | —⟨phenyl⟩— | SF₅ | F | F | H |
| n-C₅H₁₁ | —⟨phenyl⟩— | SF₅ | H | H | H |

-continued
| R | —(A¹—Z¹)ₘ— | Y | L¹ | L² | L³ |
|---|---|---|---|---|---|
| n-C₅H₁₁ |  | SF₅ | F | H | H |
| n-C₅H₁₁ |  | SF₅ | F | F | H |
| CH₂=CH |  | SF₅ | H | H | H |
| CH₂=CH |  | SF₅ | F | H | H |
| CH₂=CH |  | SF₅ | F | F | H |
| CH₃CH=CH |  | SF₅ | H | H | H |
| CH₃CH=CH |  | SF₅ | F | H | H |
| CH₃CH=CH |  | SF₅ | F | F | H |
| CH₂=CHC₂H₄ |  | SF₅ | H | H | H |
| CH₂=CHC₂H₄ |  | SF₅ | F | H | H |
| CH₂=CHC₂H₄ |  | SF₅ | F | F | H |
| CH₃CH=CHC₂H₄ |  | SF₅ | H | H | H |
| CH₃CH=CHC₂H₄ | 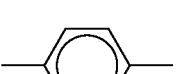 | SF₅ | F | H | H |
| CH₃CH=CHC₂H₄ |  | SF₅ | F | F | H |
| CH₃ |  | CH=CF₂ | H | H | H |

-continued

| R | —(A¹—Z¹)ₘ— | Y | L¹ | L² | L³ |
|---|---|---|---|---|---|
| CH₃ | phenyl | CH=CF₂ | F | H | H |
| CH₃ | phenyl | CH=CF₂ | F | F | H |
| C₂H₅ | phenyl | CH=CF₂ | H | H | H |
| C₂H₅ | phenyl | CH=CF₂ | F | H | H |
| C₂H₅ | phenyl | CH=CF₂ | F | F | H |
| n-C₃H₇ | phenyl | CH=CF₂ | H | H | H |
| n-C₃H₇ | phenyl | CH=CF₂ | F | H | H |
| n-C₃H₇ | phenyl | CH=CF₂ | F | F | H |
| n-C₅H₁₁ | phenyl | CH=CF₂ | H | H | H |
| n-C₅H₁₁ | phenyl | CH=CF₂ | F | H | H |
| n-C₅H₁₁ | phenyl | CH=CF₂ | F | F | H |
| CH₂=CH | phenyl | CH=CF₂ | H | H | H |
| CH₂=CH | phenyl | CH=CF₂ | F | H | H |
| CH₂=CH | phenyl | CH=CF₂ | F | F | H |
| CH₃CH=CH | phenyl | CH=CF₂ | H | H | H |

-continued
| R | —(A¹—Z¹)ₘ— | Y | L¹ | L² | L³ |
|---|---|---|---|---|---|
| CH₃CH=CH |  | CH=CF₂ | F | H | H |
| CH₃CH=CH |  | CH=CF₂ | F | F | H |
| CH₂=CHC₂H₄ |  | CH=CF₂ | H | H | H |
| CH₂=CHC₂H₄ |  | CH=CF₂ | F | H | H |
| CH₂=CHC₂H₄ |  | CH=CF₂ | F | F | H |
| CH₃CH=CHC₂H₄ |  | CH=CF₂ | H | H | H |
| CH₃CH=CHC₂H₄ |  | CH=CF₂ | F | H | H |
| CH₃CH=CHC₂H₄ |  | CH=CF₂ | F | F | H |
| CH₃ |  | OCHFCF₃ | H | H | H |
| CH₃ |  | OCHFCF₃ | F | H | H |
| CH₃ |  | OCHFCF₃ | F | F | H |
| C₂H₅ |  | OCHFCF₃ | H | H | H |
| C₂H₅ | 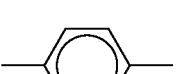 | OCHFCF₃ | F | H | H |
| C₂H₅ |  | OCHFCF₃ | F | F | H |
| n-C₃H₇ |  | OCHFCF₃ | H | H | H |

|R|—(A¹—Z¹)ₘ—|Y|L¹|L²|L³|
|---|---|---|---|---|---|
|n-C₃H₇|phenyl|OCHFCF₃|F|H|H|
|n-C₃H₇|phenyl|OCHFCF₃|F|F|H|
|n-C₅H₁₁|phenyl|OCHFCF₃|H|H|H|
|n-C₅H₁₁|phenyl|OCHFCF₃|F|H|H|
|n-C₅H₁₁|phenyl|OCHFCF₃|F|F|H|
|CH₂=CH|phenyl|OCHFCF₃|H|H|H|
|CH₂=CH|phenyl|OCHFCF₃|F|H|H|
|CH₂=CH|phenyl|OCHFCF₃|F|F|H|
|CH₃CH=CH|phenyl|OCHFCF₃|H|H|H|
|CH₃CH=CH|phenyl|OCHFCF₃|F|H|H|
|CH₃CH=CH|phenyl|OCHFCF₃|F|F|H|
|CH₂=CHC₂H₄|phenyl|OCHFCF₃|H|H|H|
|CH₂=CHC₂H₄|phenyl|OCHFCF₃|F|H|H|
|CH₂=CHC₂H₄|phenyl|OCHFCF₃|F|F|H|
|CH₃CH=CHC₂H₄|phenyl|OCHFCF₃|H|H|H|

-continued

| R | —(A¹—Z¹)$_m$— | Y | L¹ | L² | L³ |
|---|---|---|---|---|---|
| CH$_3$CH=CHC$_2$H$_4$ | phenyl | OCHFCF$_3$ | F | H | H |
| CH$_3$CH=CHC$_2$H$_4$ | phenyl | OCHFCF$_3$ | F | F | H |
| CH$_3$ | phenyl | OCF$_2$CHFCF$_3$ | H | H | H |
| CH$_3$ | phenyl | OCF$_2$CHFCF$_3$ | F | H | H |
| CH$_3$ | phenyl | OCF$_2$CHFCF$_3$ | F | F | H |
| C$_2$H$_5$ | phenyl | OCF$_2$CHFCF$_3$ | H | H | H |
| C$_2$H$_5$ | phenyl | OCF$_2$CHFCF$_3$ | F | H | H |
| C$_2$H$_5$ | phenyl | OCF$_2$CHFCF$_3$ | F | F | H |
| n-C$_3$H$_7$ | phenyl | OCF$_2$CHFCF$_3$ | H | H | H |
| n-C$_3$H$_7$ | phenyl | OCF$_2$CHFCF$_3$ | F | H | H |
| n-C$_3$H$_7$ | phenyl | OCF$_2$CHFCF$_3$ | F | F | H |
| n-C$_5$H$_{11}$ | phenyl | OCF$_2$CHFCF$_3$ | H | H | H |
| n-C$_5$H$_{11}$ | phenyl | OCF$_2$CHFCF$_3$ | F | H | H |
| n-C$_5$H$_{11}$ | phenyl | OCF$_2$CHFCF$_3$ | F | F | H |
| CH$_2$=CH | phenyl | OCF$_2$CHFCF$_3$ | H | H | H |

-continued

| R | —(A¹—Z¹)ₘ— | Y | L¹ | L² | L³ | |
|---|---|---|---|---|---|---|
| CH$_2$=CH |  | OCF$_2$CHFCF$_3$ | F | H | H | |
| CH$_2$=CH |  | OCF$_2$CHFCF$_3$ | F | F | H | |
| CH$_3$CH=CH |  | OCF$_2$CHFCF$_3$ | H | H | H | |
| CH$_3$CH=CH |  | OCF$_2$CHFCF$_3$ | F | H | H | |
| CH$_3$CH=CH |  | OCF$_2$CHFCF$_3$ | F | F | H | |
| CH$_2$=CHC$_2$H$_4$ |  | OCF$_2$CHFCF$_3$ | H | H | H | |
| CH$_2$=CHC$_2$H$_4$ |  | OCF$_2$CHFCF$_3$ | F | H | H | |
| CH$_2$=CHC$_2$H$_4$ |  | OCF$_2$CHFCF$_3$ | F | F | H | |
| CH$_3$CH=CHC$_2$H$_4$ |  | OCF$_2$CHFCF$_3$ | H | H | H | |
| CH$_3$CH=CHC$_2$H$_4$ |  | OCF$_2$CHFCF$_3$ | F | H | H | |
| CH$_3$CH=CHC$_2$H$_4$ |  | OCF$_2$CHFCF$_3$ | F | F | H | |
| CH$_3$ |  | NCS | F | F | H | |
| C$_2$H$_5$ |  | NCS | F | F | H | C 127 N; $\Delta n = 0.4475$; $\Delta \epsilon = 23.0$ |
| n-C$_3$H$_7$ |  | NCS | F | F | H | |
| n-C$_4$H$_9$ |  | NCS | F | F | H | |

-continued

| R | —(A¹—Z¹)ₘ— | Y | L¹ | L² | L³ |
|---|---|---|---|---|---|
| n-C₅H₁₁ | phenyl | NCS | F | F | H |
| n-C₆H₁₃ | phenyl | NCS | F | F | H |
| CH₃ | phenyl | H | H | H | F |
| C₂H₅ | phenyl | H | H | H | F |
| n-C₃H₇ | phenyl | H | H | H | F |
| n-C₄H₉ | phenyl | H | H | H | F |
| n-C₅H₁₁ | phenyl | H | H | H | F |
| n-C₆H₁₃ | phenyl | H | H | H | F |
| CH₃ | phenyl | F | H | H | F |
| CH₃ | phenyl | F | F | H | F |
| CH₃ | phenyl | F | F | F | F |
| C₂H₅ | phenyl | F | H | H | F |
| C₂H₅ | phenyl | F | F | H | F |
| C₂H₅ | phenyl | F | F | F | F |
| n-C₃H₇ | phenyl | F | H | H | F |

| R | —(A¹—Z¹)ₘ— | Y | L¹ | L² | L³ | |
|---|---|---|---|---|---|---|
| n-C₃H₇ | phenyl | F | F | H | F | |
| n-C₃H₇ | phenyl | F | F | F | F | C 108 S$_A$ 109 N 133.1 I; Δn = 0.2832; Δε = 19.3 |
| n-C₅H₁₁ | phenyl | F | H | H | F | |
| n-C₅H₁₁ | phenyl | F | F | H | F | |
| n-C₅H₁₁ | phenyl | F | F | F | F | |
| CH₂=CH | phenyl | F | H | H | F | |
| CH₂=CH | phenyl | F | F | H | F | |
| CH₂=CH | phenyl | F | F | F | F | |
| CH₃CH=CH | phenyl | F | H | H | F | |
| CH₃CH=CH | phenyl | F | F | H | F | |
| CH₃CH=CH | phenyl | F | F | F | F | |
| CH₂=CHC₂H₄ | phenyl | F | H | H | F | |
| CH₂=CHC₂H₄ | phenyl | F | F | H | F | |
| CH₂=CHC₂H₄ | phenyl | F | F | F | F | |
| CH₃CH=CHC₂H₄ | phenyl | F | H | H | F | |

-continued
| R | —(A¹—Z¹)ₘ— | Y | L¹ | L² | L³ |
|---|---|---|---|---|---|
| CH₃CH=CHC₂H₄ |  | F | F | H | F |
| CH₃CH=CHC₂H₄ |  | F | F | F | F |
| CH₃ |  | OCF₃ | H | H | F |
| CH₃ |  | OCF₃ | F | H | F |
| CH₃ |  | OCF₃ | F | F | F |
| C₂H₅ |  | OCF₃ | H | H | F |
| C₂H₅ |  | OCF₃ | F | H | F |
| C₂H₅ |  | OCF₃ | F | F | F |
| n-C₃H₇ |  | OCF₃ | H | H | F |
| n-C₃H₇ |  | OCF₃ | F | H | F |
| n-C₃H₇ |  | OCF₃ | F | F | F |
| n-C₅H₁₁ |  | OCF₃ | H | H | F |
| n-C₅H₁₁ |  | OCF₃ | F | H | F |
| n-C₅H₁₁ |  | OCF₃ | F | F | F |
| CH₂=CH |  | OCF₃ | H | H | F |

-continued
| R | —(A¹—Z¹)ₘ— | Y | L¹ | L² | L³ |
|---|---|---|---|---|---|
| CH₂=CH |  | OCF₃ | F | H | F |
| CH₂=CH |  | OCF₃ | F | F | F |
| CH₃CH=CH |  | OCF₃ | H | H | F |
| CH₃CH=CH |  | OCF₃ | F | H | F |
| CH₃CH=CH |  | OCF₃ | F | F | F |
| CH₂=CHC₂H₄ |  | OCF₃ | H | H | F |
| CH₂=CHC₂H₄ |  | OCF₃ | F | H | F |
| CH₂=CHC₂H₄ |  | OCF₃ | F | F | F |
| CH₃CH=CHC₂H₄ |  | OCF₃ | H | H | F |
| CH₃CH=CHC₂H₄ |  | OCF₃ | F | H | F |
| CH₃CH=CHC₂H₄ |  | OCF₃ | F | F | F |
| CH₃ |  | CF₃ | H | H | F |
| CH₃ | 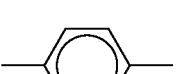 | CF₃ | F | H | F |
| CH₃ |  | CF₃ | F | F | F |
| C₂H₅ |  | CF₃ | H | H | F |

-continued

| R | —(A¹—Z¹)ₘ— | Y | L¹ | L² | L³ |
|---|---|---|---|---|---|
| C₂H₅ | phenyl | CF₃ | F | H | F |
| C₂H₅ | phenyl | CF₃ | F | F | F |
| n-C₃H₇ | phenyl | CF₃ | H | H | F |
| n-C₃H₇ | phenyl | CF₃ | F | H | F |
| n-C₃H₇ | phenyl | CF₃ | F | F | F |
| n-C₅H₁₁ | phenyl | CF₃ | H | H | F |
| n-C₅H₁₁ | phenyl | CF₃ | F | H | F |
| n-C₅H₁₁ | phenyl | CF₃ | F | F | F |
| CH₂=CH | phenyl | CF₃ | H | H | F |
| CH₂=CH | phenyl | CF₃ | F | H | F |
| CH₂=CH | phenyl | CF₃ | F | F | F |
| CH₃CH=CH | phenyl | CF₃ | H | H | F |
| CH₃CH=CH | phenyl | CF₃ | F | H | F |
| CH₃CH=CH | phenyl | CF₃ | F | F | F |
| CH₂=CHC₂H₄ | phenyl | CF₃ | H | H | F |

-continued

| R | $-(A^1-Z^1)_m-$ | Y | $L^1$ | $L^2$ | $L^3$ |
|---|---|---|---|---|---|
| $CH_2=CHC_2H_4$ | phenyl | $CF_3$ | F | H | F |
| $CH_2=CHC_2H_4$ | phenyl | $CF_3$ | F | F | F |
| $CH_3CH=CHC_2H_4$ | phenyl | $CF_3$ | H | H | F |
| $CH_3CH=CHC_2H_4$ | phenyl | $CF_3$ | F | H | F |
| $CH_3CH=CHC_2H_4$ | phenyl | $CF_3$ | F | F | F |
| $CH_3$ | phenyl | $SF_5$ | H | H | F |
| $CH_3$ | phenyl | $SF_5$ | F | H | F |
| $CH_3$ | phenyl | $SF_5$ | F | F | F |
| $C_2H_5$ | phenyl | $SF_5$ | H | H | F |
| $C_2H_5$ | phenyl | $SF_5$ | F | H | F |
| $C_2H_5$ | phenyl | $SF_5$ | F | F | F |
| $n-C_3H_7$ | phenyl | $SF_5$ | H | H | F |
| $n-C_3H_7$ | phenyl | $SF_5$ | F | H | F |
| $n-C_3H_7$ | phenyl | $SF_5$ | F | F | F |
| $n-C_5H_{11}$ | phenyl | $SF_5$ | H | H | F |

-continued

| R | —(A¹—Z¹)ₘ— | Y | L¹ | L² | L³ |
|---|---|---|---|---|---|
| n-C₅H₁₁ | phenyl | SF₅ | F | H | F |
| n-C₅H₁₁ | phenyl | SF₅ | F | F | F |
| CH₂=CH | phenyl | SF₅ | H | H | F |
| CH₂=CH | phenyl | SF₅ | F | H | F |
| CH₂=CH | phenyl | SF₅ | F | F | F |
| CH₃CH=CH | phenyl | SF₅ | H | H | F |
| CH₃CH=CH | phenyl | SF₅ | F | H | F |
| CH₃CH=CH | phenyl | SF₅ | F | F | F |
| CH₂=CHC₂H₄ | phenyl | SF₅ | H | H | F |
| CH₂=CHC₂H₄ | phenyl | SF₅ | F | H | F |
| CH₂=CHC₂H₄ | phenyl | SF₅ | F | F | F |
| CH₃CH=CHC₂H₄ | phenyl | SF₅ | H | H | F |
| CH₃CH=CHC₂H₄ | phenyl | SF₅ | F | H | F |
| CH₃CH=CHC₂H₄ | phenyl | SF₅ | F | F | F |
| CH₃ | phenyl | CH=CF₂ | H | H | F |

-continued

| R | —(A¹—Z¹)ₘ— | Y | L¹ | L² | L³ |
|---|---|---|---|---|---|
| CH₃ | phenyl | CH=CF₂ | F | H | F |
| CH₃ | phenyl | CH=CF₂ | F | F | F |
| C₂H₅ | phenyl | CH=CF₂ | H | H | F |
| C₂H₅ | phenyl | CH=CF₂ | F | H | F |
| C₂H₅ | phenyl | CH=CF₂ | F | F | F |
| n-C₃H₇ | phenyl | CH=CF₂ | H | H | F |
| n-C₃H₇ | phenyl | CH=CF₂ | F | H | F |
| n-C₃H₇ | phenyl | CH=CF₂ | F | F | F |
| n-C₅H₁₁ | phenyl | CH=CF₂ | H | H | F |
| n-C₅H₁₁ | phenyl | CH=CF₂ | F | H | F |
| n-C₅H₁₁ | phenyl | CH=CF₂ | F | F | F |
| CH₂=CH | phenyl | CH=CF₂ | H | H | F |
| CH₂=CH | phenyl | CH=CF₂ | F | H | F |
| CH₂=CH | phenyl | CH=CF₂ | F | F | F |
| CH₃CH=CH | phenyl | CH=CF₂ | H | H | F |

-continued
| R | —(A¹—Z¹)ₘ— | Y | L¹ | L² | L³ |
|---|---|---|---|---|---|
| CH₃CH=CH |  | CH=CF₂ | F | H | F |
| CH₃CH=CH |  | CH=CF₂ | F | F | F |
| CH₂=CHC₂H₄ |  | CH=CF₂ | H | H | F |
| CH₂=CHC₂H₄ |  | CH=CF₂ | F | H | F |
| CH₂=CHC₂H₄ |  | CH=CF₂ | F | F | F |
| CH₃CH=CHC₂H₄ |  | CH=CF₂ | H | H | F |
| CH₃CH=CHC₂H₄ |  | CH=CF₂ | F | H | F |
| CH₃CH=CHC₂H₄ |  | CH=CF₂ | F | F | F |
| CH₃ |  | OCHFCF₃ | H | H | F |
| CH₃ |  | OCHFCF₃ | F | H | F |
| CH₃ |  | OCHFCF₃ | F | F | F |
| C₂H₅ |  | OCHFCF₃ | H | H | F |
| C₂H₅ |  | OCHFCF₃ | F | H | F |
| C₂H₅ |  | OCHFCF₃ | F | F | F |
| n-C₃H₇ |  | OCHFCF₃ | H | H | F |

-continued

| R | —(A$^1$—Z$^1$)$_m$— | Y | L$^1$ | L$^2$ | L$^3$ |
|---|---|---|---|---|---|
| n-C$_3$H$_7$ | ⏣ | OCHFCF$_3$ | F | H | F |
| n-C$_3$H$_7$ | ⏣ | OCHFCF$_3$ | F | F | F |
| n-C$_5$H$_{11}$ | ⏣ | OCHFCF$_3$ | H | H | F |
| n-C$_5$H$_{11}$ | ⏣ | OCHFCF$_3$ | F | H | F |
| n-C$_5$H$_{11}$ | ⏣ | OCHFCF$_3$ | F | F | F |
| CH$_2$=CH | ⏣ | OCHFCF$_3$ | H | H | F |
| CH$_2$=CH | ⏣ | OCHFCF$_3$ | F | H | F |
| CH$_2$=CH | ⏣ | OCHFCF$_3$ | F | F | F |
| CH$_3$CH=CH | ⏣ | OCHFCF$_3$ | H | H | F |
| CH$_3$CH=CH | ⏣ | OCHFCF$_3$ | F | H | F |
| CH$_3$CH=CH | ⏣ | OCHFCF$_3$ | F | F | F |
| CH$_2$=CHC$_2$H$_4$ | ⏣ | OCHFCF$_3$ | H | H | F |
| CH$_2$=CHC$_2$H$_4$ | ⏣ | OCHFCF$_3$ | F | H | F |
| CH$_2$=CHC$_2$H$_4$ | ⏣ | OCHFCF$_3$ | F | F | F |
| CH$_3$CH=CHC$_2$H$_4$ | ⏣ | OCHFCF$_3$ | H | H | F |

-continued
| R | —(A¹—Z¹)ₘ— | Y | L¹ | L² | L³ |
|---|---|---|---|---|---|
| CH₃CH=CHC₂H₄ |  | OCHFCF₃ | F | H | F |
| CH₃CH=CHC₂H₄ |  | OCHFCF₃ | F | F | F |
| CH₃ |  | OCF₂CHFCF₃ | H | H | F |
| CH₃ |  | OCF₂CHFCF₃ | F | H | F |
| CH₃ |  | OCF₂CHFCF₃ | F | F | F |
| C₂H₅ |  | OCF₂CHFCF₃ | H | H | F |
| C₂H₅ |  | OCF₂CHFCF₃ | F | H | F |
| C₂H₅ |  | OCF₂CHFCF₃ | F | F | F |
| n-C₃H₇ |  | OCF₂CHFCF₃ | H | H | F |
| n-C₃H₇ |  | OCF₂CHFCF₃ | F | H | F |
| n-C₃H₇ |  | OCF₂CHFCF₃ | F | F | F |
| n-C₅H₁₁ |  | OCF₂CHFCF₃ | H | H | F |
| n-C₅H₁₁ |  | OCF₂CHFCF₃ | F | H | F |
| n-C₅H₁₁ |  | OCF₂CHFCF₃ | F | F | F |
| CH₂=CH |  | OCF₂CHFCF₃ | H | H | F |

-continued

| R | —(A¹—Z¹)ₘ— | Y | L¹ | L² | L³ |
|---|---|---|---|---|---|
| CH₂=CH | phenyl | OCF₂CHFCF₃ | F | H | F |
| CH₂=CH | phenyl | OCF₂CHFCF₃ | F | F | F |
| CH₃CH=CH | phenyl | OCF₂CHFCF₃ | H | H | F |
| CH₃CH=CH | phenyl | OCF₂CHFCF₃ | F | H | F |
| CH₃CH=CH | phenyl | OCF₂CHFCF₃ | F | F | F |
| CH₂=CHC₂H₄ | phenyl | OCF₂CHFCF₃ | H | H | F |
| CH₂=CHC₂H₄ | phenyl | OCF₂CHFCF₃ | F | H | F |
| CH₂=CHC₂H₄ | phenyl | OCF₂CHFCF₃ | F | F | F |
| CH₃CH=CHC₂H₄ | phenyl | OCF₂CHFCF₃ | H | H | F |
| CH₃CH=CHC₂H₄ | phenyl | OCF₂CHFCF₃ | F | H | F |
| CH₃CH=CHC₂H₄ | phenyl | OCF₂CHFCF₃ | F | F | F |
| CH₃ | cyclohexyl-CF₂O— | H | H | H | H |
| C₂H₅ | cyclohexyl-CF₂O— | H | H | H | H |
| n-C₃H₇ | cyclohexyl-CF₂O— | H | H | H | H |
| n-C₄H₉ | cyclohexyl-CF₂O— | H | H | H | H |

-continued
| R | —(A¹—Z¹)ₘ— | Y | L¹ | L² | L³ | |
|---|---|---|---|---|---|---|
| n-C₅H₁₁ | 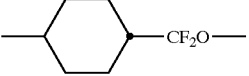 | H | H | H | H | |
| n-C₆H₁₃ | 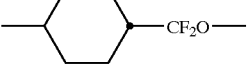 | H | H | H | H | |
| CH₃ | 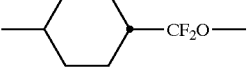 | F | H | H | H | |
| CH₃ | 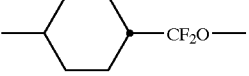 | F | F | H | H | |
| CH₃ | 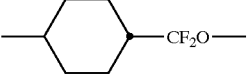 | F | F | F | H | |
| C₂H₅ | 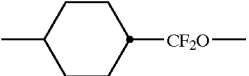 | F | H | H | H | |
| C₂H₅ | 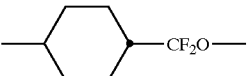 | F | F | H | H | |
| C₂H₅ | 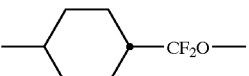 | F | F | F | H | |
| n-C₃H₇ | 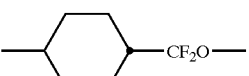 | F | H | H | H | |
| n-C₃H₇ | 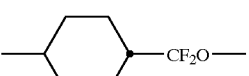 | F | F | H | H | |
| n-C₃H₇ | 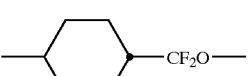 | F | F | F | H | C 86 N 120 I; Δn = 0.1526; Δε = 12.3 |
| n-C₅H₁₁ | 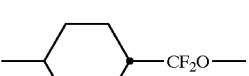 | F | H | H | H | |
| n-C₅H₁₁ | 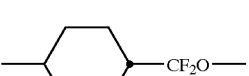 | F | F | H | H | |
| n-C₅H₁₁ | 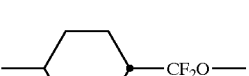 | F | F | F | H | |
| CH₂=CH | 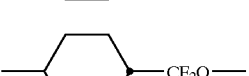 | F | H | H | H | |

-continued
| R | —(A¹—Z¹)ₘ— | Y | L¹ | L² | L³ |
|---|---|---|---|---|---|
| CH₂=CH | 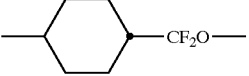 | F | F | H | H |
| CH₂=CH | 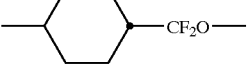 | F | F | F | H |
| CH₃CH=CH | 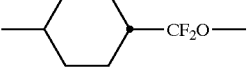 | F | H | H | H |
| CH₃CH=CH | 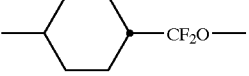 | F | F | H | H |
| CH₃CH=CH | 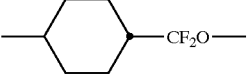 | F | F | F | H |
| CH₂=CHC₂H₄ | 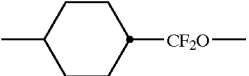 | F | H | H | H |
| CH₂=CHC₂H₄ | 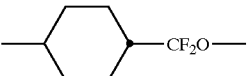 | F | F | H | H |
| CH₂=CHC₂H₄ | 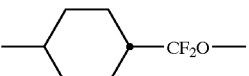 | F | F | F | H |
| CH₃CH=CHC₂H₄ | 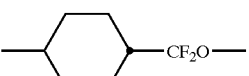 | F | H | H | H |
| CH₃CH=CHC₂H₄ | 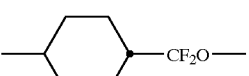 | F | F | H | H |
| CH₃CH=CHC₂H₄ | 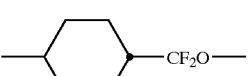 | F | F | F | H |
| CH₃ | 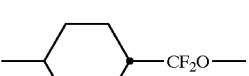 | OCF₃ | H | H | H |
| CH₃ | 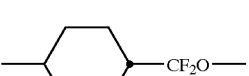 | OCF₃ | F | H | H |
| CH₃ | 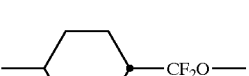 | OCF₃ | F | F | H |
| C₂H₅ | 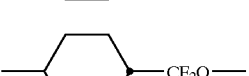 | OCF₃ | H | H | H |

-continued
| R | —(A¹—Z¹)ₘ— | Y | L¹ | L² | L³ |
|---|---|---|---|---|---|
| C₂H₅ | 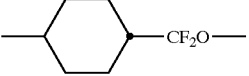 | OCF₃ | F | H | H |
| C₂H₅ | 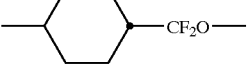 | OCF₃ | F | F | H |
| n-C₃H₇ | 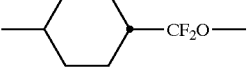 | OCF₃ | H | H | H |
| n-C₃H₇ | 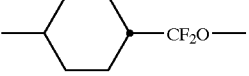 | OCF₃ | F | H | H |
| n-C₃H₇ | 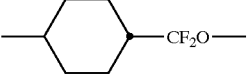 | OCF₃ | F | F | H |
| n-C₅H₁₁ | 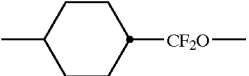 | OCF₃ | H | H | H |
| n-C₅H₁₁ | 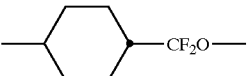 | OCF₃ | F | H | H |
| n-C₅H₁₁ | 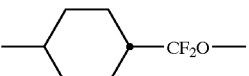 | OCF₃ | F | F | H |
| CH₂=CH | 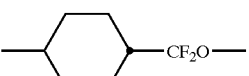 | OCF₃ | H | H | H |
| CH₂=CH | 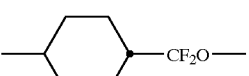 | OCF₃ | F | H | H |
| CH₂=CH | 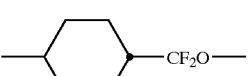 | OCF₃ | F | F | H |
| CH₃CH=CH | 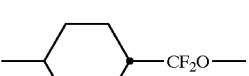 | OCF₃ | H | H | H |
| CH₃CH=CH | 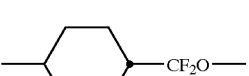 | OCF₃ | F | H | H |
| CH₃CH=CH | 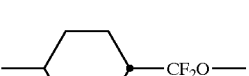 | OCF₃ | F | F | H |
| CH₂=CHC₂H₄ | 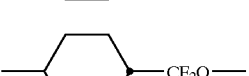 | OCF₃ | H | H | H |

-continued
| R | —(A¹—Z¹)ₘ— | Y | L¹ | L² | L³ |
|---|---|---|---|---|---|
| CH₂=CHC₂H₄ | 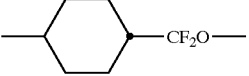 | OCF₃ | F | H | H |
| CH₂=CHC₂H₄ | 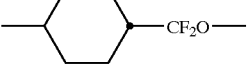 | OCF₃ | F | F | H |
| CH₃CH=CHC₂H₄ | 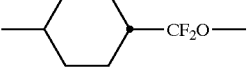 | OCF₃ | H | H | H |
| CH₃CH=CHC₂H₄ | 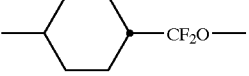 | OCF₃ | F | H | H |
| CH₃CH=CHC₂H₄ | 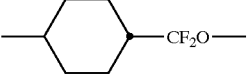 | OCF₃ | F | F | H |
| CH₃ | 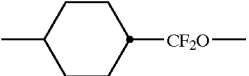 | CF₃ | H | H | H |
| CH₃ | 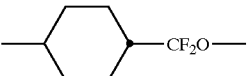 | CF₃ | F | H | H |
| CH₃ | 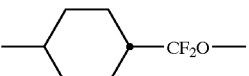 | CF₃ | F | F | H |
| C₂H₅ | 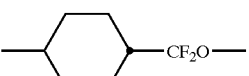 | CF₃ | H | H | H |
| C₂H₅ | 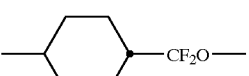 | CF₃ | F | H | H |
| C₂H₅ | 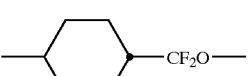 | CF₃ | F | F | H |
| n-C₃H₇ | 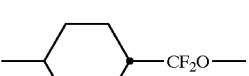 | CF₃ | H | H | H |
| n-C₃H₇ | 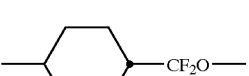 | CF₃ | F | H | H |
| n-C₃H₇ | 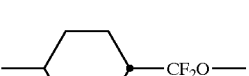 | CF₃ | F | F | H |
| n-C₅H₁₁ | 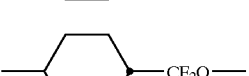 | CF₃ | H | H | H |

-continued
| R | —(A¹—Z¹)ₘ— | Y | L¹ | L² | L³ |
|---|---|---|---|---|---|
| n-C₅H₁₁ | 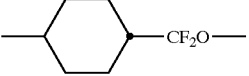 | CF₃ | F | H | H |
| n-C₅H₁₁ | 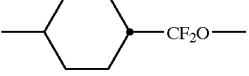 | CF₃ | F | F | H |
| CH₂=CH | 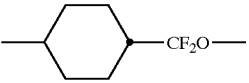 | CF₃ | H | H | H |
| CH₂=CH | 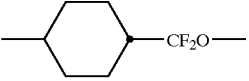 | CF₃ | F | H | H |
| CH₂=CH | 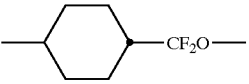 | CF₃ | F | F | H |
| CH₃CH=CH | 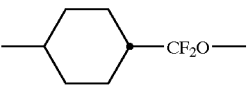 | CF₃ | H | H | H |
| CH₃CH=CH | 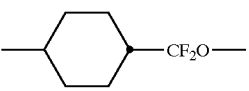 | CF₃ | F | H | H |
| CH₃CH=CH | 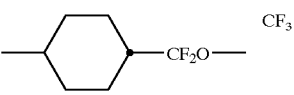 | CF₃ | F | F | H |
| CH₂=CHC₂H₄ | 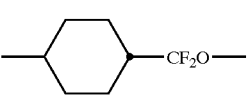 | CF₃ | H | H | H |
| CH₂=CHC₂H₄ | 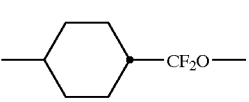 | CF₃ | F | H | H |
| CH₂=CHC₂H₄ | 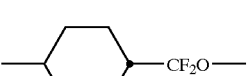 | CF₃ | F | F | H |
| CH₃CH=CHC₂H₄ | 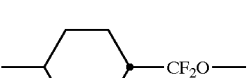 | CF₃ | H | H | H |
| CH₃CH=CHC₂H₄ | 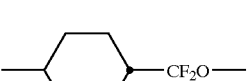 | CF₃ | F | H | H |
| CH₃CH=CHC₂H₄ |  | CF₃ | F | F | H |
| CH₃ |  | SF₅ | H | H | H |

-continued
| R | —(A¹—Z¹)ₘ— | Y | L¹ | L² | L³ |
|---|---|---|---|---|---|
| CH₃ | 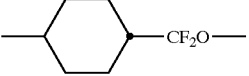 | SF₅ | F | H | H |
| CH₃ | 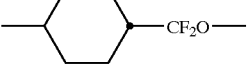 | SF₅ | F | F | H |
| C₂H₅ | 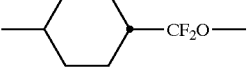 | SF₅ | H | H | H |
| C₂H₅ | 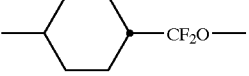 | SF₅ | F | H | H |
| C₂H₅ | 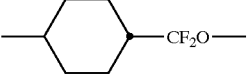 | SF₅ | F | F | H |
| n-C₃H₇ | 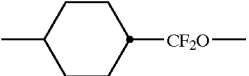 | SF₅ | H | H | H |
| n-C₃H₇ | 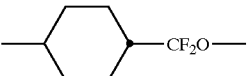 | SF₅ | F | H | H |
| n-C₃H₇ | 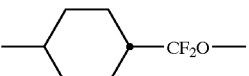 | SF₅ | F | F | H |
| n-C₅H₁₁ | 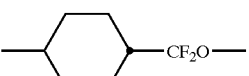 | SF₅ | H | H | H |
| n-C₅H₁₁ | 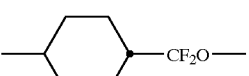 | SF₅ | F | H | H |
| n-C₅H₁₁ | 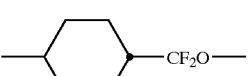 | SF₅ | F | F | H |
| CH₂=CH | 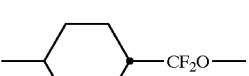 | SF₅ | H | H | H |
| CH₂=CH | 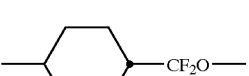 | SF₅ | F | H | H |
| CH₂=CH | 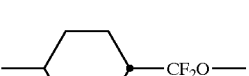 | SF₅ | F | F | H |
| CH₃CH=CH | 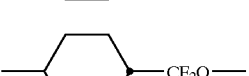 | SF₅ | H | H | H |

-continued
| R | —(A¹—Z¹)ₘ— | Y | L¹ | L² | L³ |
|---|---|---|---|---|---|
| CH₃CH=CH | 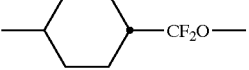 | SF₅ | F | H | H |
| CH₃CH=CH | 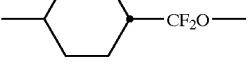 | SF₅ | F | F | H |
| CH₂=CHC₂H₄ | 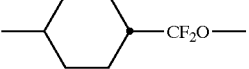 | SF₅ | H | H | H |
| CH₂=CHC₂H₄ | 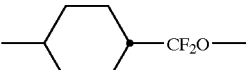 | SF₅ | F | H | H |
| CH₂=CHC₂H₄ | 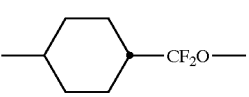 | SF₅ | F | F | H |
| CH₃CH=CHC₂H₄ | 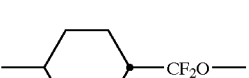 | SF₅ | H | H | H |
| CH₃CH=CHC₂H₄ | 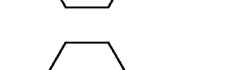 | SF₅ | F | H | H |
| CH₃CH=CHC₂H₄ | 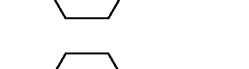 | SF₅ | F | F | H |
| CH₃ | 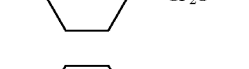 | CH=CF₂ | H | H | H |
| CH₃ | 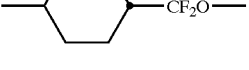 | CH=CF₂ | F | H | H |
| CH₃ | 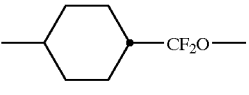 | CH=CF₂ | F | F | H |
| C₂H₅ | 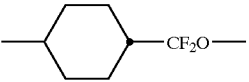 | CH=CF₂ | H | H | H |
| C₂H₅ | 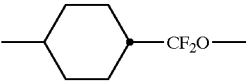 | CH=CF₂ | F | H | H |
| C₂H₅ | 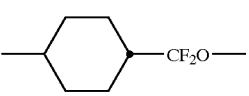 | CH=CF₂ | F | F | H |
| n-C₃H₇ | 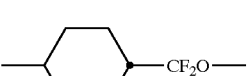 | CH=CF₂ | H | H | H |

-continued
| R | —(A¹—Z¹)ₘ— | Y | L¹ | L² | L³ |
|---|---|---|---|---|---|
| n-C₃H₇ |  | CH=CF₂ | F | H | H |
| n-C₃H₇ | 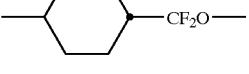 | CH=CF₂ | F | F | H |
| n-C₅H₁₁ | 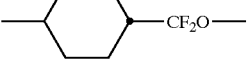 | CH=CF₂ | H | H | H |
| n-C₅H₁₁ | 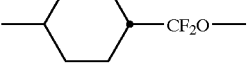 | CH=CF₂ | F | H | H |
| n-C₅H₁₁ | 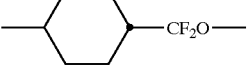 | CH=CF₂ | F | F | H |
| CH₂=CH | 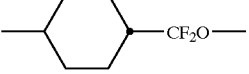 | CH=CF₂ | H | H | H |
| CH₂=CH | 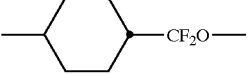 | CH=CF₂ | F | H | H |
| CH₂=CH | 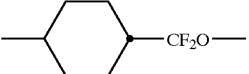 | CH=CF₂ | F | F | H |
| CH₃CH=CH | 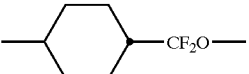 | CH=CF₂ | H | H | H |
| CH₃CH=CH | 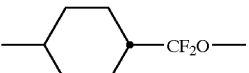 | CH=CF₂ | F | H | H |
| CH₃CH=CH | 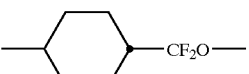 | CH=CF₂ | F | F | H |
| CH₂=CHC₂H₄ | 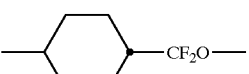 | CH=CF₂ | H | H | H |
| CH₂=CHC₂H₄ | 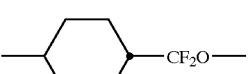 | CH=CF₂ | F | H | H |
| CH₂=CHC₂H₄ | 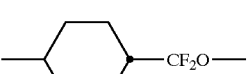 | CH=CF₂ | F | F | H |
| CH₃CH=CHC₂H₄ | 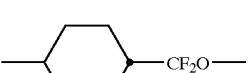 | CH=CF₂ | H | H | H |

-continued

| R | —(A¹—Z¹)ₘ— | Y | L¹ | L² | L³ |
|---|---|---|---|---|---|
| CH₃CH=CHC₂H₄ | –⟨cyclohexyl⟩–CF₂O– | CH=CF₂ | F | H | H |
| CH₃CH=CHC₂H₄ | –⟨cyclohexyl⟩–CF₂O– | CH=CF₂ | F | F | H |
| CH₃ | –⟨cyclohexyl⟩–CF₂O– | OCHFCF₃ | H | H | H |
| CH₃ | –⟨cyclohexyl⟩–CF₂O– | OCHFCF₃ | F | H | H |
| CH₃ | –⟨cyclohexyl⟩–CF₂O– | OCHFCF₃ | F | F | H |
| C₂H₅ | –⟨cyclohexyl⟩–CF₂O– | OCHFCF₃ | H | H | H |
| C₂H₅ | –⟨cyclohexyl⟩–CF₂O– | OCHFCF₃ | F | H | H |
| C₂H₅ | –⟨cyclohexyl⟩–CF₂O– | OCHFCF₃ | F | F | H |
| n-C₃H₇ | –⟨cyclohexyl⟩–CF₂O– | OCHFCF₃ | H | H | H |
| n-C₃H₇ | –⟨cyclohexyl⟩–CF₂O– | OCHFCF₃ | F | H | H |
| n-C₃H₇ | –⟨cyclohexyl⟩–CF₂O– | OCHFCF₃ | F | F | H |
| n-C₅H₁₁ | –⟨cyclohexyl⟩–CF₂O– | OCHFCF₃ | H | H | H |
| n-C₅H₁₁ | –⟨cyclohexyl⟩–CF₂O– | OCHFCF₃ | F | H | H |
| n-C₅H₁₁ | –⟨cyclohexyl⟩–CF₂O– | OCHFCF₃ | F | F | H |
| CH₂=CH | –⟨cyclohexyl⟩–CF₂O– | OCHFCF₃ | H | H | H |

-continued

| R | —(A¹—Z¹)ₘ— | Y | L¹ | L² | L³ |
|---|---|---|---|---|---|
| CH₂=CH | —Cy—CF₂O— | OCHFCF₃ | F | H | H |
| CH₂=CH | —Cy—CF₂O— | OCHFCF₃ | F | F | H |
| CH₃CH=CH | —Cy—CF₂O— | OCHFCF₃ | H | H | H |
| CH₃CH=CH | —Cy—CF₂O— | OCHFCF₃ | F | H | H |
| CH₃CH=CH | —Cy—CF₂O— | OCHFCF₃ | F | F | H |
| CH₂=CHC₂H₄ | —Cy—CF₂O— | OCHFCF₃ | H | H | H |
| CH₂=CHC₂H₄ | —Cy—CF₂O— | OCHFCF₃ | F | H | H |
| CH₂=CHC₂H₄ | —Cy—CF₂O— | OCHFCF₃ | F | F | H |
| CH₃CH=CHC₂H₄ | —Cy—CF₂O— | OCHFCF₃ | H | H | H |
| CH₃CH=CHC₂H₄ | —Cy—CF₂O— | OCHFCF₃ | F | H | H |
| CH₃CH=CHC₂H₄ | —Cy—CF₂O— | OCHFCF₃ | F | F | H |
| CH₃ | —Cy—CF₂O— | OCF₂CHFCF₃ | H | H | H |
| CH₃ | —Cy—CF₂O— | OCF₂CHFCF₃ | F | H | H |
| CH₃ | —Cy—CF₂O— | OCF₂CHFCF₃ | F | F | H |
| C₂H₅ | —Cy—CF₂O— | OCF₂CHFCF₃ | H | H | H |

-continued

| R | —(A¹—Z¹)ₘ— | Y | L¹ | L² | L³ |
|---|---|---|---|---|---|
| C₂H₅ | —⟨cyclohexyl⟩—CF₂O— | OCF₂CHFCF₃ | F | H | H |
| C₂H₅ | —⟨cyclohexyl⟩—CF₂O— | OCF₂CHFCF₃ | F | F | H |
| n-C₃H₇ | —⟨cyclohexyl⟩—CF₂O— | OCF₂CHFCF₃ | H | H | H |
| n-C₃H₇ | —⟨cyclohexyl⟩—CF₂O— | OCF₂CHFCF₃ | F | H | H |
| n-C₃H₇ | —⟨cyclohexyl⟩—CF₂O— | OCF₂CHFCF₃ | F | F | H |
| n-C₅H₁₁ | —⟨cyclohexyl⟩—CF₂O— | OCF₂CHFCF₃ | H | H | H |
| n-C₅H₁₁ | —⟨cyclohexyl⟩—CF₂O— | OCF₂CHFCF₃ | F | H | H |
| n-C₅H₁₁ | —⟨cyclohexyl⟩—CF₂O— | OCF₂CHFCF₃ | F | F | H |
| CH₂=CH | —⟨cyclohexyl⟩—CF₂O— | OCF₂CHFCF₃ | H | H | H |
| CH₂=CH | —⟨cyclohexyl⟩—CF₂O— | OCF₂CHFCF₃ | F | H | H |
| CH₂=CH | —⟨cyclohexyl⟩—CF₂O— | OCF₂CHFCF₃ | F | F | H |
| CH₃CH=CH | —⟨cyclohexyl⟩—CF₂O— | OCF₂CHFCF₃ | H | H | H |
| CH₃CH=CH | —⟨cyclohexyl⟩—CF₂O— | OCF₂CHFCF₃ | F | H | H |
| CH₃CH=CH | —⟨cyclohexyl⟩—CF₂O— | OCF₂CHFCF₃ | F | F | H |
| CH₂=CHC₂H₄ | —⟨cyclohexyl⟩—CF₂O— | OCF₂CHFCF₃ | H | H | H |

-continued

| R | —(A¹—Z¹)ₘ— | Y | L¹ | L² | L³ |
|---|---|---|---|---|---|
| CH₂=CHC₂H₄ | cyclohexyl-CF₂O— | OCF₂CHFCF₃ | F | H | H |
| CH₂=CHC₂H₄ | cyclohexyl-CF₂O— | OCF₂CHFCF₃ | F | F | H |
| CH₃CH=CHC₂H₄ | cyclohexyl-CF₂O— | OCF₂CHFCF₃ | H | H | H |
| CH₃CH=CHC₂H₄ | cyclohexyl-CF₂O— | OCF₂CHFCF₃ | F | H | H |
| CH₃CH=CHC₂H₄ | cyclohexyl-CF₂O— | OCF₂CHFCF₃ | F | F | H |
| CH₃ | cyclohexyl-CF₂O— | H | H | H | F |
| C₂H₅ | cyclohexyl-CF₂O— | H | H | H | F |
| n-C₃H₇ | cyclohexyl-CF₂O— | H | H | H | F |
| n-C₄H₉ | cyclohexyl-CF₂O— | H | H | H | F |
| n-C₅H₁₁ | cyclohexyl-CF₂O— | H | H | H | F |
| n-C₆H₁₃ | cyclohexyl-CF₂O— | H | H | H | F |
| CH₃ | cyclohexyl-CF₂O— | F | H | H | F |
| CH₃ | cyclohexyl-CF₂O— | F | F | H | F |
| CH₃ | cyclohexyl-CF₂O— | F | F | F | F |
| C₂H₅ | cyclohexyl-CF₂O— | F | H | H | F |

-continued
| R | —(A¹—Z¹)ₘ— | Y | L¹ | L² | L³ |
|---|---|---|---|---|---|
| C₂H₅ | 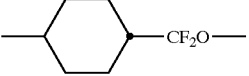 | F | F | H | F |
| C₂H₅ | 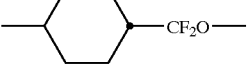 | F | F | F | F |
| n-C₃H₇ | 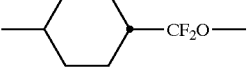 | F | H | H | F |
| n-C₃H₇ | 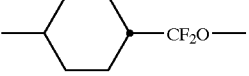 | F | F | H | F |
| n-C₅H₁₁ | 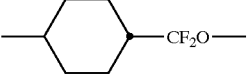 | F | H | H | F |
| n-C₅H₁₁ | 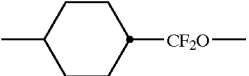 | F | F | H | F |
| n-C₅H₁₁ | 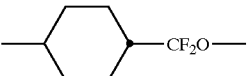 | F | F | F | F |
| CH₂=CH | 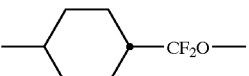 | F | H | H | F |
| CH₂=CH | 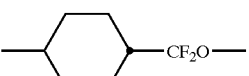 | F | F | H | F |
| CH₂=CH | 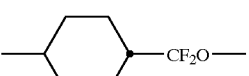 | F | F | F | F |
| CH₃CH=CH | 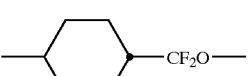 | F | H | H | F |
| CH₃CH=CH | 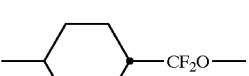 | F | F | H | F |
| CH₃CH=CH | 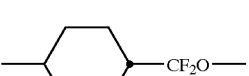 | F | F | F | F |
| CH₂=CHC₂H₄ | 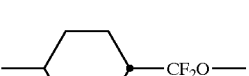 | F | H | H | F |
| CH₂=CHC₂H₄ | 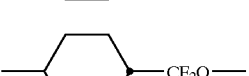 | F | F | H | F |

-continued
| R | —(A¹—Z¹)ₘ— | Y | L¹ | L² | L³ |
|---|---|---|---|---|---|
| CH₂=CHC₂H₄ | 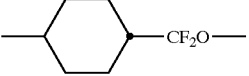—CF₂O— | F | F | F | F |
| CH₃CH=CHC₂H₄ | 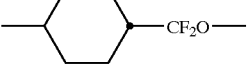—CF₂O— | F | H | H | F |
| CH₃CH=CHC₂H₄ | 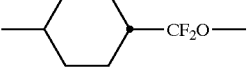—CF₂O— | F | F | H | F |
| CH₃CH=CHC₂H₄ | 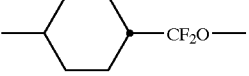—CF₂O— | F | F | F | F |
| CH₃ | 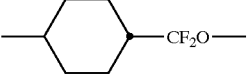—CF₂O— | OCF₃ | H | H | F |
| CH₃ | 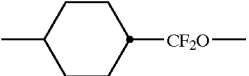—CF₂O— | OCF₃ | F | H | F |
| CH₃ | 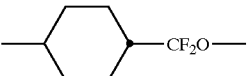—CF₂O— | OCF₃ | F | F | F |
| C₂H₅ | 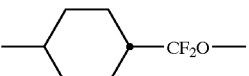—CF₂O— | OCF₃ | H | H | F |
| C₂H₅ | 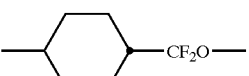—CF₂O— | OCF₃ | F | H | F |
| C₂H₅ | 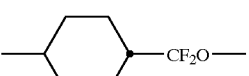—CF₂O— | OCF₃ | F | F | F |
| n-C₃H₇ | 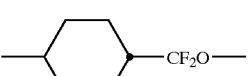—CF₂O— | OCF₃ | H | H | F |
| n-C₃H₇ | 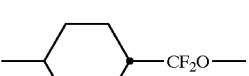—CF₂O— | OCF₃ | F | H | F |
| n-C₃H₇ | 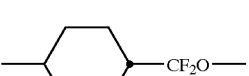—CF₂O— | OCF₃ | F | F | F |
| n-C₅H₁₁ | 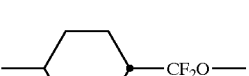—CF₂O— | OCF₃ | H | H | F |
| n-C₅H₁₁ | 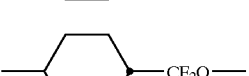—CF₂O— | OCF₃ | F | H | F |

-continued
| R | —(A¹—Z¹)ₘ— | Y | L¹ | L² | L³ |
|---|---|---|---|---|---|
| n-C₅H₁₁ | 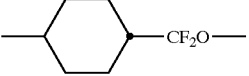 | OCF₃ | F | F | F |
| CH₂=CH | 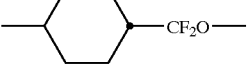 | OCF₃ | H | H | F |
| CH₂=CH | 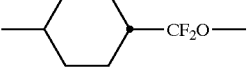 | OCF₃ | F | H | F |
| CH₂=CH | 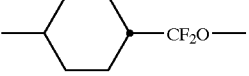 | OCF₃ | F | F | F |
| CH₃CH=CH | 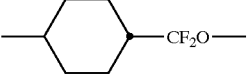 | OCF₃ | H | H | F |
| CH₃CH=CH | 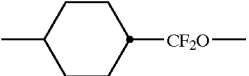 | OCF₃ | F | H | F |
| CH₃CH=CH | 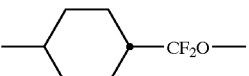 | OCF₃ | F | F | F |
| CH₂=CHC₂H₄ | 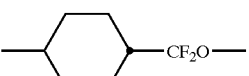 | OCF₃ | H | H | F |
| CH₂=CHC₂H₄ | 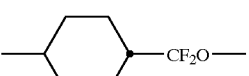 | OCF₃ | F | H | F |
| CH₂=CHC₂H₄ | 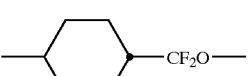 | OCF₃ | F | F | F |
| CH₃CH=CHC₂H₄ | 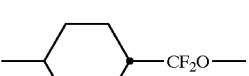 | OCF₃ | H | H | F |
| CH₃CH=CHC₂H₄ | 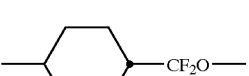 | OCF₃ | F | H | F |
| CH₃CH=CHC₂H₄ | 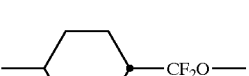 | OCF₃ | F | F | F |
| CH₃ | 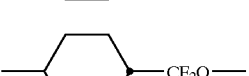 | CF₃ | H | H | F |
| CH₃ |  | CF₃ | F | H | F |

-continued
| R | —(A¹—Z¹)ₘ— | Y | L¹ | L² | L³ |
|---|---|---|---|---|---|
| CH₃ | 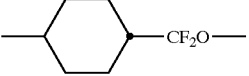 | CF₃ | F | F | F |
| C₂H₅ | 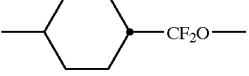 | CF₃ | H | H | F |
| C₂H₅ | 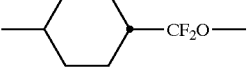 | CF₃ | F | H | F |
| C₂H₅ | 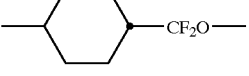 | CF₃ | F | F | F |
| n-C₃H₇ | 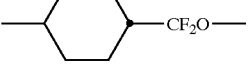 | CF₃ | H | H | F |
| n-C₃H₇ | 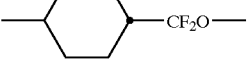 | CF₃ | F | H | F |
| n-C₃H₇ | 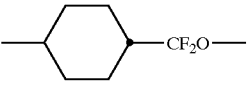 | CF₃ | F | F | F |
| n-C₅H₁₁ | 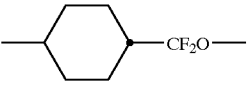 | CF₃ | H | H | F |
| n-C₅H₁₁ | 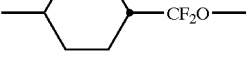 | CF₃ | F | H | F |
| n-C₅H₁₁ | 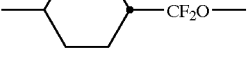 | CF₃ | F | F | F |
| CH₂=CH | 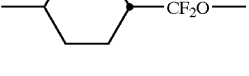 | CF₃ | H | H | F |
| CH₂=CH | 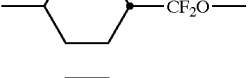 | CF₃ | F | H | F |
| CH₂=CH |  | CF₃ | F | F | F |
| CH₃CH=CH | 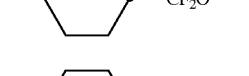 | CF₃ | H | H | F |
| CH₃CH=CH | 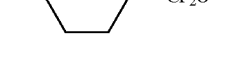 | CF₃ | F | H | F |

-continued
| R | —(A¹—Z¹)ₘ— | Y | L¹ | L² | L³ |
|---|---|---|---|---|---|
| CH₃CH=CH | 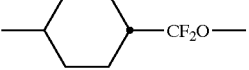 | CF₃ | F | F | F |
| CH₂=CHC₂H₄ | 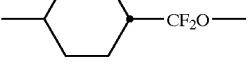 | CF₃ | H | H | F |
| CH₂=CHC₂H₄ | 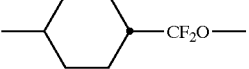 | CF₃ | F | H | F |
| CH₂=CHC₂H₄ | 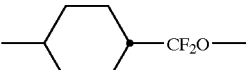 | CF₃ | F | F | F |
| CH₃CH=CHC₂H₄ | 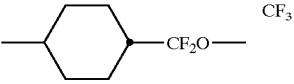 | CF₃ | H | H | F |
| CH₃CH=CHC₂H₄ | 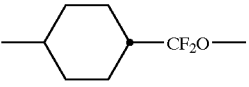 | CF₃ | F | H | F |
| CH₃CH=CHC₂H₄ | 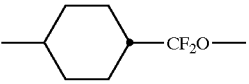 | CF₃ | F | F | F |
| CH₃ | 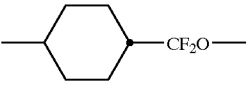 | SF₅ | H | H | F |
| CH₃ | 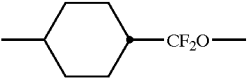 | SF₅ | F | H | F |
| CH₃ | 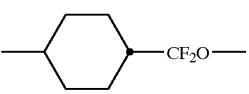 | SF₅ | F | F | F |
| C₂H₅ | 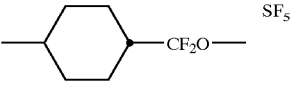 | SF₅ | H | H | F |
| C₂H₅ | 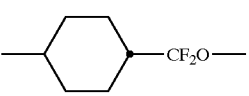 | SF₅ | F | H | F |
| C₂H₅ | 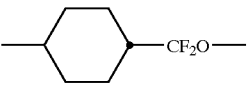 | SF₅ | F | F | F |
| n-C₃H₇ | 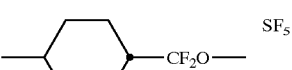 | SF₅ | H | H | F |
| n-C₃H₇ | 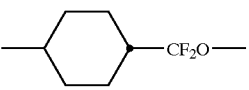 | SF₅ | F | H | F |

-continued
| R | —(A¹—Z¹)ₘ— | Y | L¹ | L² | L³ |
|---|---|---|---|---|---|
| n-C₃H₇ |  | SF₅ | F | F | F |
| n-C₅H₁₁ | 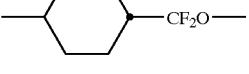 | SF₅ | H | H | F |
| n-C₅H₁₁ | 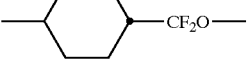 | SF₅ | F | H | F |
| n-C₅H₁₁ | 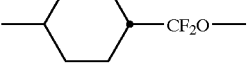 | SF₅ | F | F | F |
| CH₂=CH | 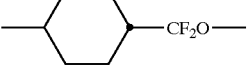 | SF₅ | H | H | F |
| CH₂=CH | 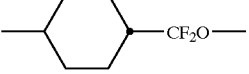 | SF₅ | F | H | F |
| CH₂=CH | 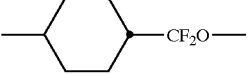 | SF₅ | F | F | F |
| CH₃CH=CH | 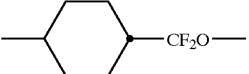 | SF₅ | H | H | F |
| CH₃CH=CH | 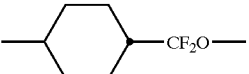 | SF₅ | F | H | F |
| CH₃CH=CH | 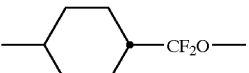 | SF₅ | F | F | F |
| CH₂=CHC₂H₄ | 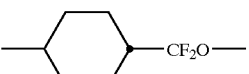 | SF₅ | H | H | F |
| CH₂=CHC₂H₄ | 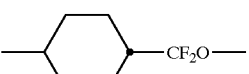 | SF₅ | F | H | F |
| CH₂=CHC₂H₄ | 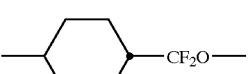 | SF₅ | F | F | F |
| CH₃CH=CHC₂H₄ | 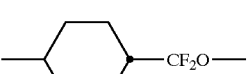 | SF₅ | H | H | F |
| CH₃CH=CHC₂H₄ | 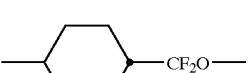 | SF₅ | F | H | F |

-continued
| R | —(A¹—Z¹)ₘ— | Y | L¹ | L² | L³ |
|---|---|---|---|---|---|
| CH₃CH=CHC₂H₄ | 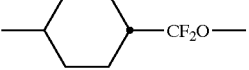 | SF₅ | F | F | F |
| CH₃ | 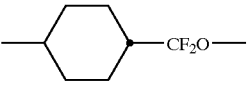 | CH=CF₂ | H | H | F |
| CH₃ | 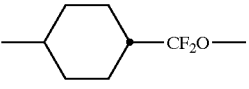 | CH=CF₂ | F | H | F |
| CH₃ | 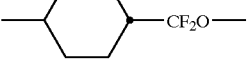 | CH=CF₂ | F | F | F |
| C₂H₅ | 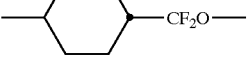 | CH=CF₂ | H | H | F |
| C₂H₅ | 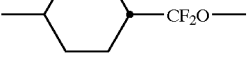 | CH=CF₂ | F | H | F |
| C₂H₅ | 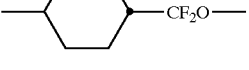 | CH=CF₂ | F | F | F |
| n-C₃H₇ | 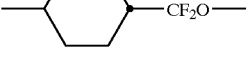 | CH=CF₂ | H | H | F |
| n-C₃H₇ | 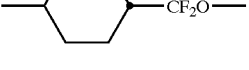 | CH=CF₂ | F | H | F |
| n-C₃H₇ | 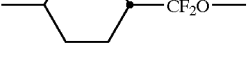 | CH=CF₂ | F | F | F |
| n-C₅H₁₁ | 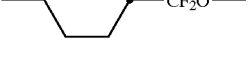 | CH=CF₂ | H | H | F |
| n-C₅H₁₁ | 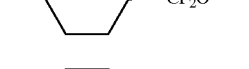 | CH=CF₂ | F | H | F |
| n-C₅H₁₁ | 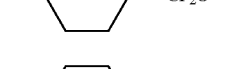 | CH=CF₂ | F | F | F |
| CH₂=CH | 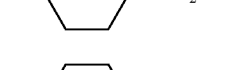 | CH=CF₂ | H | H | F |
| CH₂=CH | 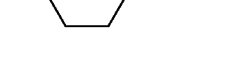 | CH=CF₂ | F | H | F |

-continued

| R | —(A¹—Z¹)ₘ— | Y | L¹ | L² | L³ |
|---|---|---|---|---|---|
| CH₂=CH | —⌬—CF₂O— | CH=CF₂ | F | F | F |
| CH₃CH=CH | —⌬—CF₂O— | CH=CF₂ | H | H | F |
| CH₃CH=CH | —⌬—CF₂O— | CH=CF₂ | F | H | F |
| CH₃CH=CH | —⌬—CF₂O— | CH=CF₂ | F | F | F |
| CH₂=CHC₂H₄ | —⌬—CF₂O— | CH=CF₂ | H | H | F |
| CH₂=CHC₂H₄ | —⌬—CF₂O— | CH=CF₂ | F | H | F |
| CH₂=CHC₂H₄ | —⌬—CF₂O— | CH=CF₂ | F | F | F |
| CH₃CH=CHC₂H₄ | —⌬—CF₂O— | CH=CF₂ | H | H | F |
| CH₃CH=CHC₂H₄ | —⌬—CF₂O— | CH=CF₂ | F | H | F |
| CH₃CH=CHC₂H₄ | —⌬—CF₂O— | CH=CF₂ | F | F | F |
| CH₃ | —⌬—CF₂O— | OCHFCF₃ | H | H | F |
| CH₃ | —⌬—CF₂O— | OCHFCF₃ | F | H | F |
| CH₃ | —⌬—CF₂O— | OCHFCF₃ | F | F | F |
| C₂H₅ | —⌬—CF₂O— | OCHFCF₃ | H | H | F |
| C₂H₅ | —⌬—CF₂O— | OCHFCF₃ | F | H | F |

-continued

| R | —(A¹—Z¹)ₘ— | Y | L¹ | L² | L³ |
|---|---|---|---|---|---|
| C₂H₅ | cyclohexyl-CF₂O— | OCHFCF₃ | F | F | F |
| n-C₃H₇ | cyclohexyl-CF₂O— | OCHFCF₃ | H | H | F |
| n-C₃H₇ | cyclohexyl-CF₂O— | OCHFCF₃ | F | H | F |
| n-C₃H₇ | cyclohexyl-CF₂O— | OCHFCF₃ | F | F | F |
| n-C₅H₁₁ | cyclohexyl-CF₂O— | OCHFCF₃ | H | H | F |
| n-C₅H₁₁ | cyclohexyl-CF₂O— | OCHFCF₃ | F | H | F |
| n-C₅H₁₁ | cyclohexyl-CF₂O— | OCHFCF₃ | F | F | F |
| CH₂=CH | cyclohexyl-CF₂O— | OCHFCF₃ | H | H | F |
| CH₂=CH | cyclohexyl-CF₂O— | OCHFCF₃ | F | H | F |
| CH₂=CH | cyclohexyl-CF₂O— | OCHFCF₃ | F | F | F |
| CH₂=CH | (H)cyclohexyl-CF₂O— | OCHFCF₃ | F | F | F |
| CH₃CH=CH | (H)cyclohexyl-CF₂O— | OCHFCF₃ | H | H | F |
| CH₃CH=CH | (H)cyclohexyl-CF₂O— | OCHFCF₃ | F | H | F |
| CH₃CH=CH | (H)cyclohexyl-CF₂O— | OCHFCF₃ | F | F | F |
| CH₂=CHC₂H₄ | (H)cyclohexyl-CF₂O— | OCHFCF₃ | H | H | F |

-continued

| R | —(A¹—Z¹)ₘ— | Y | L¹ | L² | L³ |
|---|---|---|---|---|---|
| CH₂=CHC₂H₄ | —[Cy(H)]—CF₂O— | OCHFCF₃ | F | H | F |
| CH₂=CHC₂H₄ | —[Cy(H)]—CF₂O— | OCHFCF₃ | F | F | F |
| CH₃CH=CHC₂H₄ | —[Cy(H)]—CF₂O— | OCHFCF₃ | H | H | F |
| CH₃CH=CHC₂H₄ | —[Cy(H)]—CF₂O— | OCHFCF₃ | F | H | F |
| CH₃CH=CHC₂H₄ | —[Cy(H)]—CF₂O— | OCHFCF₃ | F | F | F |
| CH₃ | —[Cy(H)]—CF₂O— | OCF₂CHFCF₃ | H | H | F |
| CH₃ | —[Cy(H)]—CF₂O— | OCF₂CHFCF₃ | F | H | F |
| CH₃ | —[Cy(H)]—CF₂O— | OCF₂CHFCF₃ | F | F | F |
| C₂H₅ | —[Cy(H)]—CF₂O— | OCF₂CHFCF₃ | H | H | F |
| C₂H₅ | —[Cy(H)]—CF₂O— | OCF₂CHFCF₃ | F | H | F |
| C₂H₅ | —[Cy(H)]—CF₂O— | OCF₂CHFCF₃ | F | F | F |
| n-C₃H₇ | —[Cy(H)]—CF₂O— | OCF₂CHFCF₃ | H | H | F |
| n-C₃H₇ | —[Cy(H)]—CF₂O— | OCF₂CHFCF₃ | F | H | F |
| n-C₃H₇ | —[Cy(H)]—CF₂O— | OCF₂CHFCF₃ | F | F | F |
| n-C₅H₁₁ | —[Cy(H)]—CF₂O— | OCF₂CHFCF₃ | H | H | F |

-continued

| R | —(A¹—Z¹)ₘ— | Y | L¹ | L² | L³ | |
|---|---|---|---|---|---|---|
| n-C₅H₁₁ | —[Cy(H)]—CF₂O— | OCF₂CHFCF₃ | F | H | F | |
| n-C₅H₁₁ | —[Cy(H)]—CF₂O— | OCF₂CHFCF₃ | F | F | F | |
| CH₂=CH | —[Cy(H)]—CF₂O— | OCF₂CHFCF₃ | H | H | F | |
| CH₂=CH | —[Cy(H)]—CF₂O— | OCF₂CHFCF₃ | F | H | F | |
| CH₂=CH | —[Cy(H)]—CF₂O— | OCF₂CHFCF₃ | F | F | F | |
| CH₃CH=CH | —[Cy(H)]—CF₂O— | OCF₂CHFCF₃ | H | H | F | |
| CH₃CH=CH | —[Cy(H)]—CF₂O— | OCF₂CHFCF₃ | F | H | F | |
| CH₃CH=CH | —[Cy(H)]—CF₂O— | OCF₂CHFCF₃ | F | F | F | |
| CH₂=CHC₂H₄ | —[Cy(H)]—CF₂O— | OCF₂CHFCF₃ | H | H | F | |
| CH₂=CHC₂H₄ | —[Cy(H)]—CF₂O— | OCF₂CHFCF₃ | F | H | F | |
| CH₂=CHC₂H₄ | —[Cy(H)]—CF₂O— | OCF₂CHFCF₃ | F | F | F | |
| CH₃CH=CHC₂H₄ | —[Cy(H)]—CF₂O— | OCF₂CHFCF₃ | H | H | F | |
| CH₃CH=CHC₂H₄ | —[Cy(H)]—CF₂O— | OCF₂CHFCF₃ | F | H | F | |
| CH₃CH=CHC₂H₄ | —[Cy(H)]—CF₂O— | OCF₂CHFCF₃ | F | F | F | |
| CH₃O | — | F | F | F | H | |
| C₂H₅O | — | F | F | F | H | |
| n-C₃H₇O | — | F | F | F | H | C 112 I |

-continued

| R | —(A¹—Z¹)ₘ— | Y | L¹ | L² | L³ | |
|---|---|---|---|---|---|---|
| n-C₄H₉O | — | F | F | F | H | C 75 I; $\Delta n = 0.1666$; $\Delta \epsilon = 14.1$ |
| n-C₅H₁₁O | — | F | F | F | H | |
| n-C₆H₁₃O | — | F | F | F | H | |
| CH₂=CHCH₂O | — | F | F | F | H | C 95 I; $\Delta n = 0.1291$; $\gamma_1 = 15.3$ |
| CH₃ | — | F | H | H | H | |
| CH₃ | — | F | F | H | H | |
| CH₃ | — | F | F | F | H | C 90 I; $\Delta n = 0.1550$; $\Delta \epsilon = 15.1$ |
| C₂H₅ | — | F | H | H | H | |
| C₂H₅ | — | F | F | H | H | |
| C₂H₅ | — | F | F | F | H | C 83 I |
| n-C₃H₇ | — | F | H | H | H | |
| n-C₃H₇ | — | F | F | H | H | |
| n-C₃H₇ | — | F | F | F | H | C 76 I; $\Delta n = 0.1415$; $\Delta \epsilon = 12.2$ |
| n-C₅H₁₁ | — | F | H | H | H | |
| n-C₅H₁₁ | — | F | F | H | H | |
| n-C₅H₁₁ | — | F | F | F | H | C 63 I; $\Delta n = 0.1323$; $\Delta \epsilon = 11.0$ |
| CH₂=CH | — | F | H | H | H | |
| CH₂=CH | — | F | F | H | H | |
| CH₂=CH | — | F | F | F | H | |
| CH₃CH=CH | — | F | H | H | H | |
| CH₃CH=CH | — | F | F | H | H | |
| CH₃CH=CH | — | F | F | F | H | |
| CH₂=CHC₂H₄ | — | F | H | H | H | |
| CH₂=CHC₂H₄ | — | F | F | H | H | |
| CH₂=CHC₂H₄ | — | F | F | F | H | C 87 I; $\Delta n = 0.1430$; $\Delta \epsilon = 8.5$ |
| CH₃CH=CHC₂H₄ | — | F | H | H | H | |
| CH₃CH=CHC₂H₄ | — | F | F | H | H | |
| CH₃CH=CHC₂H₄ | — | F | F | F | H | |
| CH₃ | OCF₃ | H | H | H | | |
| CH₃ | OCF₃ | F | H | H | | C 101 $S_A(88)$ I; $\Delta n = 0.1662$; $\Delta \epsilon = 15.6$ |

-continued

| R | —(A¹—Z¹)ₘ— | Y | L¹ | L² | L³ | |
|---|---|---|---|---|---|---|
| CH₃ | — | OCF₃ | F | F | H | C 158 I |
| C₂H₅ | — | OCF₃ | H | H | H | |
| C₂H₅ | — | OCF₃ | F | H | H | C 114 I; $\Delta n = 0.1533$; $\Delta\epsilon = 13.6$ |
| C₂H₅ | — | OCF₃ | F | F | H | C 148 I |
| n-C₃H₇ | — | OCF₃ | H | H | H | |
| n-C₃H₇ | — | OCF₃ | F | H | H | C 101 I; $\Delta n = 0.1590$; $\Delta\epsilon = 13.0$ |
| n-C₃H₇ | — | OCF₃ | F | F | H | C 124 I |
| n-C₅H₁₁ | — | OCF₃ | H | H | H | |
| n-C₅H₁₁ | — | OCF₃ | F | H | H | |
| n-C₅H₁₁ | — | OCF₃ | F | F | H | |
| CH₂=CH | — | OCF₃ | H | H | H | |
| CH₂=CH | — | OCF₃ | F | H | H | |
| CH₂=CH | — | OCF₃ | F | F | H | |
| CH₃CH=CH | — | OCF₃ | H | H | H | |
| CH₃CH=CH | — | OCF₃ | F | H | H | |
| CH₃CH=CH | — | OCF₃ | F | F | H | |
| CH₂=CHC₂H₄ | — | OCF₃ | H | H | H | |
| CH₂=CHC₂H₄ | — | OCF₃ | F | F | H | |
| CH₃CH=CHC₂H₄ | — | OCF₃ | H | H | H | |
| CH₃CH=CHC₂H₄ | — | OCF₃ | F | H | H | |
| CH₃CH=CHC₂H₄ | — | OCF₃ | F | F | H | |
| CH₃ | — | CF₃ | H | H | H | |
| CH₃ | — | CF₃ | F | H | H | |
| CH₃ | — | CF₃ | F | F | H | |
| C₂H₅ | — | CF₃ | H | H | H | |
| C₂H₅ | — | CF₃ | F | H | H | |
| C₂H₅ | — | CF₃ | F | F | H | |
| n-C₃H₇ | — | CF₃ | H | H | H | |
| n-C₃H₇ | — | CF₃ | F | H | H | |
| n-C₃H₇ | — | CF₃ | F | F | H | |
| n-C₅H₁₁ | — | CF₃ | H | H | H | |
| n-C₅H₁₁ | — | CF₃ | F | H | H | |
| n-C₅H₁₁ | — | CF₃ | F | F | H | |
| CH₂=CH | — | CF₃ | H | H | H | |
| CH₂=CH | — | CF₃ | F | H | H | |
| CH₂=CH | — | CF₃ | F | F | H | |

-continued

| R | —(A¹—Z¹)ₘ— | Y | L¹ | L² | L³ |
|---|---|---|---|---|---|
| CH₃CH=CH | — | CF₃ | H | H | H |
| CH₃CH=CH | — | CF₃ | F | H | H |
| CH₃CH=CH | — | CF₃ | F | F | H |
| CH₂=CHC₂H₄ | — | CF₃ | H | H | H |
| CH₂=CHC₂H₄ | — | CF₃ | F | H | H |
| CH₂=CHC₂H₄ | — | CF₃ | F | F | H |
| CH₃CH=CHC₂H₄ | — | CF₃ | H | H | H |
| CH₃CH=CHC₂H₄ | — | CF₃ | F | H | H |
| CH₃CH=CHC₂H₄ | — | CF₃ | F | F | H |
| CH₃ | — | SF₅ | H | H | H |
| CH₃ | — | SF₅ | F | H | H |
| CH₃ | — | SF₅ | F | F | H |
| C₂H₅ | — | SF₅ | H | H | H |
| C₂H₅ | — | SF₅ | F | H | H |
| C₂H₅ | — | SF₅ | F | F | H |
| n-C₃H₇ | — | SF₅ | H | H | H |
| n-C₃H₇ | — | SF₅ | F | H | H |
| n-C₃H₇ | — | SF₅ | F | F | H |
| n-C₅H₁₁ | — | SF₅ | H | H | H |
| n-C₅H₁₁ | — | SF₅ | F | H | H |
| n-C₅H₁₁ | — | SF₅ | F | F | H |
| CH₂=CH | — | SF₅ | H | H | H |
| CH₂=CH | — | SF₅ | F | H | H |
| CH₂=CH | — | SF₅ | F | F | H |
| CH₃CH=CH | — | SF₅ | H | H | H |
| CH₃CH=CH | — | SF₅ | F | H | H |
| CH₃CH=CH | — | SF₅ | F | F | H |
| CH₂=CHC₂H₄ | — | SF₅ | H | H | H |
| CH₂=CHC₂H₄ | — | SF₅ | F | H | H |
| CH₂=CHC₂H₄ | — | SF₅ | F | F | H |
| CH₃CH=CHC₂H₄ | — | SF₅ | H | H | H |
| CH₃CH=CHC₂H₄ | — | SF₅ | F | H | H |
| CH₃CH=CHC₂H₄ | — | SF₅ | F | F | H |
| CH₃ | — | CH=CF₂ | H | H | H |
| CH₃ | — | CH=CF₂ | F | H | H |
| CH₃ | — | CH=CF₂ | F | F | H |
| C₂H₅ | — | CH=CF₂ | H | H | H |
| C₂H₅ | — | CH=CF₂ | F | H | H |
| C₂H₅ | — | CH=CF₂ | F | F | H |

|R|—(A¹—Z¹)ₘ—|Y|L¹|L²|L³|
|---|---|---|---|---|---|
|n-C₃H₇|—|CH=CF₂|H|H|H|
|n-C₃H₇|—|CH=CF₂|F|H|H|
|n-C₃H₇|—|CH=CF₂|F|F|H|
|n-C₅H₁₁|—|CH=CF₂|H|H|H|
|n-C₅H₁₁|—|CH=CF₂|F|H|H|
|n-C₅H₁₁|—|CH=CF₂|F|F|H|
|CH₂=CH|—|CH=CF₂|H|H|H|
|CH₂=CH|—|CH=CF₂|F|H|H|
|CH₂=CH|—|CH=CF₂|F|F|H|
|CH₃CH=CH|—|CH=CF₂|H|H|H|
|CH₃CH=CH|—|CH=CF₂|F|H|H|
|CH₃CH=CH|—|CH=CF₂|F|F|H|
|CH₂=CHC₂H₄|—|CH=CF₂|H|H|H|
|CH₂=CHC₂H₄|—|CH=CF₂|F|H|H|
|CH₂=CHC₂H₄|—|CH=CF₂|F|F|H|
|CH₃CH=CHC₂H₄|—|CH=CF₂|H|H|H|
|CH₃CH=CHC₂H₄|—|CH=CF₂|F|H|H|
|CH₃CH=CHC₂H₄|—|CH=CF₂|F|F|H|
|CH₃|—|OCHFCF₃|H|H|H|
|CH₃|—|OCHFCF₃|F|H|H|
|CH₃|—|OCHFCF₃|F|F|H|
|C₂H₅|—|OCHFCF₃|H|H|H|
|C₂H₅|—|OCHFCF₃|F|H|H|
|C₂H₅|—|OCHFCF₃|F|F|H|
|n-C₃H₇|—|OCHFCF₃|H|H|H|
|n-C₃H₇|—|OCHFCF₃|F|H|H|
|n-C₃H₇|—|OCHFCF₃|F|F|H|
|n-C₅H₁₁|—|OCHFCF₃|H|H|H|
|n-C₅H₁₁|—|OCHFCF₃|F|H|H|
|n-C₅H₁₁|—|OCHFCF₃|F|F|H|
|CH₂=CH|—|OCHFCF₃|H|H|H|
|CH₂=CH|—|OCHFCF₃|F|H|H|
|CH₂=CH|—|OCHFCF₃|F|F|H|
|CH₃CH=CH|—|OCHFCF₃|H|H|H|
|CH₃CH=CH|—|OCHFCF₃|F|H|H|
|CH₃CH=CH|—|OCHFCF₃|F|F|H|
|CH₂=CHC₂H₄|—|OCHFCF₃|H|H|H|
|CH₂=CHC₂H₄|—|OCHFCF₃|F|H|H|

-continued

| R | —(A¹—Z¹)ₘ— | Y | L¹ | L² | L³ | |
|---|---|---|---|---|---|---|
| CH₂=CHC₂H₄ | — | OCHFCF₃ | F | F | H | |
| CH₃CH=CHC₂H₄ | — | OCHFCF₃ | H | H | H | |
| CH₃CH=CHC₂H₄ | — | OCHFCF₃ | F | H | H | |
| CH₃CH=CHC₂H₄ | — | OCHFCF₃ | F | F | H | |
| CH₃ | — | OCF₂CHFCF₃ | H | H | H | |
| CH₃ | — | OCF₂CHFCF₃ | F | H | H | |
| CH₃ | — | OCF₂CHFCF₃ | F | F | H | |
| C₂H₅ | — | OCF₂CHFCF₃ | H | H | H | |
| C₂H₅ | — | OCF₂CHFCF₃ | F | H | H | |
| C₂H₅ | — | OCF₂CHFCF₃ | F | F | H | |
| n-C₃H₇ | — | OCF₂CHFCF₃ | H | H | H | |
| n-C₃H₇ | — | OCF₂CHFCF₃ | F | H | H | |
| n-C₃H₇ | — | OCF₂CHFCF₃ | F | F | H | |
| n-C₅H₁₁ | — | OCF₂CHFCF₃ | H | H | H | |
| n-C₅H₁₁ | — | OCF₂CHFCF₃ | F | H | H | |
| n-C₅H₁₁ | — | OCF₂CHFCF₃ | F | F | H | |
| CH₂=CH | — | OCF₂CHFCF₃ | H | H | H | |
| CH₂=CH | — | OCF₂CHFCF₃ | F | H | H | |
| CH₂=CH | — | OCF₂CHFCF₃ | F | F | H | |
| CH₃CH=CH | — | OCF₂CHFCF₃ | H | H | H | |
| CH₃CH=CH | — | OCF₂CHFCF₃ | F | H | H | |
| CH₃CH=CH | — | OCF₂CHFCF₃ | F | F | H | |
| CH₂=CHC₂H₄ | — | OCF₂CHFCF₃ | H | H | H | |
| CH₂=CHC₂H₄ | — | OCF₂CHFCF₃ | F | H | H | |
| CH₂=CHC₂H₄ | — | OCF₂CHFCF₃ | F | F | H | |
| CH₃CH=CHC₂H₄ | — | OCF₂CHFCF₃ | H | H | H | |
| CH₃CH=CHC₂H₄ | — | OCF₂CHFCF₃ | F | H | H | |
| CH₃CH=CHC₂H₄ | — | OCF₂CHFCF₃ | F | F | H | |
| CH₃O | — | F | F | F | F | |
| C₂H₅O | — | F | F | F | F | C 125 I |
| n-C₃H₇O | — | F | F | F | F | |
| n-C₄H₉O | — | F | F | F | F | C 78 I; Δn = 0.1610; Δε = 17.5 |
| n-C₅H₁₁O | — | F | F | F | F | |
| n-C₆H₁₃O | — | F | F | F | F | |
| CH₂=CHCH₂O | — | F | F | F | F | C 94 I; Δn = 0.1610; Δε = 18.3 |
| CH₃ | — | F | H | H | F | |
| CH₃ | — | F | F | H | F | |

-continued

| R | —(A¹—Z¹)ₘ— | Y | L¹ | L² | L³ | |
|---|---|---|---|---|---|---|
| CH₃ | — | F | F | F | F | C 114 I;<br>Δn = 0.1505;<br>Δε = 18.8 |
| C₂H₅ | — | F | H | H | F | |
| C₂H₅ | — | F | F | H | F | |
| C₂H₅ | — | F | F | F | F | |
| n-C₃H₇ | — | F | H | H | F | |
| n-C₃H₇ | — | F | F | H | F | |
| n-C₅H₁₁ | — | F | H | H | F | |
| n-C₅H₁₁ | — | F | F | H | F | |
| n-C₅H₁₁ | — | F | F | F | F | |
| CH₂=CH | — | F | H | H | F | |
| CH₂=CH | — | F | F | H | F | |
| CH₂=CH | — | F | F | F | F | |
| CH₃CH=CH | — | F | H | H | F | |
| CH₃CH=CH | — | F | F | H | F | |
| CH₃CH=CH | — | F | F | F | F | |
| CH₂=CHC₂H₄ | — | F | H | H | F | |
| CH₂=CHC₂H₄ | — | F | F | H | F | |
| CH₂=CHC₂H₄ | — | F | F | F | F | |
| CH₃CH=CHC₂H₄ | — | F | H | H | F | |
| CH₃CH=CHC₂H₄ | — | F | F | H | F | |
| CH₃CH=CHC₂H₄ | — | F | F | F | F | |
| CH₃ | — | OCF₃ | H | H | F | |
| CH₃ | — | OCF₃ | F | H | F | |
| CH₃ | — | OCF₃ | F | F | F | C 110 I;<br>Δn = 0.1490;<br>Δε = 20.7 |
| C₂H₅ | — | OCF₃ | H | H | F | |
| C₂H₅ | — | OCF₃ | F | H | F | |
| C₂H₅ | — | OCF₃ | F | F | F | |
| n-C₃H₇ | — | OCF₃ | H | H | F | |
| n-C₃H₇ | — | OCF₃ | F | H | F | |
| n-C₃H₇ | — | OCF₃ | F | F | F | |
| n-C₅H₁₁ | — | OCF₃ | H | H | F | |
| n-C₅H₁₁ | — | OCF₃ | F | H | F | |
| n-C₅H₁₁ | — | OCF₃ | F | F | F | |
| CH₂=CH | — | OCF₃ | H | H | F | |
| CH₂=CH | — | OCF₃ | F | H | F | |
| CH₂=CH | — | OCF₃ | F | F | F | |

-continued

| R | —(A¹—Z¹)ₘ— | Y | L¹ | L² | L³ |
|---|---|---|---|---|---|
| CH₃CH=CH | — | OCF₃ | H | H | F |
| CH₃CH=CH | — | OCF₃ | F | H | F |
| CH₃CH=CH | — | OCF₃ | F | F | F |
| CH₂=CHC₂H₄ | — | OCF₃ | H | H | F |
| CH₂=CHC₂H₄ | — | OCF₃ | F | H | F |
| CH₂=CHC₂H₄ | — | OCF₃ | F | F | F |
| CH₃CH=CHC₂H₄ | — | OCF₃ | H | H | F |
| CH₃CH=CHC₂H₄ | — | OCF₃ | F | H | F |
| CH₃CH=CHC₂H₄ | — | OCF₃ | F | F | F |
| CH₃ | — | CF₃ | H | H | F |
| CH₃ | — | CF₃ | F | H | F |
| CH₃ | — | CF₃ | F | F | F |
| C₂H₅ | — | CF₃ | H | H | F |
| C₂H₅ | — | CF₃ | F | H | F |
| C₂H₅ | — | CF₃ | F | F | F |
| n-C₃H₇ | — | CF₃ | H | H | F |
| n-C₃H₇ | — | CF₃ | F | H | F |
| n-C₃H₇ | — | CF₃ | F | F | F |
| n-C₅H₁₁ | — | CF₃ | H | H | F |
| n-C₅H₁₁ | — | CF₃ | F | H | F |
| n-C₅H₁₁ | — | CF₃ | F | F | F |
| CH₂=CH | — | CF₃ | H | H | F |
| CH₂=CH | — | CF₃ | F | H | F |
| CH₂=CH | — | CF₃ | F | F | F |
| CH₃CH=CH | — | CF₃ | H | H | F |
| CH₃CH=CH | — | CF₃ | F | H | F |
| CH₃CH=CH | — | CF₃ | F | F | F |
| CH₂=CHC₂H₄ | — | CF₃ | H | H | F |
| CH₂=CHC₂H₄ | — | CF₃ | F | H | F |
| CH₂=CHC₂H₄ | — | CF₃ | F | F | F |
| CH₃CH=CHC₂H₄ | — | CF₃ | H | H | F |
| CH₃CH=CHC₂H₄ | — | CF₃ | F | H | F |
| CH₃CH=CHC₂H₄ | — | CF₃ | F | F | F |
| CH₃ | — | SF₅ | H | H | F |
| CH₃ | — | SF₅ | F | H | F |
| CH₃ | — | SF₅ | F | F | F |
| C₂H₅ | — | SF₅ | H | H | F |
| C₂H₅ | — | SF₅ | F | H | F |
| C₂H₅ | — | SF₅ | F | F | F |

-continued

| R | —(A¹—Z¹)ₘ— | Y | L¹ | L² | L³ |
|---|---|---|---|---|---|
| n-C₃H₇ | — | SF₅ | H | H | F |
| n-C₃H₇ | — | SF₅ | F | H | F |
| n-C₃H₇ | — | SF₅ | F | F | F |
| n-C₅H₁₁ | — | SF₅ | H | H | F |
| n-C₅H₁₁ | — | SF₅ | F | H | F |
| n-C₅H₁₁ | — | SF₅ | F | F | F |
| CH₂=CH | — | SF₅ | H | H | F |
| CH₂=CH | — | SF₅ | F | H | F |
| CH₂=CH | — | SF₅ | F | F | F |
| CH₃CH=CH | — | SF₅ | H | H | F |
| CH₃CH=CH | — | SF₅ | F | H | F |
| CH₃CH=CH | — | SF₅ | F | F | F |
| CH₂=CHC₂H₄ | — | SF₅ | H | H | F |
| CH₂=CHC₂H₄ | — | SF₅ | F | H | F |
| CH₂=CHC₂H₄ | — | SF₅ | F | F | F |
| CH₃CH=CHC₂H₄ | — | SF₅ | H | H | F |
| CH₃CH=CHC₂H₄ | — | SF₅ | F | H | F |
| CH₃CH=CHC₂H₄ | — | SF₅ | F | F | F |
| CH₃ | — | CH=CF₂ | H | H | F |
| CH₃ | — | CH=CF₂ | F | H | F |
| CH₃ | — | CH=CF₂ | F | F | F |
| C₂H₅ | — | CH=CF₂ | H | H | F |
| C₂H₅ | — | CH=CF₂ | F | H | F |
| C₂H₅ | — | CH=CF₂ | F | F | F |
| n-C₃H₇ | — | CH=CF₂ | H | H | F |
| n-C₃H₇ | — | CH=CF₂ | F | H | F |
| n-C₃H₇ | — | CH=CF₂ | F | F | F |
| n-C₅H₁₁ | — | CH=CF₂ | H | H | F |
| n-C₅H₁₁ | — | CH=CF₂ | F | H | F |
| n-C₅H₁₁ | — | CH=CF₂ | F | F | F |
| CH₂=CH | — | CH=CF₂ | H | H | F |
| CH₂=CH | — | CH=CF₂ | F | H | F |
| CH₂=CH | — | CH=CF₂ | F | F | F |
| CH₃CH=CH | — | CH=CF₂ | H | H | F |
| CH₃CH=CH | — | CH=CF₂ | F | H | F |
| CH₃CH=CH | — | CH=CF₂ | F | F | F |
| CH₂=CHC₂H₄ | — | CH=CF₂ | H | H | F |
| CH₂=CHC₂H₄ | — | CH=CF₂ | F | H | F |

-continued

| R | —(A¹—Z¹)ₘ— | Y | L¹ | L² | L³ |
|---|---|---|---|---|---|
| CH₂=CHC₂H₄ | — | CH=CF₂ | F | F | F |
| CH₃CH=CHC₂H₄ | — | CH=CF₂ | H | H | F |
| CH₃CH=CHC₂H₄ | — | CH=CF₂ | F | H | F |
| CH₃CH=CHC₂H₄ | — | CH=CF₂ | F | F | F |
| CH₃ | — | OCHFCF₃ | H | H | F |
| CH₃ | — | OCHFCF₃ | F | H | F |
| CH₃ | — | OCHFCF₃ | F | F | F |
| C₂H₅ | — | OCHFCF₃ | H | H | F |
| C₂H₅ | — | OCHFCF₃ | F | H | F |
| C₂H₅ | — | OCHFCF₃ | F | F | F |
| n-C₃H₇ | — | OCHFCF₃ | H | H | F |
| n-C₃H₇ | — | OCHFCF₃ | F | H | F |
| n-C₃H₇ | — | OCHFCF₃ | F | F | F |
| n-C₅H₁₁ | — | OCHFCF₃ | H | H | F |
| n-C₅H₁₁ | — | OCHFCF₃ | F | H | F |
| n-C₅H₁₁ | — | OCHFCF₃ | F | F | F |
| CH₂=CH | — | OCHFCF₃ | H | H | F |
| CH₂=CH | — | OCHFCF₃ | F | H | F |
| CH₂=CH | — | OCHFCF₃ | F | F | F |
| CH₃CH=CH | — | OCHFCF₃ | H | H | F |
| CH₃CH=CH | — | OCHFCF₃ | F | H | F |
| CH₃CH=CH | — | OCHFCF₃ | F | F | F |
| CH₂=CHC₂H₄ | — | OCHFCF₃ | H | H | F |
| CH₂=CHC₂H₄ | — | OCHFCF₃ | F | H | F |
| CH₂=CHC₂H₄ | — | OCHFCF₃ | F | F | F |
| CH₃CH=CHC₂H₄ | — | OCHFCF₃ | H | H | F |
| CH₃CH=CHC₂H₄ | — | OCHFCF₃ | F | H | F |
| CH₃CH=CHC₂H₄ | — | OCHFCF₃ | F | F | F |
| CH₃ | — | OCF₂CHFCF₃ | H | H | F |
| CH₃ | — | OCF₂CHFCF₃ | F | H | F |
| CH₃ | — | OCF₂CHFCF₃ | F | F | F |
| C₂H₅ | — | OCF₂CHFCF₃ | H | H | F |
| C₂H₅ | — | OCF₂CHFCF₃ | F | H | F |
| C₂H₅ | — | OCF₂CHFCF₃ | F | F | F |
| n-C₃H₇ | — | OCF₂CHFCF₃ | H | H | F |
| n-C₃H₇ | — | OCF₂CHFCF₃ | F | H | F |
| n-C₃H₇ | — | OCF₂CHFCF₃ | F | F | F |
| n-C₅H₁₁ | — | OCF₂CHFCF₃ | H | H | F |
| n-C₅H₁₁ | — | OCF₂CHFCF₃ | F | H | F |

-continued

| R | —(A¹—Z¹)ₘ— | Y | L¹ | L² | L³ |
|---|---|---|---|---|---|
| n-C₅H₁₁ | — | OCF₂CHFCF₃ | F | F | F |
| CH₂=CH | — | OCF₂CHFCF₃ | H | H | F |
| CH₂=CH | — | OCF₂CHFCF₃ | F | H | F |
| CH₂=CH | — | OCF₂CHFCF₃ | F | F | F |
| CH₃CH=CH | — | OCF₂CHFCF₃ | H | H | F |
| CH₃CH=CH | — | OCF₂CHFCF₃ | F | H | F |
| CH₃CH=CH | — | OCF₂CHFCF₃ | F | F | F |
| CH₂=CHC₂H₄ | — | OCF₂CHFCF₃ | H | H | F |
| CH₂=CHC₂H₄ | — | OCF₂CHFCF₃ | F | H | F |
| CH₂=CHC₂H₄ | — | OCF₂CHFCF₃ | F | F | F |
| CH₃CH=CHC₂H₄ | — | OCF₂CHFCF₃ | H | H | F |
| CH₃CH=CHC₂H₄ | — | OCF₂CHFCF₃ | F | H | F |
| CH₃CH=CHC₂H₄ | — | OCF₂CHFCF₃ | F | F | F |

EXAMPLE M1

| | | | |
|---|---|---|---|
| CCP-3F.F.F | 5.0% | Clearing point [°C.]: | 91.0 |
| CCP-30CF₃.F | 12.0% | Δn [589 nm, 20° C.]: | 0.1092 |
| CCP-30CF₃ | 8.0% | Δε [1 kHz, 20° C.]: | 10.2 |
| CCP-40CF₃ | 8.0% | γ₁ [mPa · s, 20° C.]: | 176 |
| CCP-50CF₃ | 8.0% | | |
| CGU-2-F | 10.0% | | |
| CGU-3-F | 10.0% | | |
| CGU-5-F | 2.0% | | |
| BCH-3F.F.F | 12.0% | | |
| CC-5-V | 8.0% | | |
| CCZP-2-OT | 10.0% | | |
| IS-8633 | 3.0% | | |
| IS-8634 | 4.0% | | |

EXAMPLE M2

| | | | |
|---|---|---|---|
| CC-5-V | 10.0% | Clearing point [°C.]: | 110.0 |
| CCG-V-F | 15.0% | Δn [589 nm, 20° C.]: | 0.1101 |
| CCP-2F.F.F | 3.5% | Δε [1 kHz, 20° C.]: | 5.2 |
| CCP-30CF₃ | 8.0% | γ₁ [mPa · s, 20° C.]: | 150 |
| CCP-50CF₃ | 8.0% | | |
| BCH-2F.F | 8.0% | | |
| BCH-3F.F | 8.0% | | |
| BCH-5F.F.F | 7.5% | | |
| CBC-33F | 3.0% | | |
| CCP-V-1 | 18.0% | | |
| PCH-7F | 4.0% | | |
| IS-8633 | 4.0% | | |
| IS-8634 | 3.0% | | |

EXAMPLE M3

| | | | |
|---|---|---|---|
| CC-5-V | 20.0% | Clearing point [°C.]: | 108.6 |
| CCG-V-F | 5.5% | Δn [589 nm, 20° C.]: | 0.1092 |
| CCP-2F.F.F | 2.5% | Δε[1 kHz, 20° C.]: | 5.3 |
| CCP-30CF₃ | 8.0% | γ₁ [mPa · s, 20° C.]: | 139 |
| CCP-50CF₃ | 8.0% | | |
| BCH-2F.F | 5.5% | | |
| BCH-3F.F | 8.0% | | |
| BCH-5F.F.F | 16.0% | | |
| CBC-33F | 3.5% | | |
| CCP-V-1 | 17.0% | | |
| IS-8633 | 3.0% | | |
| IS-8634 | 3.0% | | |

EXAMPLE M4

| | | | |
|---|---|---|---|
| BCH-3F.F | 10.81% | Clearing point [°C.]: | 79.6 |
| BCH-5F.F | 9.01% | γ1 [mPa · s, 20° C.]: | 112 |
| ECCP-30CF₃ | 4.51% | | |
| ECCP-50CF₃ | 4.51% | | |
| CBC-33F | 1.80% | | |
| CBC-53F | 1.80% | | |
| CBC-55F | 1.80% | | |
| PCH-6F | 7.21% | | |
| PCH-7F | 5.41% | | |
| CCP-20CF₃ | 7.21% | | |
| CCP-30CF₃ | 10.81% | | |
| CCP-40CF₃ | 6.31% | | |
| CCP-50CF₃ | 9.91% | | |
| PCH-5F | 9.01% | | |
| IS-9003 | 9.89% | | |

EXAMPLE M5

| | | | |
|---|---|---|---|
| BCH-3F.F | 10.80% | Clearing point [°C.]: | 79 |
| BCH-5F.F | 9.00% | Δn [589 nm, 20° C.]: | 0.1010 |
| ECCP-30CF₃ | 4.50% | Δε [1 kHz, 20° C.]: | 6.0 |
| ECCP-50CF₃ | 4.50% | | |

-continued
| | |
|---|---|
| CBC-33F | 1.80% |
| CBC-53F | 1.80% |
| CBC-55F | 1.80% |
| PCH-6F | 7.20% |
| PCH-7F | 5.40% |
| CCP-20CF$_3$ | 7.20% |
| CCP-30CF$_3$ | 10.80% |
| CCP-40CF$_3$ | 6.30% |
| CCP-50CF$_3$ | 9.90% |
| PCH-5F | 9.00% |
| IS-9003 | 9.99% |
EXAMPLE M6
| | | | |
|---|---|---|---|
| CCP-20CF$_3$ | 8.0% | S → N [°C.]: | <−40 |
| CCP-30CF$_3$ | 8.0% | Clearing point [°C.]: | 78.5 |
| CCP-40CF$_3$ | 3.0% | Δn [589 nm, 20° C.]: | 0.1018 |
| PGU-2-F | 10.0% | $\gamma_1$ [mPa · s, 20° C.]: | 88 |
| IS-9003 | 9.0% | d · Δn [μm]: | 0.5 |
| CGZP-2-0T | 11.0% | Twist [°]: | 90 |
| CGZP-3-0T | 9.0% | $V_{10}$ [V]: | 1.35 |
| CCZU-2-F | 4.0% | | |
| CCZU-3-F | 14.0% | | |
| CC-3-V | 19.0% | | |
| CC-3-V1 | 5.0% | | |
EXAMPLE M7
4 V Driver
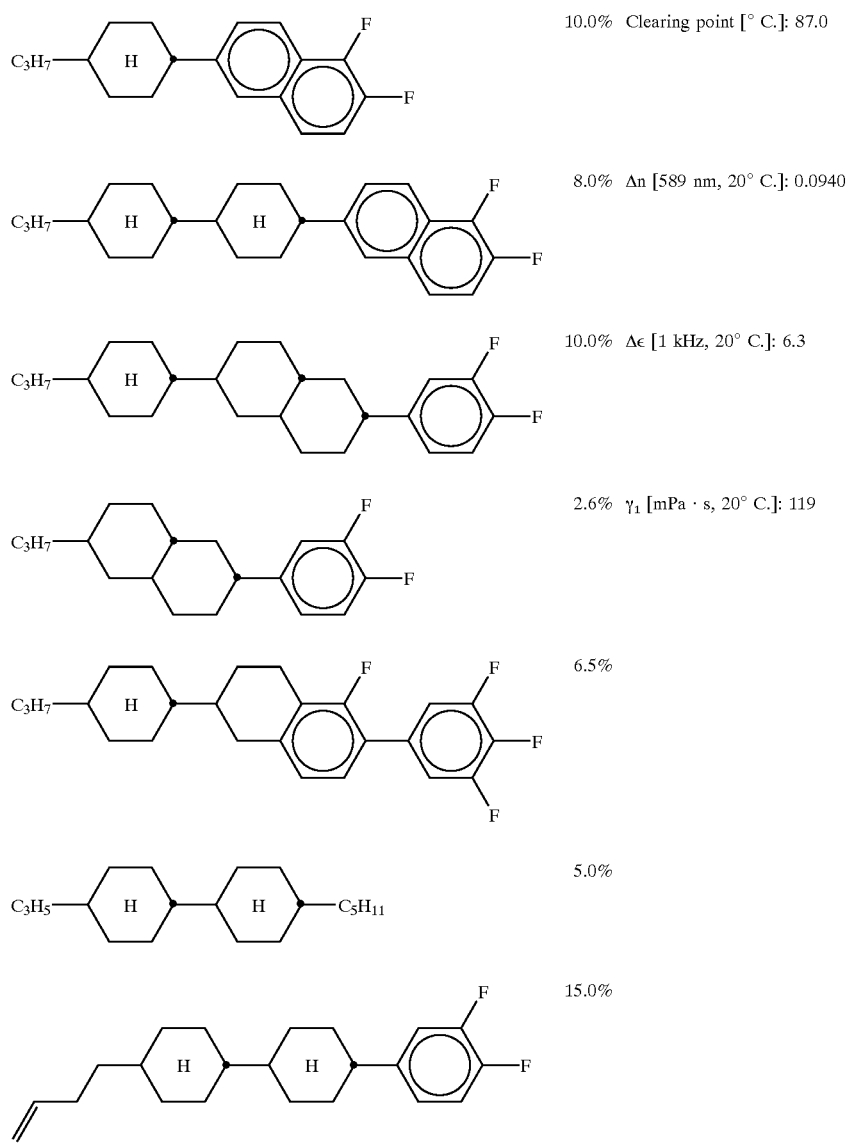

-continued
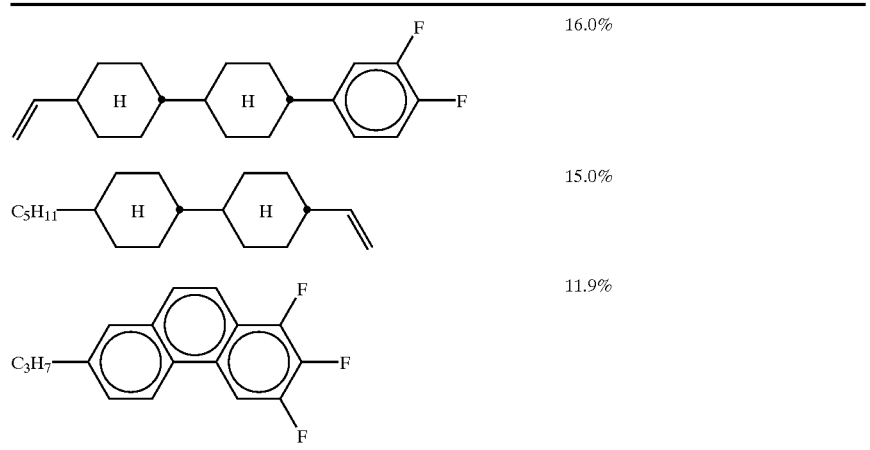
| | |
|---|---|
| | 16.0% |
| | 15.0% |
| | 11.9% |
EXAMPLE M8
3.3 V Driver
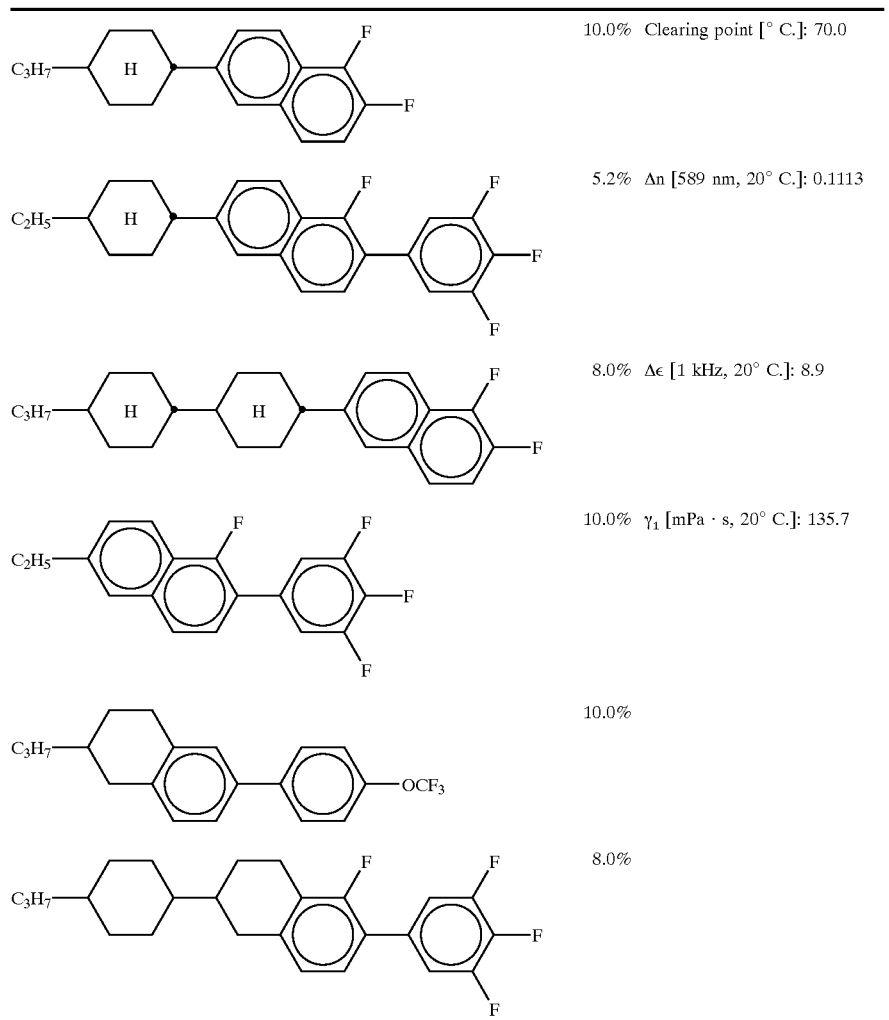
| | | |
|---|---|---|
| 10.0% | Clearing point [° C.]: | 70.0 |
| 5.2% | Δn [589 nm, 20° C.]: | 0.1113 |
| 8.0% | Δε [1 kHz, 20° C.]: | 8.9 |
| 10.0% | γ$_1$ [mPa · s, 20° C.]: | 135.7 |
| 10.0% | | |
| 8.0% | | |

-continued

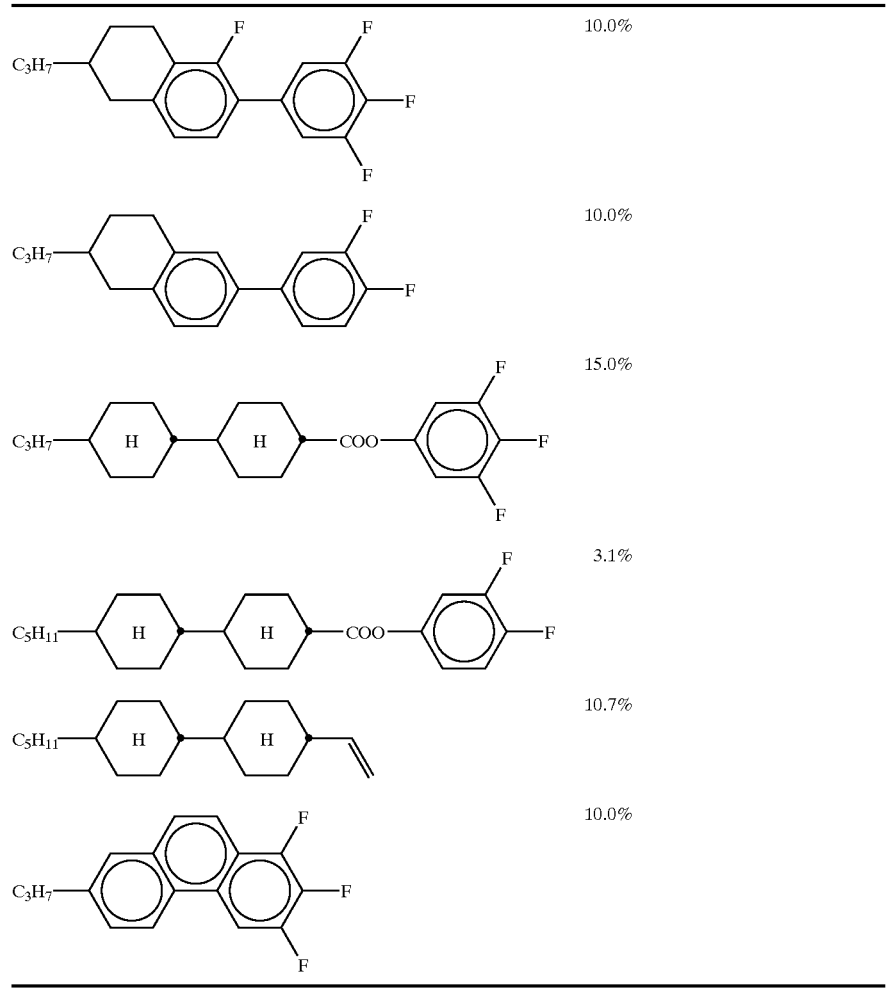

| | |
|---|---|
| | 10.0% |
| | 10.0% |
| | 15.0% |
| | 3.1% |
| | 10.7% |
| | 10.0% |

EXAMPLE M9

| | | | |
|---|---|---|---|
| GGP-5-Cl | 16.00% | Clearing point [°C.]: | +97.5 |
| PGIGI-3-F | 5.00% | Δn [589 nm, 20° C.]: | 0.1800 |
| BCH-2F.F | 8.00% | Δε [1 kHz, 20° C.]: | +12.7 |
| BCH-3F.F | 8.00% | γ$_1$ [mPa · s, 20° C.]: | 304 |
| BCH-5F.F | 7.00% | V$_{10,20}$ [V]: | 1.07 |
| CGU-2-F | 4.00% | | |
| BCH-3F.F.F | 10.00% | | |
| PGU-2-F | 8.00% | | |
| PGU-3-F | 7.00% | | |
| CCGU-3-F | 11.00% | | |
| BCH-32 | 5.00% | | |
| CBC-33F | 3.00% | | |
| CBC-53F | 2.00% | | |
| IS-9003 | 3.00% | | |
| IS-8965 | 3.00% | | |

The entire disclosures of all applications, patents and publications, cited herein and of corresponding German application Nos. 10127482.3 filed Jun. 7, 2001 and 10136965.4 filed Jul. 28, 2001 are incorporated in their entirety by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A liquid-crystalline medium comprising at least two mesogenic compounds, including at least one (dihydro) phenanthrene derivative of the formula I

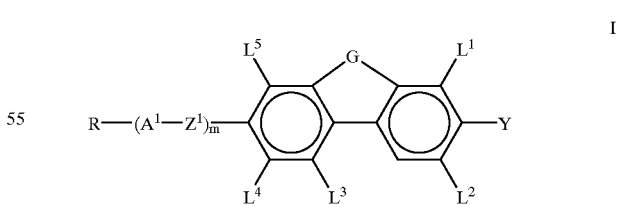

in which

R is an alkyl or alkenyl radical having up to 15 carbon atoms which is unsubstituted, monosubstituted by CN or CF$_3$ or at least monosubstituted by halogen, where, in addition, one or more CH$_2$ groups in these radicals may be replaced by —O—, —S—, —C≡C—, —OC—O— or —O—CO— in such a way that O atoms are not linked directly to one another, A¹ a) is a 1,4-cyclohexenylene or 1,4-cyclohexylene radical, in which one or two non-adjacent CH₂ groups may be replaced by —O— or —S—, or b) a 1,4-phenylene radical, in which one or two CH groups may be replaced by N, where the radicals a) and b) may be monosubstituted or polysubstituted by fluorine, $Z^1$ is —CO—O—, —O—CO—, —CF₂O—, —OCF₂—, —CH₂O—, —OCH₂—, —CH₂CH₂—, —C₂F₄—, —CH=CH—, —C≡C— or a single bond, Y is H, F, Cl, CN, SF₅, NCS, SCN or an alkyl, alkenyl, alkenyloxy or alkoxy radical having from 1 to 5 carbon atoms which is monohalogenated or polyhalogenated, G is —CH₂CH₂—, —CH=CF— or —CH=CH—, $L^1, L^2, L^3$, $L^4$ and $L^5$ are each, independently of one another, H or F, and m is 0, 1 or 2, and one or more compounds selected from the group consisting of the general formulae II, III, IV, V, VI, VII, VIII and IX:

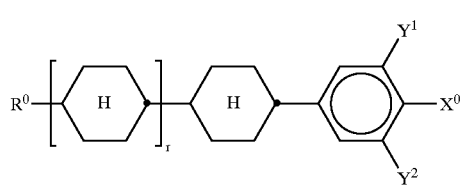

II

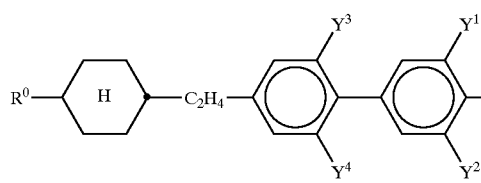

III

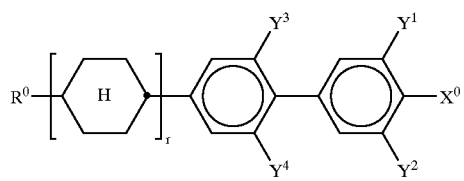

IV

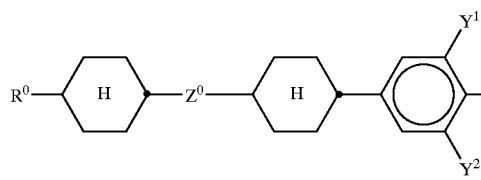

V

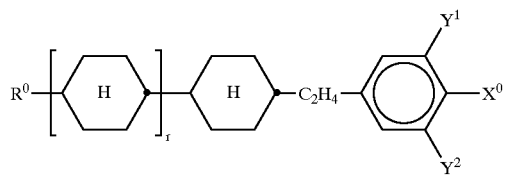

VI

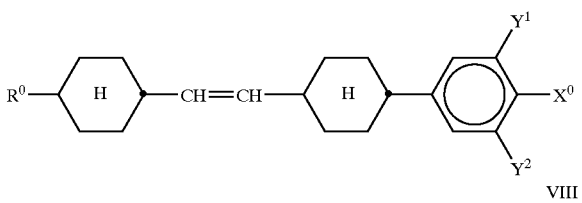

VII

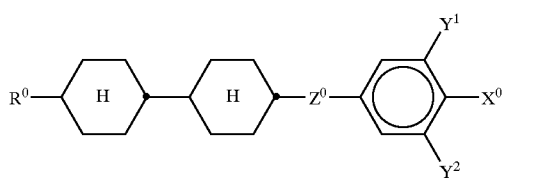

VIII

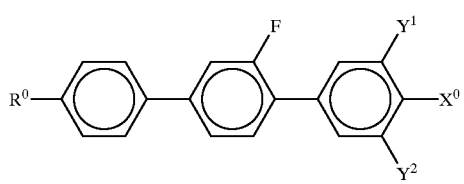

IX in which the individual radicals have the following meanings:

$R^0$ is n-alkyl, oxaalkyl, fluoroalkyl, alkenyloxy or alkenyl, each having up to 9 carbon atoms, $X^0$ is halogenated alkoxy having from 1 to 6 carbon atoms, $Z^0$ is —C₂H₄—, —C₂F₄—, —CH₂O—, —OCH₂—, —CF₂O—, —OCF₂— or —COO—, $Y^1, Y^2$, $Y^3$ and $Y^4$ are each, independently of one another, H or F, and r is 0 or 1.

2. The liquid-crystalline (dihydro)phenanthrene derivative according to claim 1, wherein R is a straight-chain alkyl radical having from 1 to 10 carbon atoms or an alkenyl radical having from 2 to 10 carbon atoms.

3. The liquid-crystalline (dihydro)phenanthrene derivative according to claim 1, wherein Y is H, F, Cl, CN, CF₃, CF₂H, OCF₃, OCF₂H, OCFHCF₃, OCFHCFH₂, OCFHCF₂H, OCF₂CH₃, OCF₂CFH₂, OCF₂CF₂H, OCF₂CF₂CF₂H, OCF₂CF₂CFH₂, OCFHCF₂CF₃, OCFHCF₂CF₂H, OCF₂CF₂CF₃, OCF₂CHFCF₃ or OCClFCF₂CF₃.

4. The liquid-crystalline (dihydro)phenanthrene derivative claim 1, wherein m=0.

5. A liquid-crystalline (dihydro)phenanthrene derivative according to claim 1 of the sub-formulae I1 to I27:

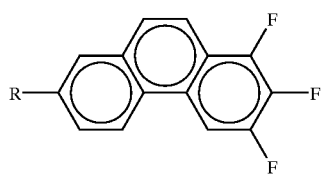

I1

I2 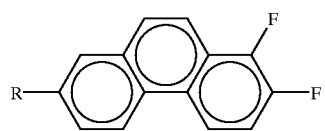
I3 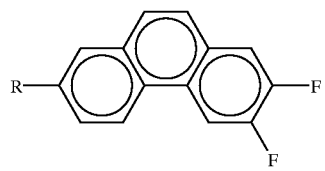
I4 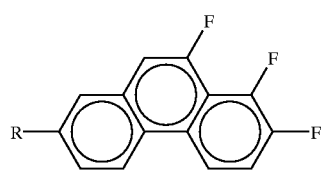
I5 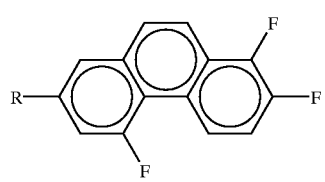
I6 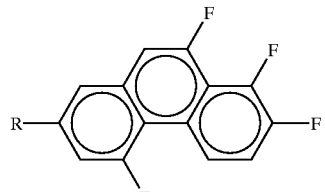
I7 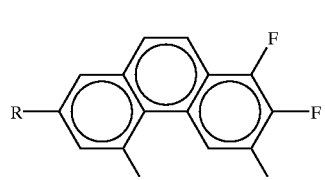
I8 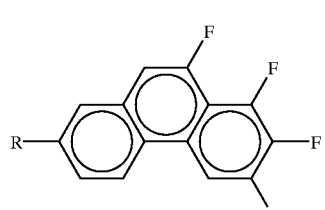
I9 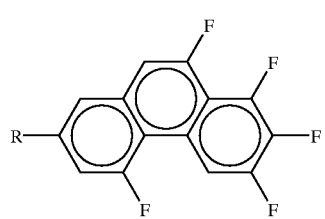
I10 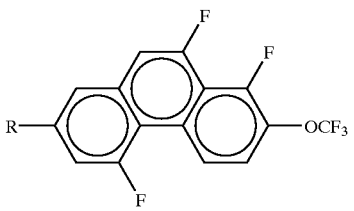
I11 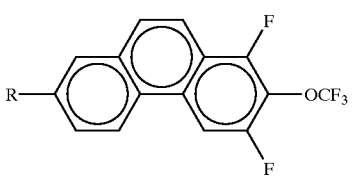
I12 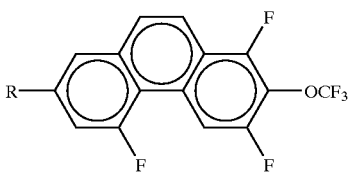
I13 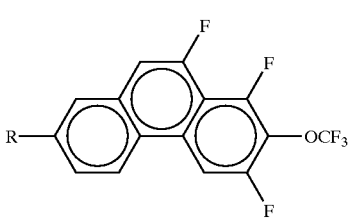
I14 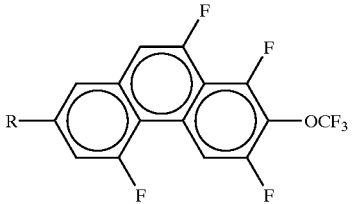
I15 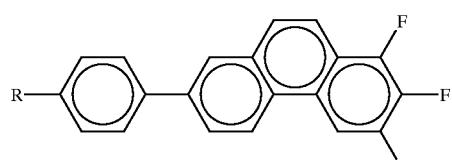
I16 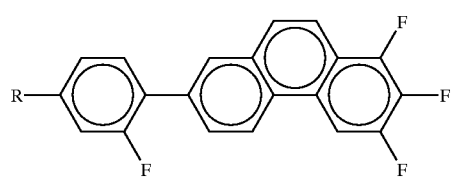
I17

-continued

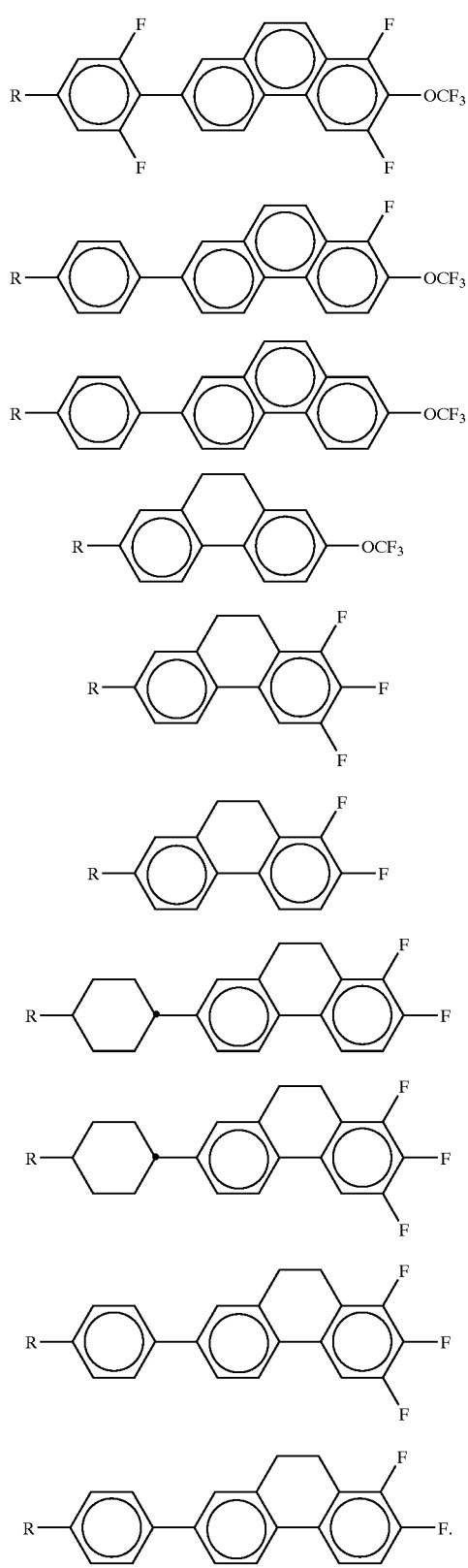

I18
I19
I20
I21
I22
I23
I24
I25
I26
I27

6. The medium according to claim 1, wherein the proportion of compounds of the formulae I to IX in the mixture as a whole is at least 50% by weight.

7. The medium according to claim 1, further comprising one or more compounds of the formulae RI to RVIII

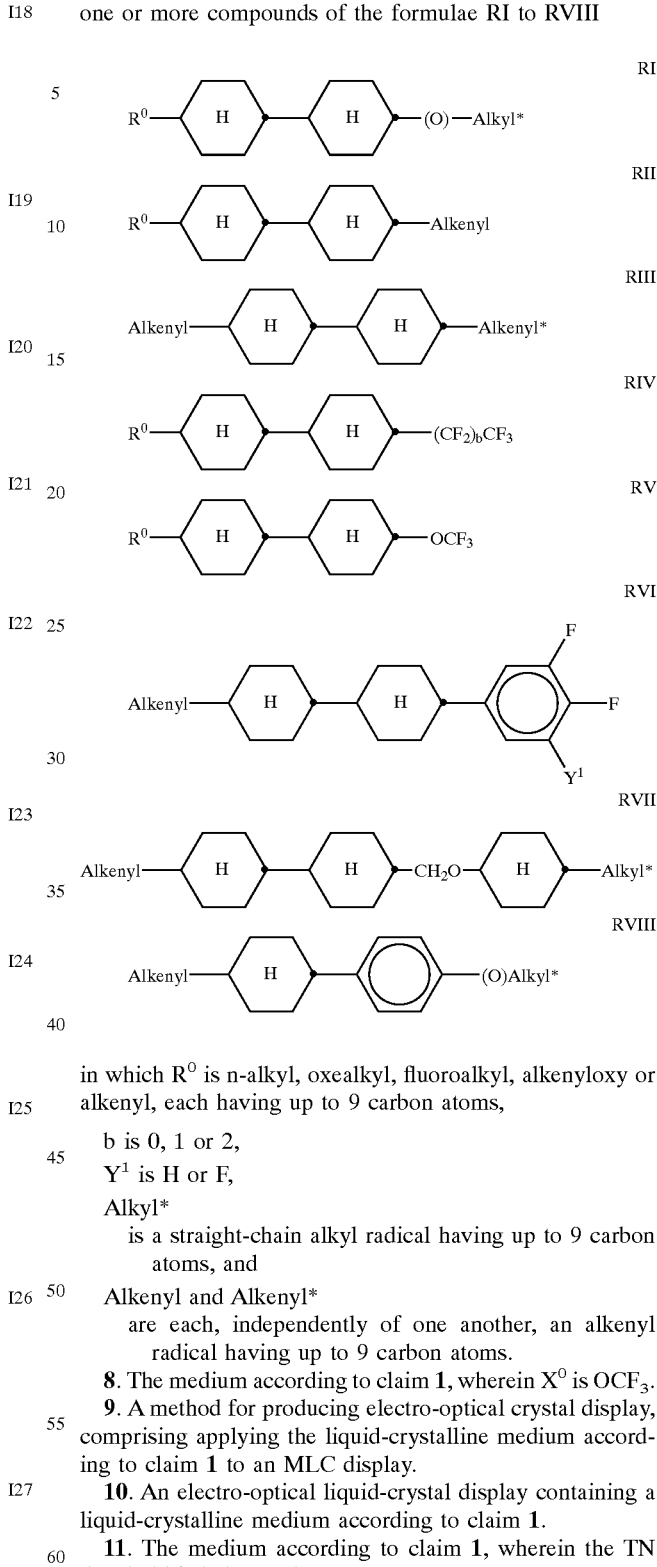

in which $R^0$ is n-alkyl, oxealkyl, fluoroalkyl, alkenyloxy or alkenyl, each having up to 9 carbon atoms, b is 0, 1 or 2, $Y^1$ is H or F, Alkyl*
  is a straight-chain alkyl radical having up to 9 carbon atoms, and Alkenyl and Alkenyl*
  are each, independently of one another, an alkenyl radical having up to 9 carbon atoms.

8. The medium according to claim 1, wherein $X^0$ is $OCF_3$.

9. A method for producing electro-optical crystal display, comprising applying the liquid-crystalline medium according to claim 1 to an MLC display.

10. An electro-optical liquid-crystal display containing a liquid-crystalline medium according to claim 1.

11. The medium according to claim 1, wherein the TN threshold is below 1.5 V.

12. The medium according to claim 1, wherein the TN threshold is below 1.3 V.

13. The medium according to claim 1, wherein the TN threshold is below 1.0 V.

14. The medium according to claim 1, having a rotational viscosity of 100–200 mPa·s.

15. The medium according to claim 1, having a rotational viscosity of no more than 130 mPa·s.

16. The medium according to claim 1, having a clearing point above 110° C.

17. The medium according to claim 1, wherein the medium comprises a compound of the formula II.

18. The medium according to claim 1, wherein the medium comprises a compound of the formula III.

19. The medium according to claim 17, wherein the medium further comprises a compound of the formula III.

* * * * *